United States Patent [19]

Kojiri et al.

[11] Patent Number: 5,668,271
[45] Date of Patent: *Sep. 16, 1997

[54] INDOLOPYRROLOCARBAZOLE DERIVATIVES

[75] Inventors: Katsuhisa Kojiri; Hisao Kondo; Hiroharu Arakawa; Mitsuru Ohkubo; Hiroyuki Suda, all of Tsukuba, Japan

[73] Assignee: Banyu Pharmaceutical Co., Ltd., Tokyo, Japan

[*] Notice: The term of this patent shall not extend beyond the expiration date of Pat. No. 5,591,842.

[21] Appl. No.: 474,659

[22] Filed: Jun. 7, 1995

Related U.S. Application Data

[60] Division of Ser. No. 255,980, Jun. 8, 1994, Pat. No. 5,591,842, which is a continuation-in-part of Ser. No. 981,070, Nov. 24, 1992.

[30] Foreign Application Priority Data

| Nov. 29, 1991 | [JP] | Japan | 3-341916 |
| Feb. 18, 1992 | [JP] | Japan | 4-069269 |
| Sep. 1, 1992 | [JP] | Japan | 4-257306 |

[51] Int. Cl.$^6$ .............. C07H 19/23; C07D 273/00
[52] U.S. Cl. .............. 536/27.1; 540/545; 548/400; 548/490; 548/364.4; 548/311.7; 548/240; 548/215; 548/181; 546/276.7
[58] Field of Search .............. 536/4.1, 27.1; 548/373.1, 400, 490; 514/23, 25, 410; 540/545

[56] References Cited

U.S. PATENT DOCUMENTS

| 4,912,107 | 3/1990 | Kleinschroth et al. | 514/232.5 |
| 4,923,986 | 5/1990 | Murakata et al. | 540/545 |
| 5,106,864 | 4/1992 | Suda et al. | 514/410 |
| 5,227,396 | 7/1993 | Laakso et al. | 514/410 |

FOREIGN PATENT DOCUMENTS

| 58351 | 1/1992 | Australia. |
| 0328000 | 3/1989 | European Pat. Off.. |
| 0388956 | 9/1990 | European Pat. Off.. |
| 3835842 | 4/1990 | Germany. |
| 3-20277 | 3/1991 | Japan. |
| WO91/18003 | 11/1991 | WIPO. |

OTHER PUBLICATIONS

Joyce, et al., J. Org. Chem., 52, No. 7 (1987) pp. 1177–1185.
Kaneko, et al., J. Antibiotics, vol. XLIII, No. 1 (1989) pp. 125–127.
47th Japan Soc. of Cancer General Mtg.Article (1988) pp. 12–15 English Abs.
Kojiri, et al., J. Antibiotics, vol. 44, No. 7 (Jul. 1991) pp. 723–728.
Hughes, et al., J. Chem. Soc. Perkins Trans. 1, (1990) pp. 2475–2480.
Reynolds, et al., J. Am. Chem. Soc. 60, 1938, pp. 2559–2561.
Bush, et al., J. Antibiotics, vol. XL, No. 5, (May 1987) pp. 668–678.

*Primary Examiner*—John Kight
*Assistant Examiner*—Howard C. Lee
*Attorney, Agent, or Firm*—Sherman and Shalloway

[57] ABSTRACT

Indolopyrrocarbazole derivatives represented by formula (I) and the pharmaceutically acceptable salts thereof have excellent antitumor activity as evidenced by their in vitro proliferation inhibiting activity against mouse leukemia cell, human gastric cancer cell, human lung cancer cell and human colon cancer cell,

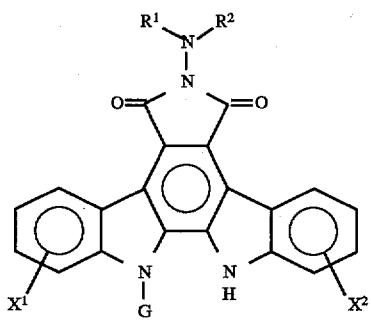

wherein $R^1$ and $R^2$ independently represent, for example, a hydrogen atom or various hydrocarbon groups which may be substituted or heterocyclic groups which may also be substituted; or a group —Y—$R^3$ where Y represents a carbonyl group, thiocarbonyl group or sulfonyl group and $R^3$ represents a hydrogen atom or one of various aliphatic, cycloaliphatic, aryl, nitrogen-containing (e.g. amino, hydrazino, etc) or heterocyclic groups, which groups may be substituted by various substituents; or $R^1$ and $R^2$ may combine to represent a lower alkylidene group which may be substituted; or $R^1$ and $R^2$, together with the N-atom to which they are bonded form a heterocyclic group which may be substituted;

G represents a pentose or hexose group; and $X^1$ and $X^2$, independently, represent, for example, hydrogen, halogen, amino, hydroxyl, alkoxy, aryloxy, carboxyl, alkoxycarbonyl or alkyl. These compounds have improved water solubility as compared to rebeccamycin.

3 Claims, No Drawings

INDOLOPYRROLOCARBAZOLE DERIVATIVES

This is a division of application Ser. No. 08/255,980, filed Jun. 8, 1994, now U.S. Pat. No. 5,591,842; which is a continuation-in-part of application Ser. No. 07/981,070 filed Nov. 24, 1992.

This invention is useful in the field of medicine, and relates to novel indolopyrrolocarbazole derivatives inhibiting proliferation of antitumor cells and exhibiting an antitumor effect, a process for preparation thereof and a use thereof.

In the field of cancer chemotherapy, many compounds are already put to practical use as an antitumor agent. However, the effect thereof on various kind of tumors is not always adequate, and the problem of resistance of tumor cells against these drugs makes clinical use of these antitumor agents complicated [refer to The 47th Japan Society of Cancer General Meeting Article, pages 12 to 15 (1988)].

In such state of things, development of novel carcinostatic substances is always made in the filed of cancer therapy. Particularly, substances are necessitated which overcome resistance against existing carcinostatic substances and exhibit effectiveness against such kinds of cancers on which existing carcinostatic substances cannot exhibit sufficient effects.

In the light of such present state of things, the present inventors widely screened microbial metabolic products, as a result, found a novel antitumor activity-possessing compound BE-13793C (12,13-dihydro-1,11-dihydroxy-5H-indolo[2,3-a]pyrrolo[3,4-c]carbazole-5,7(6H)-dione), and disclosed it [refer to Japanese Laid-Open Patent Publication No. 20277/1991 and J. Antibiotics, 44, 723–728 (1991)].

Thereafter, the present inventors created indolopyrrolocarbazole compounds having an excellent antitumor activity by chemically modifying BE-13793C, and disclosed them (refer to PCT/WO91/18003).

For the purpose of creating compounds having a further excellent antitumor activity by chemically modifying previously disclosed indolopyrrolocarbazole antitumor compounds, the present inventors synthesized many indolopyrrolocarbazole derivatives, investigated their antitumor activity, and as a result, now, found that a series of compounds represented by the following general formula are novel compounds having an extremely excellent antitumor activity.

Thus, this invention provides indolopyrrolocarbazole derivatives represented by the following general formula and pharmaceutically acceptable salts thereof.

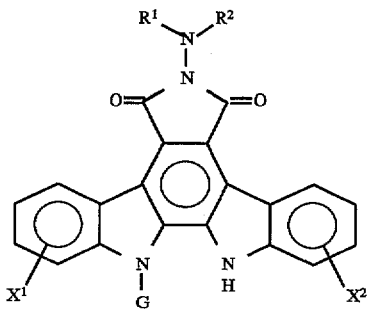

[I]

wherein $R^1$ and $R^2$ each independently represent a hydrogen atom, lower alkyl group, lower alkenyl group, lower alkynyl group, aryl group, aralkyl group or heterocyclic group (the lower alkyl group, lower alkenyl group, lower alkynyl group, aryl group, aralkyl group and heterocyclic group may each have 1 to 5 substituents selected from the group consisting of carboxyl groups, carbamoyl groups, sulfo groups, amino groups, cyano groups, mono-lower alkylamino groups, di-lower alkylamino groups, hydroxyl groups and halogen atoms), or a group of the formula —Y—$R^3$, and therein Y represents a carbonyl group, thiocarbonyl group or sulfonyl group, and $R^3$ represents a hydrogen atom, lower alkyl group, cycloalkyl group, cycloalkylalkyl group, aryl group, aralkyl group, lower alkoxy group, hydrazino group, amino group, arylamino group, carbamoyl group or heterocyclic group (the lower alkyl group, cycloalkyl group, cycloalkylalkyl group, aryl group, aralkyl group and heterocyclic group may each have 1 to 4 substituents selected from the group consisting of halogen atoms, optionally protected hydroxyl groups, amino groups, carboxyl groups, carbamoyl groups, cyano groups and lower alkoxycarbonyl groups, and the amino group and carbamoyl group may each be mono- or di-substituted by lower alkyl group(s) optionally substituted by substituent(s) selected from the group consisting of halogen atoms, hydroxyl groups, amino groups, carboxyl groups, carbamoyl groups and lower alkoxycarbonyl groups); or $R^1$ and $R^2$ combine to represent a lower alkylidene group (the lower alkylidene group may have 1 to 4 substituents selected from the group consisting of amino groups, mono-lower alkylamino groups, di-lower alkylamino groups, hydroxyl groups, carboxyl groups and sulfonyl groups); or $R^1$ and $R^2$ combine together with the nitrogen atom to which they bind to form a heterocyclic group (the heterocyclic group may have on the ring lower alkyl group(s) optionally substituted by group(s) selected from the group consisting of amino groups, hydroxyl groups, a carboxyl groups and sulfo groups), G represents a pentose group or hexose group, and $X^1$ and $X^2$ each independently represent a hydrogen atom, halogen atom, amino group, mono-lower alkylamino group, di-lower alkylamino group, hydroxyl group, lower alkoxy group, aralkoxy group, carboxyl group, lower alkoxycarbonyl group or lower alkyl group.

The term of "lower" used in the present invention means that the carbon number of the group or compound to which this term is attached is 6 or less, preferably 4 or less.

The "lower alkyl group" is a straight-chain or branched chain alkyl group having 1 to 6 carbon atoms, and examples thereof are a methyl group, an ethyl group, a propyl group, an isopropyl group, a butyl group, an isobutyl group, a sec-butyl group, a tert-butyl group, a pentyl group, an isopentyl group, a neopentyl group, a hexyl group, etc.

The "lower alkenyl group" includes a straight-chain or branched chain alkenyl group having 3 to 6 carbon atoms, and examples thereof are a propenyl group, a 2-butenyl group, a 3-butenyl group, a 3-pentenyl group, a 4-hexenyl group, etc.

The "lower alkynyl group" can be a straight-chain or branched chain alkynyl group having 3 to 6 carbon atoms, and examples thereof are a propynyl group, a 2-butynyl group, a 3-butynyl group, a 3-pentynyl group, a 4-hexynyl group, etc.

The "cycloalkyl group" includes a 3- to 6-membered cycloalkyl group, and examples thereof are a cyclopropyl group, a cyclobutyl group, a cyclopentyl group, a cyclohexyl group, etc.

The "cycloalkyl lower alkyl group" means an alkyl group substituted by a cycloalkyl group wherein the cycloalkyl and lower alkyl parts have the above meanings, respectively, and examples thereof are a cyclopropylmethyl group, a cyclobutylmethyl group, a cyclopentylmethyl group, a cyclohexyl-methyl group, a 1-cyclopropylethyl group, a 2-cyclopropylethyl group, a 1-cyclobutylethyl group, a 2-cyclobutylethyl group, a 1-cyclopentylethyl group, a 2-cyclopentylethyl group, a 1-cyclohexylethyl group, a 3-cyclohexylpropyl group, a 3-cyclopentylpropyl group, a 4-cyclohexylbutyl group, a 4-cyclopentylbutyl group, etc., and preferably, the cycloalkylalkyl group has 4 to 10 carbon atoms in total.

The "aryl group" can be monocyclic or polycyclic, and aryl groups having 6 to 12 carbon atoms can be mentioned such as a phenyl group, a naphthyl group and a tetrahydronaphthyl group.

The "aralkyl" group means a lower alkyl group substituted by an aryl group wherein the aryl and lower alkyl parts have the above meanings, respectively, and aralkyl groups having 7 to 15 carbon atoms can be mentioned such as, for example, a benzyl group, a phenethyl group, a phenylpropyl group, a phenylbutyl group, a phenylpentyl group, a naphthylmethyl group and a naphthylethyl group.

The "heterocyclic group" includes a 5- or 6-membered heterocyclic group containing 1 to 4 hetero atoms selected from the group consisting of nitrogen atoms, oxygen atoms and sulfur atoms, and there can be mentioned aromatic heterocyclic groups such as, for example, a pyrrolyl group, a furyl group, a thienyl group, an oxazolyl group, an isoxazolyl group, a thiazolyl group, an isothiazolyl group, an imidazolyl group, a pyrazolyl group, an oxadiazolyl group, a thiadiazolyl group, a triazolyl group, a tetrazolyl group, a furazanyl group, a pyridyl group, a pyridazinyl group, a pyrimidinyl group, a pyrazinyl group and a triazinyl group; and nonaromatic heterocyclic groups such as, for example, a dihydrothienyl group, a tetrahydrothienyl group, a pyrrolinyl group, a pyrrolidinyl group, an imidazolidinyl group, an imidazolinyl group, a piperidinol group, a piperazinyl group, an oxazolinyl group, an oxazolidinyl group, an isoxazolinyl group, an isoxazolidinyl group, a thiazolinyl group, a thiazolidinyl group, an isothiazolinyl group, an isothiazolidinyl group, a 1,2-dithiolanyl group, a 1,3-dithiolanyl group, a 1,2-dithiolyl, a 1,3-dithiolyl group, a dihydrothiopyranyl group, a tetrahydrothiopyranyl group, a 1,4-dithianyl group, a 1,4-dithiinyl group, a 1,4-oxathiinyl group and a thiomorpholinyl group.

As the "mono-lower alkylamino groups", there can, for example, be mentioned a methylamino group, an ethylamino group, a propylamino group, an isopropylamino group, a butylamino group, a pentylamino group, a hexylamino group, etc., and as the "di-lower alkylamino groups" there can, for example, be mentioned a dimethylamino group, an ethylmethylamino group, a diethylamino group, an ethylpropylamino group, a dipropylamino group, a butylmethylamino group, a dibutylamino group, a butylethylamino group, a methylpentylamino group, a hexylmethylamino group, an ethylhexylamino group, etc.

The "arylamino group" means an amino group substituted by an aryl group wherein the aryl part has the above meanings, and the arylamino group can be mentioned such as, for example, a phenylamino group and a naphthylamino group.

The "halogen atoms" include a fluorine atom, a chlorine atom, a bromine atom and an iodine atom.

As the "lower alkylidene groups", there can be mentioned straight-chain or branched alkylidene groups having 1 to 6 carbon atoms such as, for example, a methylene group, an ethylidene group, a propylidene group, an isopropylidene group, a butylidene group, an isobutylidene group, a sec-butylidene group, a pentylidene group, an isopentylidene group, a neopentylidene group and a hexylidene group.

The "lower alkoxy group" means a (lower alkyl)-O-group wherein the lower alkyl part has the above meaning, and examples thereof are a methoxy group, an ethoxy group, a propoxy group, an isopropoxy group, a butoxy group, an isobutoxy group, a sec-butoxy group, a tert-butoxy group, a pentoxy group, an isopentoxy group, a neopentoxy group, a hexoxy group, etc.

The "lower alkoxycarbonyl group" means a (lower alkoxy)-CO-group wherein the lower alkoxy part has the above meaning, and examples thereof are a methoxycarbonyl group, an ethoxycarbonyl group, a propyloxycarbonyl group, an isopropyloxycarbonyl group, a butyloxycarbonyl group, an isobutyloxycarbonyl group, a pentyloxycarbonyl group, a hexyloxycarbonyl group, etc.

The "aralkoxy group" means a lower alkoxy group substituted by an aryl group wherein the aryl and lower alkoxy parts have the aforesaid meanings, respectively, and examples thereof are a benzyloxy group, a phenethyloxy group, a phenylpropoxy group, an α-naphthylmethoxy group, a β-naphthylmethoxy group, a naphthylethoxy group, a tetrahydronaphthylmethoxy group, etc.

Mentioned as examples of the protective group in the "optionally substituted hydroxyl group" are alkanoyl groups having 2 to 6 carbon atoms such as an acetyl group, a propronyl group and a butyryl group; aroyl groups such as a benzoyl group; substituted or unsubstituted aralkyl groups such as a benzyl group and a 4-methoxybenzyl group; groups forming an acetal such as acetonide; etc.

The "pentose group" and "hexose group" mean a pentose group and a hexose group the hydroxyl groups of which may be substituted by the same or different 1 to 3 groups selected from the group consisting of hydrogen atoms, lower alkyl groups, lower alkylcarbonyloxy groups, lower alkoxy groups and amino groups, or oxidized, and there can be mentioned groups derived from pentoses such as, for example, ribose, arabinose, xylose and 2-deoxyribose, and groups derived from hexoses such as, for example, allose, glucose, mannose, galactose, glucosamine, galactosamine, 2-deoxyglucose, 4-O-methylglucose, rhamnose and glucuronic acid.

Preferred among the compounds of the aforesaid formula [I] provided by this invention are compounds represented by the following formula

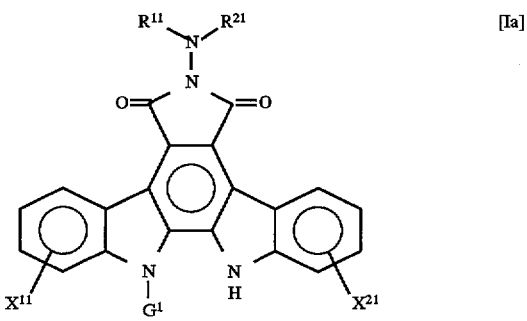

wherein $R^{11}$ and $R^{21}$ each independently represent a hydrogen atom, lower alkyl group, lower alkenyl group, aryl group, aralkyl group, pyrrolyl group, oxazolyl group, isoxazolyl group, thiazolyl group, imidazolyl group, pyridyl group, pyrimidinyl group, oxazolinyl group, oxazolidinyl group, imidazolinyl group, imidazolidinyl group, pyrrolidinyl group, piperazinyl group, thiazinyl group, thiazolidinyl group (the lower alkyl group, lower alkenyl group, aryl group, aralkyl group and heterocyclic group may have 1 to 5 substituents selected from the group consisting of carboxyl groups, carbamoyl groups, cyano groups and hydroxyl groups), or a group of the formula —Y—$R^{31}$, and therein Y represents a carbonyl group, thiocarbonyl group or sulfonyl group, and $R^{31}$ represents a hydrogen atom, lower alkyl group, aryl group (the lower alkyl group and aryl group may have 1 to 4 substituents selected from the group consisting of halogen atoms, optionally protected hydroxyl groups, amino groups and carboxyl groups), amino group, hydrazino group, arylamino group, lower alkoxy group, carbamoyl group, pyrrolyl group, oxazolyl group, isoxazolyl group, thiazolyl group, imidazolyl group, pyridyl group, pyrimidinyl group, oxazolinyl group, oxazolidinyl group, imidazolinyl group, imidazolidinyl group, pyrrolidinyl group, piperazinyl group, thiazinyl group or thiazolidinyl group; or $R^{11}$ and $R^{21}$ combine to represent a lower alkylidene group optionally having carboxyl group(s), or $R^{11}$ and $R^{21}$ combine together with the nitrogen atom to which they bind to form a pyrrolidinyl group, imidazolidinyl group, imidazolinyl group, piperidino group or, piperazinyl group (these heterocyclic groups may have on the ring lower alkyl group(s) optionally substituted by hydroxy group(s)), $G^1$ represents a group of the formula

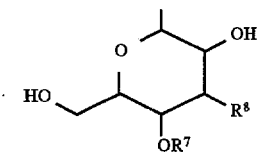

or

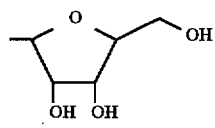

and therein $R^7$ represents a hydrogen atom or lower alkyl group and $R^8$ represents a hydroxyl group or amino group, and $X^{11}$ and $X^{21}$ bind to the indolopyrrolocarbazole rings at the 1- or 2-position and at the 10- or 11-position, respectively, and each independently represent a halogen atom, hydroxyl group, lower alkoxy group or aralkoxy group.

Further preferred compounds are those represented by the following formula

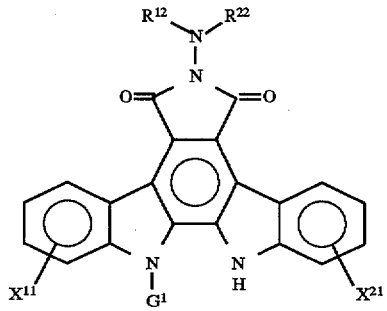

wherein $R^{12}$ represents a hydrogen atom or lower alkyl group, $R^{22}$ represents a hydrogen atom, lower alkyl group (the lower alkyl group may have 1 to 5 substituents selected from the group consisting of carboxyl groups, carbamoyl groups, hydroxyl groups and cyano groups), aryl group, aralkyl group (the aryl group and aralkyl group may have 1 to 4 substituents selected from the group consisting of hydroxyl groups and carboxyl groups), pyridyl group, imidazolyl group, imidazolinyl group, thiazolyl group, pyrrolidinyl group, piperazinyl group, or a group of the formula —Y—$R^{32}$, and therein Y represents a carbonyl group, thiocarbonyl group or sulfonyl group, and when Y is a carbonyl group or thiocarbonyl group, $R^{32}$ represents a hydrogen atom, lower alkyl group, aryl group (the lower alkyl group and aryl group may have 1 to 4 substituents selected from the group consisting of halogen atoms, optionally protected hydroxyl groups, amino groups and carboxyl groups), amino group, hydrazino group, arylamino group, lower alkoxy group, carbamoyl group, pyridyl group, pyrimidinyl group, imidazolinyl group or pyrrolidinyl group, and when Y is a sulfonyl group, $R^{32}$ represents a lower alkyl group or aryl group; or $R^{12}$ and $R^{22}$ combine to represent a lower alkylidene group having carboxyl group(s); or $R^{12}$ and $R^{22}$ combine together with the nitrogen atom to which they bind to form a pyrrolidinyl group, piperidino group or piperazinyl group (these heterocyclic groups may have on the ring lower alkyl group(s) optionally having hydroxyl group(s)), and $G^1$, $X^{11}$ and $X^{21}$ have the same meanings as defined in the above formula [Ia].

Preferred as $G^1$ is generally

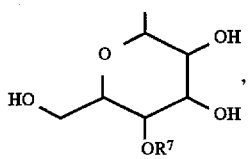

and preferred as $X^{11}$ and $X^{21}$ are hydroxyl groups bound to the 1-position and 11-position of the indolopyrrolocarbazole ring, respectively.

An especially preferred class of compounds of formula [Ib] are those in which $R^{22}$ represents the lower alkyl ($C_1$–$C_6$) group substituted with up to five hydroxyl groups. Further preferred are those wherein $X^{11}$ and $X^{21}$ each represent a hydroxyl group, especially those in which the hydroxyl groups are positioned at the 1- and 11-positions or at the 2- and 10-positions of the indolopyrrolocarbazole rings.

An especially preferred class of compounds within the scope of formula [I] and formula [Ib] are those represented by the following formula

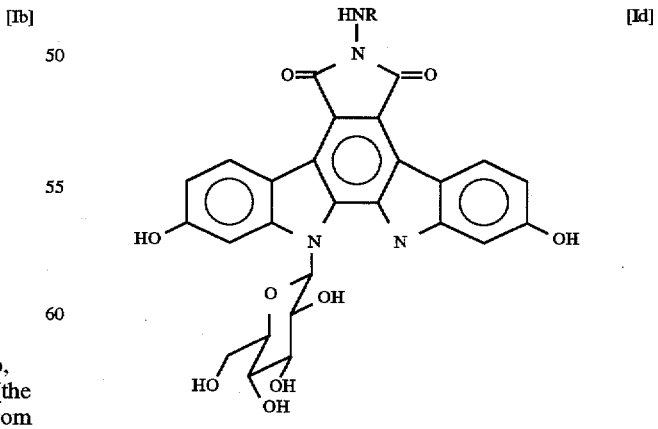

wherein R represents a branched or straight chain alkyl group of 2 to 5 carbon atoms containing 1 to 4 hydroxyl groups.

Preferred as R are branched or straight-chain alkyl groups of 2 or 3 carbon atoms containing 1 or 2 hydroxyl groups, such as, for example, —CH$_2$CH$_2$OH, —CH$_2$CH(OH)CH$_2$OH, —CH(CH$_2$OH)$_2$ and the like.

The compounds of this Invention can exist in the form of pharmaceutical acceptable salts. Such salts include addition salts with inorganic acids such as, for example, hydrochloric acid and sulfuric acid, and with organic acids such as, for example, acetic acid, citric acid, tartaric acid and maleic acid. Further, in case the compounds of this invention contain an acidic group, the acidic group can exist in the form of alkali metal salts such as, for example, a potassium salt and a sodium salt; alkaline earth metal salts such as, for example, a magnesium salt and a calcium salt; and salts with organic bases such as an ethylamine salt and an arginine salt.

A compound of the formula [I] set forth in this invention can be prepared by reacting a compound represented by the following formula or a derivative thereof wherein the functional groups are protected

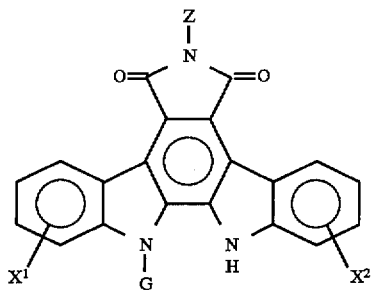

[II]

or

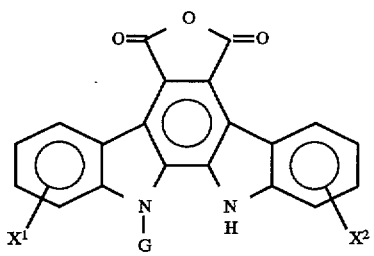

[III]

wherein,

Z represents a hydrogen atom or substituted or unsubstituted lower alkyl group, and $X^1$, $X^2$ and G have the same meanings as defined above with a compound represented by the following general formula or a derivative thereof wherein in case $R^{13}$ and $R^{23}$ contain a functional group, the functional group is each protected

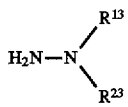

[IV]

wherein $R^{13}$ and $R^{23}$ each independently represent a hydrogen atom, lower alkyl group, lower alkenyl group, lower alkynyl group, aryl group, aralkyl group or heterocyclic group (the lower alkyl group, lower alkenyl group, lower alkynyl group, aryl group, aralkyl group and heterocyclic group may have 1 to 5 substituents selected from the group consisting of carboxyl groups, carbamoyl groups, sulfo groups, amino groups, cyano groups, mono-lower alkylamino groups, di-lower alkylamino groups, hydroxyl groups and halogen atoms), or a group of the formula —Y—$R^3$, and herein Y represents a carbonyl group, thiocarbonyl group or sulfonyl group, and $R^3$ represents a hydrogen atom, lower alkyl group, cycloalkyl group, cycloalkylalkyl group, aryl group, aralkyl group, lower alkoxy group, hydrazino group, amino group, arylamino group, or carbamoyl group or heterocyclic group (the lower alkyl group, cycloalkyl group, cycloalkylalkyl group, aryl group, aralkyl group and heterocyclic group may each have 1 to 4 substituents selected from the group consisting of halogen atoms, optionally protected hydroxyl groups, amino groups, carboxyl groups, carbamoyl groups, cyano groups and lower alkoxycarbonyl groups, and the amino group and carbamoyl group may each be mono- or di-substituted by lower alkyl group(s) optionally substituted by group(s) selected from the group consisting of halogen atoms, hydroxyl groups, amino groups, carboxyl groups, carbamoyl groups and lower alkoxycarbonyl groups); or $R^{13}$ and $R^{23}$ combine together with the nitrogen atom to which they bind to form a heterocyclic group (the heterocyclic group may have on the ring lower alkyl group(s) optionally substituted by group(s) selected from the group consisting of amino groups, hydroxyl groups, carboxyl groups and sulfo groups); if necessary, removing the protective group(s) existing in the product to prepare a compound represented by the general formula

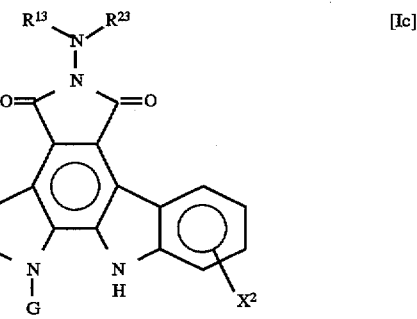

[Ic]

wherein $R^{13}$, $R^{23}$, $X^1$, $X^2$, G have the same meanings as defined above;

or either formylating, alkylating, alkenylating, alkynylating, aralkylating, carbamoylating, thiocarbamoylating, alkanoylating or sulfonylating the amino group

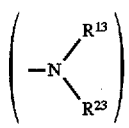

of the compound of the above formula [Ic] or the derivative thereof wherein the functional groups are protected when $R^{13}$ and $R^{23}$ represent a hydrogen atom, or condensing the above compound or derivative with a compound represented by the following formula or a derivative thereof wherein a functional group is protected

OHC—$R^6$ [V]

wherein $R^6$ represents a hydrogen atom or carboxyl group, or a lower alkyl group optionally having 1 to 4 substituents selected from the group consisting of amino groups, mono- lower alkylamino groups, di-lower alkylamino groups, hydroxyl groups, carboxyl groups and sulfo groups, and if necessary, removing the protective groups existing in the product; or reducing the double bonds of the compound of the above formula [Ic] when $R^{13}$ and/or $R^{23}$ contain a double bond or the compound prepared by condensing the compound [Ic] and the compound [V], or the derivative thereof wherein the functional groups are protected, and if necessary removing the protective groups existing in the product; and if necessary, converting the resulting compound of the formula [I] into a pharmaceutically acceptable salt.

Herein, the terms of alkylation, alkenylation, alkynylation, aralkylation, alkanoylation and sulfonylation are widely interpreted, and mean all of the reactions to introduce substituents corresponding to $R^1$ and $R^2$ in the structure of the compounds of this invention, and for example, alkylation means introduction of a substituted or unsubstituted alkyl group included in this invention.

Reaction of a compound of the formula [II] or [III] (hereafter, including a derivative thereof wherein a functional group is introduced) with a compound of the formula [IV] (hereafter, including a derivative thereof wherein its functional groups are protected) can be carried out in accordance with reaction known per se of an imide or acid anhydride with a hydrazine or a hydrazine derivative, and can, for example, be carried out in the absence of a solvent or in an inert solvent, for example a solvent such as N,N-dimethylformamide at a temperature between about 0° C. and the boiling point of the solvent, preferably in the range of about room temperature to about 80° C.

The use quantity of the compound of the formula [IV] to the compound of the formula [II] or [III] is not particularly limited, and can be varied over a wide range according to the kind of the compound, reaction conditions, etc., but usually, it is suitable to use the compound of the formula [IV] in a quantity in the range of at least 1 mole, preferably 1 to 10 moles, particularly 3 to 5 moles per mole of the compound of the formula [II] or [III]. Further, when the compound of the formula [IV] is liquid in the reaction temperature, it is also possible to use the compound in a largely excessive quantity, for example in a rate of 10 to 40 moles per mole of the compound of the formula [II] or [III] so as to make it serve as a solvent.

Thereby, there can be obtained a compound of the above formula [Ic] wherein the existing functional groups are sometimes protected appropriately.

The thus obtained compound of the formula [Ic] in case $R^{13}$ and $R^{23}$ represent a hydrogen atom or a derivative thereof wherein its functional groups are protected (hereafter, generally referred to as a compound of [Ic-1]) can be formylated, alkylated, alkenylated, alkynylated, aralkylated, carbamoylated, thiocarbamoylated, alkanoylated or sulfonylated to give a corresponding compound of the formula [Ic] in case at least one of $R^{13}$ and $R^{23}$ represents a group except for a hydrogen atom defined on these groups.

Formylation of a compound of the formula [Ic-1] can be carried out according to a method usually used in formylation of an amino group, and can, for example, be carried out by heating it together with formic acid, formamide, dimethylformamide or the like, or by a method to react it with a mixture of formic acid and an acid anhydride in a solvent having no bad influence or without any solvent, or by another means.

Reaction of the compound of the formula [Ic-1] with formic acid, formamide, dimethylformamide or the like is usually carried out at a temperature in the range of 30° C. to the boiling point of the solvent, but if necessary, can also be carried out at a temperature above or under such temperature, and reaction time is usually in the range of 30 minutes to 2 days. Preferably, the reaction is carried out usually in the presence of an acid catalyst such as hydrochloric acid or sulfuric acid.

Formylation using a mixture of formic acid with an acid anhydride is usually carried out at a comparatively low temperature in the range of −5° C. to room temperature, but can, if necessary, be carried out in a range above or under this. Further, reaction time is usually 10 minutes to 5 hours, but can, if necessary, be lengthened or shortened.

Alkylation, alkenylation, alkynylation and aralkylation of a compound of the formula [Ic-1] can be carried out in accordance with a method known per se, for example, reaction with an alkylating agent, alkenylating agent, alkynylating agent or aralkylating agent such as an alkyl halide, an alkenyl halide, an alkynyl halide, an aralkyl halide, an alkyl mesylate, an alkenyl mesylate, an aralkyl mesylate, an alkyl tosylate or an aralkyl tosylate; or a method to condense it with an aldehyde compound or a ketone compound and reduce the resultant condensate; or the like. The reduction reaction at that time can be carried out according to a method using formic acid, a metal or a metal hydride or a usual method such as a catalytic reduction method using palladium-carbon or the like.

Carbamoylation and thiocarbamoylation of a compound of the formula [Ic-1] can be carried out by reacting it with a correspond isocyanate compound or thioisocyanate compound in the absence of solvent or in a suitable solvent. Reaction temperature can be in the range of about −20° C. to the boiling point of the solvent, preferably about 0° to about 50° C.

Alkanoylation of a compound of the formula [Ic-1] can be carried out by a method to react it with a corresponding acid halide or an acid anhydride in the absence of a solvent or in a suitable solvent. Reaction can usually be carried out at a temperature in the range of about −5° C. to the boiling point of the solvent, and if necessary, can also be carried out at a temperature below this.

The acid halide or acid anhydride is, usually, used in a rate of small excess to the compound of the formula [Ic-1], but can, if necessary, be used in a quantity below or above this, and reaction time can, usually, be 30 minutes to 2 days.

Sulfonylation of a compound of the formula [Ic-1] can be carried out by reacting it with a reagent such as a corresponding organic sulfonic acid anhydride or organic sulfonyl halide in the presence or absence of a base. Reaction temperature can, usually, be sufficient in the range of about −10° C. to about 50° C., but can, if necessary, be a temperature above or under this, and reaction time can, usually, be 30 minutes to 3 days. A reagent such as an organic sulfonic acid anhydride or an organic sulfonyl halide is, usually, used in a rate of small excess, but can also be used, in a quantity above or under this.

Further, condensation reaction of a compound of the formula [Ic-1] with a compound of the above formula [V] (including a derivative thereof wherein the functional groups are protected) is so-called Schiff base formation reaction, and can, for example, usually be carried out in a solvent inert to the reaction, e.g. in a solvent such as tetrahydrofuran, at a temperature between about 0° C. to the boiling point of the solvent, preferably in the range of room temperature to about 50° C. Reaction time is usually in the range of 30 minutes to 2 days, but can, if necessary, be a time above or under this.

Use quantity of the compound of the formula [V] to the compound of the formula [Ic-1] is not strictly limited, but usually, it is suitable to use the compound of the formula [V] in a rate of 1 to 50 moles, particularly 3 to 10 moles per mole of the compound of the formula [Ic-1].

The hydrazone compound obtained by the above reaction can be subjected to usual catalytic hydrogenation reaction using palladium-carbon or the like to give a compound of the formula [I] wherein $R^1$ or $R^2$ represents a hydrogen atom.

In the foregoing processes, protection of functional groups in raw material compounds and removal of protective groups existing in the formed compounds can be carried out using usual and optional methods widely known in the chemical field.

Further, isolation and purification of compounds produced by the above reactions can be carried out according to methods known per se in the field of organic synthetic chemistry, for example precipitation methods, solvent extraction methods, recrystallization, chromatography, etc.

A compound of the above formula [II] used as a starting raw material in the aforesaid processes can be prepared by glycosidating a compound represented by the general formula

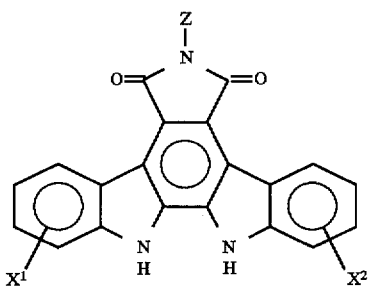

wherein $X^1$, $X^2$ and Z have the same meanings as defined above
prepared by a process known per se [refer to J. Chem. Soc. Perkin Transactions I. pp 2475–2480 (1990)] or a derivative thereof wherein the functional groups are protected.

Glycosidation of the compound of the formula [VI] or the derivative thereof wherein the functional groups are protected can be carried out by a process known per se [refer to J. Am. Chem. Soc. 60, 2559 (1938)], for example by condensing it with a reactive derivative of a pentose or hexose wherein the hydroxyl groups are protected, e.g. 1-bromo-2,3,4,6-O-tetraacetylglucose, using as an activating agent mercury cyanide, silver carbonate, silver oxide or the like, preferably silver oxide, in an aprotic solvent, e.g. a solvent such as benzene, toluene or methylene chloride at a temperature of about 0° C. to about 100° C., preferably about 80° C.

Alternatively, a compound of the formula [II] can also be prepared according to the process disclosed in the aforesaid PCT/WO91/18003.

Further, a compound of the formula [III] can be prepared by treating with a base a thus obtained compound of the formula [II] or derivative thereof wherein the functional groups are protected.

Preferred as the base is an aqueous solution of potassium hydroxide, and treatment with this base can usually be carried out at room temperature, but in some cases can also be carried out with heating up to a temperature of about 50° C.

Neutralization or acidification of the reaction mixture can, if necessary, be carried out using hydrochloric acid, and thereby it is possible to precipitate the compound of the formula [III] as crystals.

The compounds of formula [II] in which G represents a glycosyl group of formula

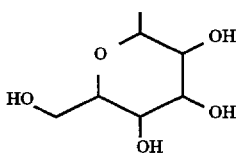

(these glycosyl group containing compounds may be referred to as compounds of formula [VII]) may, preferably, be prepared by a fermentation culturing reaction of a compound of the general formula

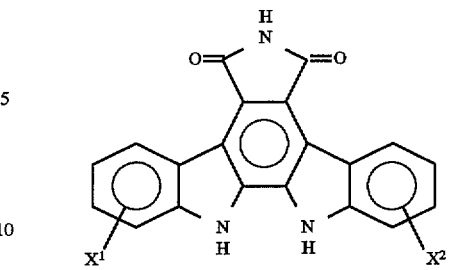

as described in detail in commonly assigned prior copending application Ser. No. 08/068,097 filed May 28, 1993, on pages 20–25 and in Examples C and D, the entire disclosure of which is incorporated herein in its entirety by reference thereto.

The compounds of the formula [I] provided by this invention have an excellent antitumor action as shown in the following pharmacological test examples.

(1) Therapeutic effect against mouse tumor (P388)

Therapeutic effect of the compounds of this invention against mouse tumor (P388) is shown in Tables 1 and 2.

TABLE I

Effect of the compound of Example 2 against P388

| Tumor[1] | Dose[2], i.p (mg/kg/injection) | MST[3](day) | T/C (%)[4] |
|---|---|---|---|
| P388 | 0 | 12.3 ± 1.06 | 100 |
|  | 1 | 15.8 ± 0.84 | 128 |
|  | 3 | 17.8 ± 1.92 | 145 |
|  | 10 | >26.4 ± 18.82 | >245 |
|  | 30 | >42.2 ± 24.38 | >343 |
|  | 100 | >47.2 ± 18.90 | >384 |

TABLE 2

Effect of the compound of Example 5 against P388

| Tumor[1] | Dose[2], i.p (mg/kg/injection) | MST[3](day) | T/C (%)[4] |
|---|---|---|---|
| P388 | 0 | 12.3 ± 0.95 | 100 |
|  | 1 | 16.8 ± 0.84 | 137 |
|  | 3 | 17.8 ± 1.92 | 145 |
|  | 10 | >26.2 ± 10.18 | >213 |
|  | 30 | >23.4 ± 9.74 | >190 |
|  | 100 | >36.4 ± 8.05 | >296 |

(Footnotes of Tables 1 and 2)
[1]Tumor inoculation: $10^6$ cancer cells were intraperitoneally inoculated.
[2]Dose: After tumor inoculation, each dose was intraperitoneally administered once a day from the 1st day to 10th day.
[3]MST: mean survival number of days
[4]T/C (%): (MST of treatment group/MST of control) × 100
[5]Standard: in case of T/C ≧ 125, the test compound was judged to have a remarkable antitumor effect in the dose.

(2) Proliferation inhibition activity against mouse leukemia cell

Measurement method:

100 μl portions of a cell culturing medium (10% fetal bovine serum-containing-RPMI-1640 medium) containing $3 \times 10^3$ mouse leukemia cell (P388) were put in a 96-hole microplate, the cells were cultured under 5% $CO_2$ at 37° C. for 24 hours, 10 μl each of test solutions containing test compounds respectively were added respectively, and the cells were further cultured under 5% $CO_2$ at 37° C. for 24 hours. 10 μl portions of 0.5% Thiazoyl Blue were added to the culture broths, and incubation was carried out under 5% $CO_2$ at 37° C. for 2 hours to carry out enzymatic reaction.

20% sodium dodecyl sulfate (SDS) was added to discontinue the reaction, incubation was further carried out at 37° C. for 4 hours to dissolve the formed dye, and absorbance at 550 nm was measured and compared with the control group. The results are shown in Table 3.

TABLE 3

| Proliferation inhibition activity against mouse leukemia cell P388 | |
|---|---|
| Test compound | 50% inhibitory concentration (IC$_{50}$, µM) |
| Compound of Example 1 | <0.030 |
| Compound of Example 2 | 0.29 |
| Compound of Example 3 | 0.065 |
| Compound of Example 4 | 0.096 |
| Compound of Example 5 | 0.28 |
| Compound of Example 6 | 0.059 |
| Compound of Example 7 | 0.091 |
| Compound of Example 8 | 0.30 |
| Compound of Example 9 | 0.028 |
| Compound of Example 10 | 0.46 |
| Compound of Example 11 | <0.026 |
| Compound of Example 12 | 0.042 |
| Compound of Example 13 | 0.22 |
| Compound of Example 14 | <0.027 |
| Compound of Example 15 | 0.31 |
| Compound of Example 17 | 0.044 |
| Compound of Example 22 | 0.11 |
| Compound of Example 23 | <0.025 |
| Compound of Example 24 | 0.001 |
| Compound of Example 25 | 0.048 |
| Compound of Example 27 | 0.027 |
| Compound of Example 28 | <0.029 |
| Compound of Example 29 | 0.005 |
| Compound of Example 30 | 0.003 |
| Compound of Example 31 | 0.011 |
| Compound of Example 33 | 0.11 |
| Compound of Example 34 | 0.019 |
| Compound of Example 35 | 0.17 |
| Compound of Example 36 | 0.002 |
| Compound of Example 37 | 0.095 |

As apparent from the results of the above pharmacological test, the compounds of this invention exhibit an excellent antitumor action, and are useful as an antitumor agent for control or prevention of diseases, particularly for treatment of cancers. When a compound of this invention is used in such uses, it is, usually, formulated into a pharmaceutical preparation comprising an effective quantity of it and a pharmaceutically acceptable carrier or diluent.

As administration forms at the time of use of a compound of this invention, various forms can be selected, and there can be mentioned oral agents such as, for example, tablet, capsules, powders, granules or liquids, or sterilized liquid parenteral agents such as, for example solutions or suspensions, or suppositories, ointments, or the like.

Solid preparations can be prepared, as they are, as forms of tablets, capsules, granules or powders, or can also be prepared using suitable additives. Such additives may be additives usually used, and include saccharides such as, for example, lactose and glucose; starches such as, for example, corn, wheat and rice; fatty acids such as, for example, stearic acid; inorganic salts such as, for example, magnesium metasilicate aluminate and anhydrous calcium phosphate; synthesized macromolecules such as, for example, polyvinylpyrrolidone and polyalkylene glycol; fatty acid salts such as, for example, calcium stearate and magnesium stearate; alcohols such as, for example, stearyl alcohol and benzyl alcohol; synthesized cellulose derivatives such as, for example, methylcellulose, carboxymethylcellulose, ethylcellulose and hydroxypropylmethylcellulose; and further, gelatin, talc, vegetable oils, gum arabic, etc.

Solid preparations such as these tablets, capsules, granules and powders contain an effective ingredient generally at 0.1–100 weight %, preferably at 5–100 weight %.

Liquid preparations are prepared in forms such as suspensions, syrups, injections or drops using suitable additives usually used in liquid preparations such as water, alcohols or oils originated in vegetables such as, for example, soybean oil, peanut oil and sesame oil.

Particularly, solvents suitable in case of parenteral administration in the form of intramuscular injection, intravenous injection or subcutaneous injection include, for example, distilled water for injection, aqueous lidocaine hydrochloride solutions (for intramuscular injection), physiological saline, aqueous glucose solutions, ethanol, polyethylene glycol, liquids for intravenous injection (e.g. aqueous solutions of citric acid and sodium citrate, etc.), electrolyte solutions (for intravenous drip and intravenous injection), etc., and their mixed solvents.

These injections can take forms that powder itself or to which suitable additives were added is dissolved at the time of use, besides such forms that ingredients are dissolved in advance. Such an injection contains usually 0.1–10 weight %, preferably 1–5 weight % of the effective ingredient.

Further, a liquid agent of a suspension, syrup or the like for oral administration can usually contain 0.5–10 weight % of the effective ingredient.

The preferred dose of the compounds of this invention can be varied according to the kind of a compound to be used, the kind and application frequency of the compounded composition, the specified site to be treated, the degree of diseases, the age of patients, diagnosis of doctors, the kind of tumor, etc., but, as an approximate standard, the dose per day and per one adult can, for example, be in the range of 10 to 500 mg in case of oral administration, and in the range of 10 to 100 mg in case of parenteral administration, preferably intravenous injection. The administration frequency varies depending on administration methods and symptoms, but is 1 to 5 times a day. Further, there can also be adopted administration methods such as intermittent administration, e.g. every second day administration or every third day administration.

This invention is more specifically described below by examples, but not limited only by these examples.

EXAMPLE A

The compound represented by the formula

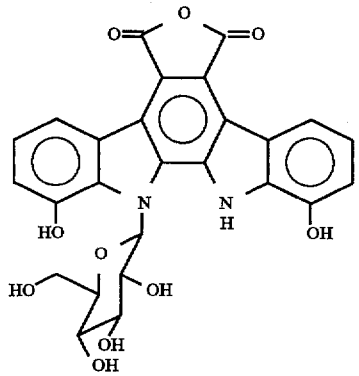

3.4 g of 12,13-dihydro-1,11-dihydroxy-13-(β-D-glucopyranosyl)-5H-indolo[2,3-a]pyrrolo[3,4-c]carbazole-5,7(6H)-dione was dissolved in 120 ml of 10% aqueous potassium hydroxide solution, and the solution was stirred at room temperature for 2 hours. The reaction solution was neutralized with addition of 120 ml of 2N hydrochloric acid, and the precipitated red crystals were filtered, washed with water and dried to give 3.0 g of the captioned compound.

FAB-MS(m/z): 520 (M)$^+$, 521 (M+H)$^+$ $^1$H-NMR (400 MHz, DMSO-d$_6$), δ (ppm): 3.42 (1H,m), 3.56–3.70 (2H,m), 3.76 (1H,m), 3.95–4.10 (2H,m), 4.95 (1H,d,J=4.6 Hz), 5.24 (1H,d,J=5.4 Hz), 5.32 (1H,dd,J=4.9, 5.1 Hz), 7.06 (2H,dd,J=7.6, 7.8 Hz), 7.09 (1H,d,J=8.0 Hz), 7.20 (1H,d,J=7.8 Hz), 7.40 (1H,d,J=7.8 Hz), 8.36 (1H,d,J=7.6Hz), 8.51 (1H,d,J=7.6 Hz), 10.13 (1H,s), 10.52 (1H,s), 11.11 (1H,s)

EXAMPLE B

The compound represented by the formula

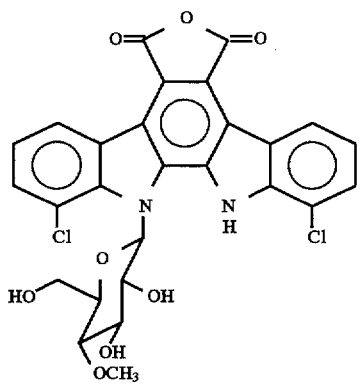

50 mg of rebeccamycin was dissolved in 5 ml of N,N-dimethylformamide, 5 ml of 2N aqueous sodium hydroxide solution was added, and the mixture was stirred at 80° C. for 3 hours. 60 ml of water was added to the reaction solution, the mixture was cooled with ice, and the precipitated yellow precipitate was recovered by filtration. This was subjected to column chromatography on silica gel (inner diameter 1.5 cm, length 45 cm), the column was washed with chloroform, elution was carried out with chloroform-tetrahydrofuran (10:1), and the fraction containing the desired product was concentrated to dryness. The resultant yellow powder was washed with chloroform to give 6.4 mg of the captioned compound.

Rf value: 0.51 (produced by Merck Co., Kiesel gel 60F$_{254}$, developing solvent; chloroform:methanol:tetrahydrofuran:acetic acid=10:1:1:0.2)

FAB-MS(m/z): 571 [M+H]$^+$ $^1$H-NMR (300 MHz, DMSO-d$_6$), δ (ppm): 10.9 (1H,s), 9.07 (1H,d,J=7.8 Hz), 8.92 (1H,d,J=7.8 Hz), 7.78 (2H,t,J=7.8 Hz), 7.53 (1H,d,J=7.8 Hz), 7.50 (1H,d,J=7.8, Hz), 7.03 (1H,d,J=8.9 Hz), 3.96 (2H,m), 3.87 (1H,m), 3.61 (3H,s), 3.54–3.73 (3H,m).

EXAMPLE C

The compound represented by the formula

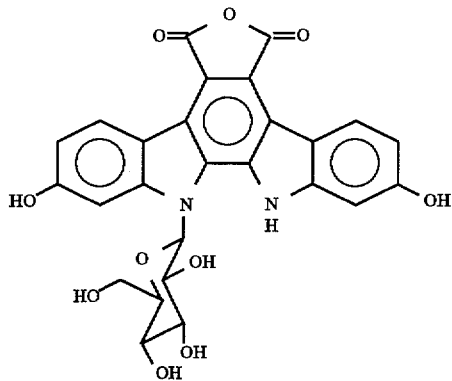

1.3 g of 12,13-dihydro-2,10-dihydroxy-13-(β-D-glucopyranosyl)-6-methyl-5H-indolo(2,3-a)pyrrolo(3,4-c)carbazole-5,7(6H)-dione was dissolved in 40 ml of 10% aqueous potassium hydroxide solution, and the solution was stirred at room temperature for 1 hour. 40 ml of 2N hydrochloric acid was added to the reaction solution to neutralize it, and the mixture was extracted with 1 L of methyl ethyl ketone. The organic layer was washed with saturated saline, dried, and concentrated. The residue was recrystallized from acetone-heptane to give 1.2 g of the captioned compound.

Rf value: 0.40 (produced by Merck Co., Kiesel gel 60 F$_{254}$, developing solvent; toluene:acetonitrile:tetrahydrofuran:water:acetic acid=2:4:2:0.5:0.1)

FAB-MS (m/z): 520 (M)$^+$ $^1$H-NMR (300 MHz, DMSO-d$_6$), δ (ppm): 11.4 (1H, s), 9.95 (1H, s), 9.92 (1H, s), 8.69 (1H, d, J=7.7 Hz), 8.63 (1H, d, J=7.7 Hz), 7.25 (1H, d, J=1.5 Hz), 7.03 (1H, d, J=1.5 Hz), 6.90 (1H, dd, J=7.7 Hz, 1.5 Hz), 6.87 (1H, dd, J=7.7 Hz, 1.5 Hz). 6.06 (1H, d, 8.0 Hz), 5.95 (1H, t, J=4.6 Hz), 5.38 (1H, d, J=5.1 Hz), 5.16 (1H, d, J=5.2 Hz), 4.99 (1H, d, J=5.2 Hz), 3.30–4.10 (6H, m).

EXAMPLE 1

The compound represented by the formula (1)

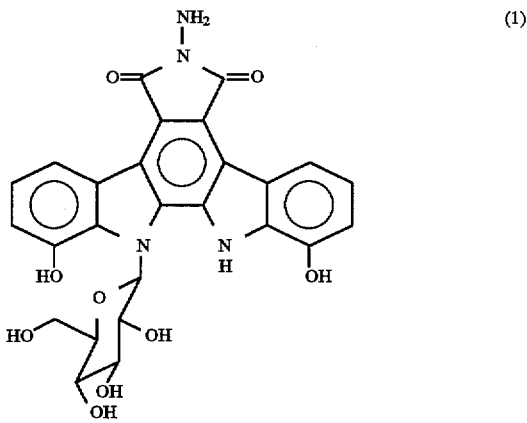

3.51 g of 12,13-dihydro-1,11-dihydroxy-13-(β-D-glucopyranosyl)-5H-indolo[2,3-a]pyrrolo[3,4-c]carbazole-5,7(6H)-dione was dissolved in 8 ml of hydrazine hydrate (Wako Pure Chemical Industries, Ltd.), and reaction was carried out at room temperature for 2 hours. After the reaction, 180 ml of purified water was added, the pH of the solution was adjusted to 5.0 with concentrated hydrochloric acid, the mixture was sufficiently cooled with ice, and the resulting precipitate was collected by filtration, washed with purified water and dried under reduced pressure to give 3.51 g of the captioned compound represented by the formula (1). (yield: 97%)

FAB-MS (m/z): 535 (M+H)⁺

¹H-NMR (400 MHz, DMSO-d₆), δ (ppm): 10.9 (1H, brs), 10.4 (1H, s), 10.0 (1H, s), 8.72 (1H, d, J=7.8 Hz), 8.54 (1H, d, J=7.8 Hz), 7.19 (2H, t, J=7.8 Hz). 7.19 (2H, t, J=7.8 Hz), 7.05 (1H, d, J=9.3 Hz), 7.02 (1H, d, J=7.8 Hz), 7.00 (1H, d, J=7.8 Hz), 5.42 (1H, brd, J=5.8 Hz), 5.35 (1H, brs), 5.22 (1H, brd, J=4.4 Hz), 4.96 (2H, brs), 4.91 (1H, brd, J=5.3 Hz), 4.01 (2H, m), 3.73 (1H, m), 3.63 (2H, m), 3.39 (1H, m)

EXAMPLE 2

The compound represented by the formula

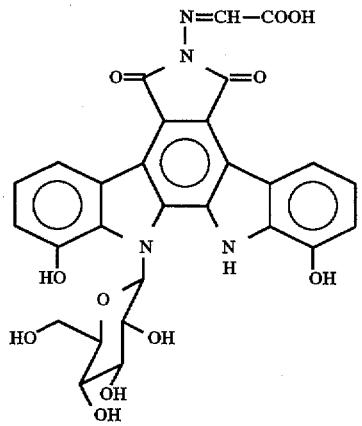

3.47 g of the compound obtained in Example 1 was dissolved in 20 ml of N,N-dimethylformamide (DMF), while the solution was stirred at room temperature, 20 ml of a 100 mg/ml solution of glyoxylic acid (Sigma Co.) was added portionwise, and thereby a precipitate was formed and solidified into a gel-like state. Further, 200 ml of purified water was added, the reaction solution was cooled with ice, and the resultant precipitate was collected by filtration, washed with purified water and dried under reduced pressure to give 3.85 g of the captioned compound represented by the formula (2), (yield: 100%)

FAB-MS (m/z): 591 (M+H)⁺

¹H-NMR (400 MHz, DMSO-d₆), δ (ppm): 11.1 (1H, brs), 10.5 (1H, brs), 10.1 (1H, brs), 9.01 (1H, s), 8.69 (1H, d, J=7.8 Hz), 8.53 (1H, d, J=7.8 Hz), 7.23 (2H, t, J=7.8 Hz), 7.10 (1H, d, J=9.3 Hz), 7.06 (1H, d, J=7.8 Hz), 7.04 (1H, d, J=7.8 Hz), 5.44 (1H, brs), 5.34 (1H, brs), 5.24 (1H, brs), 4.95 (1H, brd, J=5.9 Hz), 4.02 (2H, m), 3.76 (1H, m), 3.64 (2H, m), 3.40 (1H, m)

EXAMPLE 3

The Compound represented by the formula

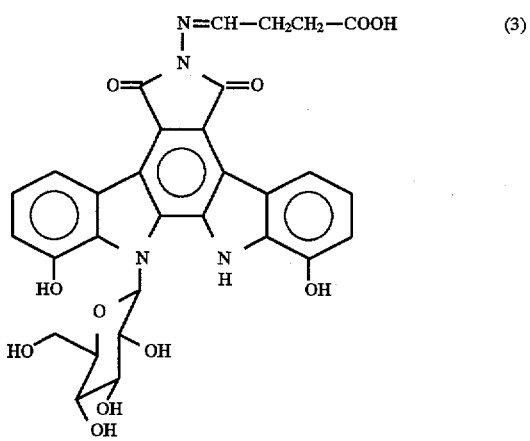

24 mg of the compound obtained in Example 1 was dissolved in 0.5 ml of N,N-dimethylformamide (DMF), while the solution was stirred at room temperature, 0.2 ml of 15% succinic semialdehyde (Aldrich Chemical Co.) was added, and one hour later, 5 ml of purified water was added. After the reaction solution was cooled with ice, and the resultant precipitate was collected by filtration, washed with purified water and dried under reduced pressure to give 25.3 mg of the captioned compound represented by the formula (3). (yield: 91%)

FAB-MS (m/z): 619 (M+H)⁺

¹H-NMR (400 MHz, DMSO-d₆), δ (ppm): 12.1 (1H, brs), 11.0 (1H, brs), 10.4 (1H, brs), 10.0 (1H, brs), 8.69 (1H, brs), 8.68 (1H, d, J=7.8 Hz), 8.51 (1H, d, J=8.3 Hz), 7.19 (2H, t, J=7.8 Hz), 7.07 (1H, d, J=9.3 Hz), 7.04 (1H, d, J=7.8 Hz), 7.01 (1H, d, J=7.8 Hz), 5.43 (1H, brd, J=5.4 Hz), 5.33 (1H, brs), 5.22 (1H, brs), 4.93 (1H, brd, J=4.9 Hz), 4.01 (2H, m), 3.74 (1H, m), 3.63 (2H, m), 3.40 (1H, m)

EXAMPLE 4

The compound represented by the formula

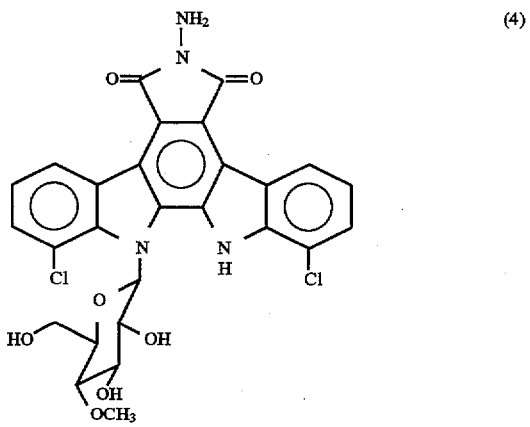

511 mg of rebeccamycin [the compound described in J. Antibiotics 40, 668–678 (1987)] was dissolved in 3 ml of hydrazine hydrate (Wako Pure Chemical Industries, Ltd.), and the solution was allowed to stand at room temperature for one hour. 200 ml of purified water was added, and the resultant precipitate was collected by filtration, washed with 100 ml of purified water and dried under reduced pressure to give 497 mg of the captioned 6-N-aminorebeccamycin represented by the formula (4). (yield: 95%)

FAB-MS (m/z): 585 (M+H)⁺
¹H-NMR (400 MHz, DMSO-d₆), δ (ppm): 10.64 (1H, brs), 9.24 (1H, d, J=7.8 Hz), 9.07 (1H, d, J=7.8 Hz), 7.70 (2H, t, J=7.8 Hz), 7.45 (1H, d, J=7.8 Hz), 7.42 (1H, d, J=7.8 Hz), 6.93 (1H, d, J=8.8 Hz), 5.42 (1H, d, J=5.8 Hz), 5.33 (1H, t, J=5.4 Hz), 5.03 (3H, brs), 3.97 (2H, m), 3.84 (1H, m), 3.59 (3H, s), 3.50–3.70 (3H, m)

EXAMPLE 5

The compound represented by the formula

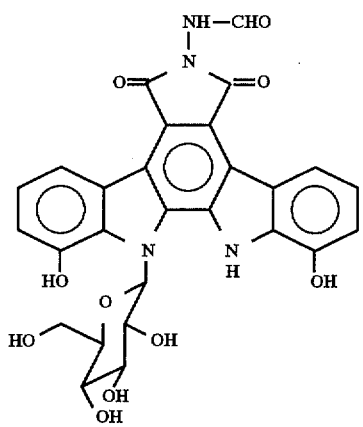

(5)

[Process A]

5 g of the compound obtained in Example 1 was dissolved in 60 ml of N,N-dimethylformamide, 1.8 ml of concentrated hydrochloric acid was added, the mixture was heated at 60° C. for 4 hours, 0.8 ml of concentrated hydrochloric acid was further added, and the mixture was warmed at 37° C. for 16 hours. This was mixed with 1 l of ethyl acetate, the mixture was washed successively with 2% sodium bicarbonate aqueous solution and water, and then the ethyl acetate layer was dehydrated with anhydrous sodium sulfate and concentrated to dryness to give 3.3 g of orange powder. This was dissolved in methanol and subjected to column chromatography on Sephadex LH 20 (inner diameter 3 cm, length 54 cm, eluted with methanol), and the fractions containing the desired product were concentrated to dryness to give 2413.6 mg of the captioned compound represented by the formula (5) as orange powder.

[Process B]

25.9 mg of the compound obtained in Example A was dissolved in 0.5 ml of N,N-dimethylformamide, 15.0 mg of formohydrazide was added, and the mixture was stirred at 70° C. for 2 hours. This was mixed with 70 ml of ethyl acetate, and the mixture was washed with water (20 ml). The ethyl acetate layer was dehydrated with anhydrous sodium sulfate and concentrated to dryness to give 26.9 mg of orange powder. This was dissolved in methanol and subjected to column chromatography on Sephadex LH 20 (inner diameter 1.5 cm, length 48 cm, eluted with methanol), and the fractions containing the desired product were concentrated to dryness to give 16.3 mg of the captioned compound represented by the formula (5) as orange powder.

Rf value: 0.35 (produced by Merck Co., Kiesel gel 60F₂₅₄, developing solvent; chloroform-methanol-tetrahydrofuran=2:1:1)

FAB-MS (m/z): 562 (M)⁺

¹H-NMR (400 MHz, DMSO-d₆), δ (ppm): 11.0 (1H, brs), 10.8 (1H, s), 10.4 (1H, s), 10.0 (1H, s), 8.64 (1H, d, J=8.3 Hz), 8.47 (1H, d, J=8.3 Hz), 8.44 (1H, s), 7.21 (2H, t, J=7.8 Hz), 7.06 (1H, d, J=9.7 Hz), 7.05 (1H, d, J=7.8 Hz), 7.02 (1H, d, J=7.8 Hz), 5.43 (1H, d, J=5.8 Hz), 5.36 (1H, brs), 5.22 (1H, d, J=5.4 Hz), 4.92 (1H, d, J=5.4 Hz), 4.02 (2H, m), 3.75 (1H, m), 3.62 (2H, m), 3.39 (1H, m)

EXAMPLE 6

The compound represented by the formula

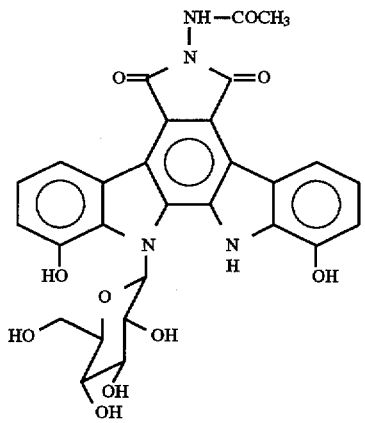

(6)

30 ml of acetic acid and 2 ml of acetic anhydride were added to 510 mg of the compound obtained in Example 1, and the compound was dissolved therein with heating at 90° C. Water was added thereto to make the mixture 300 ml, and the reaction product was adsorbed on a column of Diaion HP 20 (inner diameter 3 cm, length 13.5 cm) and after washing the column with 600 ml of water, eluted with 300 ml of methanol. The methanol eluate was concentrated to dryness, the residue was dissolved in 50 ml of methanol, and the solution was concentrated to about 5 ml. 100 ml of ethyl acetate was added thereto, the mixture was allowed to stand overnight at 4° C., and the resultant orange precipitate was collected by filtration to give 426 mg of the captioned compound represented by the formula (6).

Rf value: 0.43 (produced by Merck Co., Kiesel gel 60F₂₅₄, developing solvent; chloroform-methanol-tetrahydrofuran=2:1:1)

FAB-MS (m/z): 576 (M)⁺

¹H-NMR (400 MHz, DMSO-d₆), δ (ppm): 11.0 (1H, s), 10.7 (1H, s), 10.4 (1H, brs), 10.05 (1H, s), 8.64 (1H, d, J=7.8 Hz), 8.47 (1H, d, J=7.8 Hz), 7.20 (2H, t, J=7.8 Hz), 7.01–7.06 (3H, m), 5.35–5.45 (2H, m), 5.23 (1H, brs), 4.92 (1H, brs), 4.02 (2H, m), 3.74 (1H, m), 3.58–3.70 (2H, m), 3.40 (1H, m), 2.10 (3H, s)

EXAMPLE 7

The compound represented by the formula

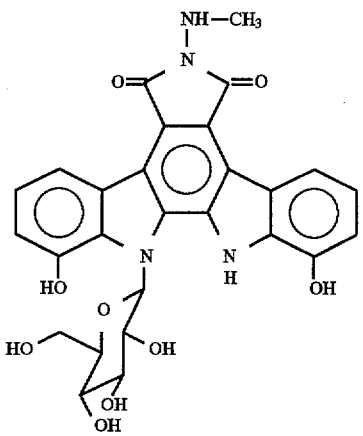

72.5 mg of the compound obtained in Example 1 was dissolved in a mixture of 8 ml of tetrahydrofuran and 5 ml of methanol, 140 μl of 2N hydrochloric acid and 13.2 μl of 37% formaldehyde aqueous solution were added, and the mixture was stirred at room temperature for 2 hours and concentrated to dryness. This was dissolved in 5 ml of N,N-dimethylformamide, 80 mg of 10% palladium carbon, and the mixture was subjected to reduction under hydrogen gas at room temperature for 2 hours and then filtered on Celite. 80 ml of ethyl acetate was added to the resultant filtrate, the mixture was washed successively with 2% sodium bicarbonate aqueous solution and water, and then the resultant ethyl acetate layer was dehydrated and concentrated to dryness to give 28.8 mg of orange powder. This was dissolved in a small quantity of methanol, and the solution was subjected to column chromatography on Sephadex LH-20 (inner diameter 1.5 cm, length 90 cm, eluted with methanol) to give 17.1 mg of the captioned compound represented by the formula (7) as orange powder.

Rf value: 0.49 (produced by Merck Co., Kiesel gel 60F$_{254}$, developing solvent; chloroform-methanol-tetrahydrofuran-acetic acid=20:10:10:1)

FAB-MS (m/z): 549 (M+H)$^+$ $^1$H-NMR (400 MHz, DMSO-d$_6$), δ (ppm): 10.9 (1H, s), 10.4 (1H, s), 9.98 (1H, s), 8.72 (1H, d, J=7.8 Hz), 8.54 (1H, d, J=7.8 Hz), 7.19 (2H, t, J=7.8 Hz), 7.00–7.06 (3H, m), 5.73 (1H, q, J=5.4 Hz), 5.43 (1H, d, J=5.7 Hz), 5.35 (1H, brs), 5.22 (1H, d, J=5.4 Hz), 4.90 (1H, d, J=5.4 Hz), 3.96–4.03 (2H, m), 3.74 (1H, m), 3.58–3.70 (2H, m), 3.40 (1H, m), 2.74 (3H, d, J=5.4 Hz)

EXAMPLE 8

The compound represented by the formula

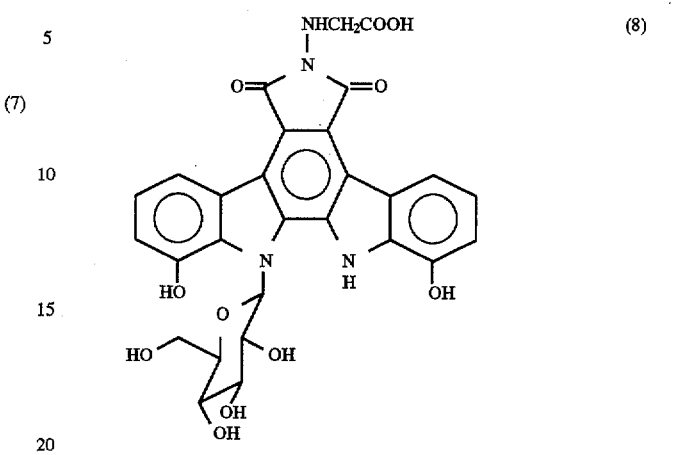

500 mg of the compound obtained in Example 2 was dissolved in 6 ml of N,N-dimethylformamide(DMF), 75 mg of 10% palladium-carbon (Pd-C) was added, and hydrogenation was carried out at room temperature for 3.5 hours under the stirring. The reaction mixture was filtered using filter paper on which diatom earth was spread to remove Pd-C, and 150 ml of water was added to the filtrate. The mixture was adjusted to pH 5 with 1N NaOH, and then extracted with ethyl acetate (200 ml×5). The ethyl acetate layer was concentrated, and the precipitated crystals were collected by filtration to give 182.3 mg of the captioned compound represented by the formula (8).

FAB-MS (m/z): 593 (M+H)$^+$ $^1$H-NMR (400 MHz, DMSO-d$_6$), δ (ppm): 12.6 (1H, brs), 10.9 (1H, s), 10.4 (1H, s), 10.0 (1H, s), 8.69 (1H, d, J=8.3 Hz), 8.52 (1H, d, J=7.8 Hz), 7.18 (2H, t, J=7.8 Hz), 6.99~7.05 (3H, m), 5.90 (1H, brs), 5.42 (1H, d, J=5.4 Hz), 5.35 (1H, t, J=5.4 Hz), 5.21 (1H, d, J=4.9 Hz), 4.89 (1H, d, J=5.4 Hz), 4.03 (2H, m), 3.83 (2H, s), 3.74 (1H, m), 3.63 (2H, m), 3.39 (1H, m)

EXAMPLE 9

The compound represented by the formula

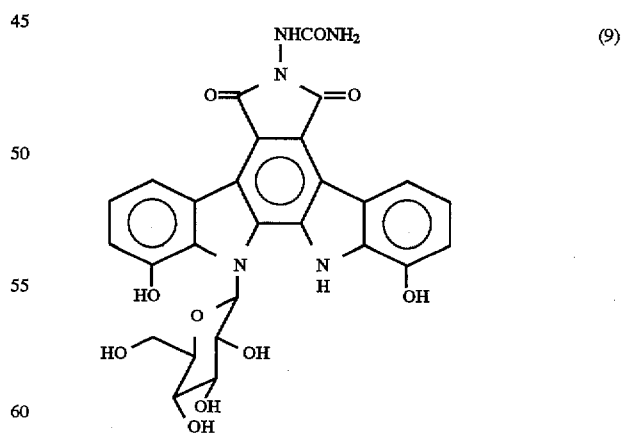

30 ml of methanol was added to 501.7 mg of the compound obtained in Example A and 501.7 mg of semicarbazide hydrochloride, 0.325 ml of triethylamine was then added, and the mixture was refluxed with heating for 8 hours. After the reaction, the reaction solution was concentrated to dryness, 300 ml of methyl ethyl ketone (MEK) and 200 ml of water were added, extraction operation was carried out, and another 300 ml of MEK was added to the water layer to carry out reextration. The MEK layers were combined and concentrated to dryness, 300 ml of methanol was added to the residue to dissolve it, the solution was subjected to a chromatograph tower of Sephadex LH-20 (3×28 cm), and elution was carried out with methanol. The fractions containing the desired product were concentrated to dryness to give 461 mg of the captioned compound represented by the formula (g) as red crystal-like powder.

Rf value: 0.15 (produced by Merck Co., Kiesel gel 60F$_{254}$, developing solvent; chloroform:methanol:tetrahydrofuran=2:1:1)

FAB-MS (m/z): 577 (M)$^+$ $^1$H-NMR (400 MHz, DMSO-d$_6$), δ (ppm): 11.0 (1H, s), 10.4 (1H, s), 10.0 (1H, s), 8.68 (1H, d, J=7.8 Hz), 8.66 (1H, brs), 8.51 (1H, d, J=7.8 Hz), 7.20 (2H, t, J=7.8 Hz), 7.01~7.07 (3H, m), 6.41 (2H, brs), 5.44 (1H, d, J=5.4 Hz), 5.38 (1H, brs), 5.23 (1H, d, J=4.9 Hz), 4.91 (1H, brs), 4.00~4.09 (2H, m), 3.75 (1H, m), 3.60~3.68 (2H, m), 3.39 (1H, m)

EXAMPLE 10

The compound represented by the formula

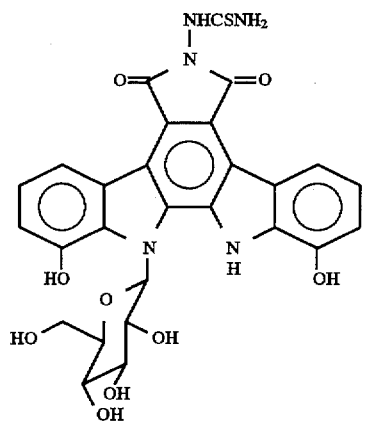

(10)

4 ml of methanol was added to 22 mg of the compound obtained in Example A and 20 mg of thiosemicarbazide, and the mixture was refluxed with heating for 22 hours. The reaction solution was concentrated to dryness, the residue was dissolved in 4 ml of methanol, the solution was subjected to a chromatograph tower of Sephadex LH-20 (1.8×35 cm), and elution was carried out with methanol. The fractions containing the desired product were concentrated to dryness to give 10.7 mg of the captioned compound represented by the formula (10).

Rf value: 0.29 (produced by Merck Co., Kiesel gel 60F$_{254}$, developing solvent; chloroform:methanol:tetrahydrofuran=2:1:1)

FAB-MS (m/z): 594 (M+H)$^+$ $^1$H-NMR (400 MHz, DMSO-d$_6$), δ (ppm): 11.0 (1H, s), 10.4 (1H, brs), 10.1 (1H, brs), 9.73 (1H, brs), 8.65 (1H, d, J=7.8 Hz), 8.49 (1H, d, J=7.8 Hz), 8.27 (2H, s), 7.21 (2H, t, J=7.8 Hz), 7.01~7.12 (3H, m), 5.45 (1H, brs), 5.37 (1H, brs), 5.24 (1H, brs), 4.91 (1H, brs), 3.97~4.10 (2H, m), 3.74 (1H, m), 3.62 (2H, m), 3.40 (1H, m)

EXAMPLE 11

The compound represented by the formula

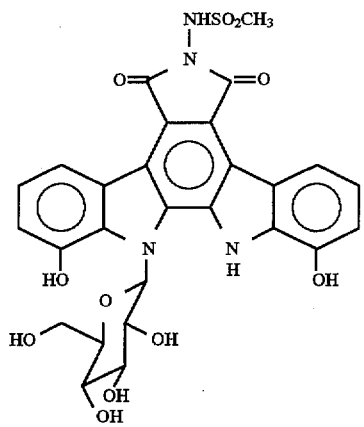

(11)

9.5 mg of the compound obtained in Example 1 was dissolved in 2 ml of tetrahydrofuran (THF), to the solution was added 30 mg of methanesulfonic anhydride (Aldrich Chemical Co.), and the mixture was allowed to stand at room temperature for 48 hours. The reaction solution was concentrated to dryness, and the residue was dissolved in 2 ml of methanol, subjected to a chromatograph tower of Sephadex LH-20 (1.8×34 cm), and eluted with methanol. The fractions containing the desired product were concentrated to dryness to give 8.3 mg of the captioned compound represented by the formula (11).

Rf value: 0.48 (produced by Merck Co., Kiesel gel 60F$_{254}$, developing solvent; chloroform:methanol:tetrahydrofuran=2:1:1)

FAB-MS (m/z): 612 (M)$^+$ $^1$H-NMR (400 MHz, DMSO-d$_6$), δ (ppm): 11.0 (1H, s), 10.5 (1H, brs), 10.4 (1H, s), 10.1 (1H, s), 8.67 (1H, d, J=7.9 Hz), 8.50 (1H, d, J=7.7 Hz), 7.22 (2H, t, J=7.6 Hz), 7.02~7.07 (3H, m), 5.43 (1H, d, J=5.8 Hz), 5.36 (1H, brs), 5.22 (1H, d, J=5.2 Hz), 4.89 (1H, d, J=4.8 Hz), 4.03 (2H, m), 3.75 (1H, m), 3.63 (2H, m), 3.40 (1H, m)

EXAMPLE 12

The compound represented by the formula

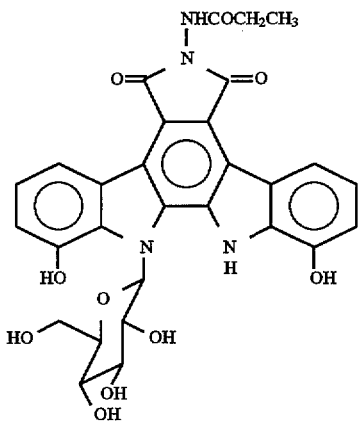

(12)

1 ml of the methanol and 2 ml of tetrahydrofuran were added to 11.7 mg of the compound obtained in Example 1 to make a solution, 0.1 ml of propionic anhydride (Aldrich Chemical Co.) was added, and the mixture was stirred at room temperature for 4 hours. 2 ml of water and 3 ml of methanol were added to the reaction solution, the mixture was allowed to stand for 30 minutes and then concentrated to dryness, and 3 ml of methanol was added to make a solution. The solution was subjected to a chromatograph tower of Sephadex LH-20 (1.8×30 cm) and eluted with methanol, and the fractions containing the desired product were concentrated to dryness to give 6.2 mg of the captioned compound represented by the formula (12).

Rf value: 0.55 (produced by Merck Co., Kiesel gel 60F$_{254}$, developing solvent; chloroform:methanol:tetrahydrofuran=2:1:1)
$^1$H-NMR (400 MHz, DMSO-d$_6$), δ (ppm): 11.0 (1H, s), 10.6 (1H, brs), 10.4 (1H, brs), 10.0 (1H, s), 8.64 (1H, d, J=7.8 Hz), 8.47 (1H, d, J=7.8 Hz), 7.20 (2H, t, J=7.8 Hz), 7.00~7.08 (3H, m), 5.30~5.45 (2H, m), 5.21 (1H, m), 4.92 (1H, m), 4.02 (2H, m), 3.75 (1H, m), 3.62 (2H, m), 3.38 (1H, m), 2.39 (2H, q, J=9.3 Hz), 1.16 (3H, t, J=7.3 Hz)

EXAMPLE 13

The compound represented by the formula

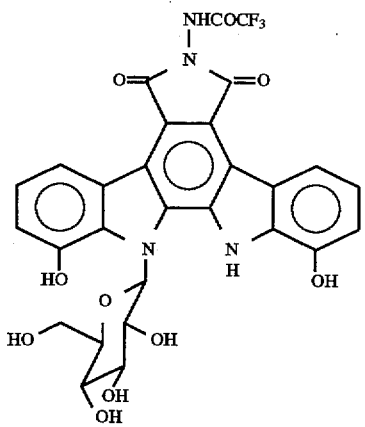

(13)

9.9 mg of the compound obtained in Example 1 was dissolved in 2 ml of tetrahydrofuran, 0.06 ml of trifluoroacetic anhydride (Aldrich Chemical Co.) was added, and the mixture was allowed to stand at room temperature for 15 minutes. 2 ml of water was added to the reaction solution, the mixture was concentrated to dryness, 2 ml of water and 10 ml of ethyl acetate were added, extraction operation was carried out, and the resultant ethyl acetate layer was concentrated to dryness. The resultant crude substance was dissolved in 3 ml of methanol, subjected to a chromatograph tower of Sephadex LH-20 (1.8×30 cm) and eluted with methanol, and the fractions containing the desired product were concentrated to dryness to give 9.5 mg of the captioned compound represented by the formula (13).

Rf value: 0.53 (produced by Merck Co., Kiesel gel 60F$_{254}$, developing solvent; chloroform:methanol:tetrahydrofuran=2:1:1)
FAB-MS (m/z) : 630 (M)$^+$ $^1$H-NMR (500 MHz, DMSO-d$_6$), δ (ppm): 12.7 (1H, brs), 11.0 (1H, brs), 10.5 (1H, brs), 10.1 (1H, brs), 8.61 (1H, d, J=7.6 Hz), 8.45 (1H, d, J=7.9 Hz), 7.21 (2H, t, J=7.6 Hz), 7.02~7.07 (3H, m), 5.42 (1H, d, J=5.8 Hz), 5.35 (1H, brs), 5.21 (1H, brs), 4.91 (1H, d, J=5.5 Hz), 4.02 (2H, m), 3.76 (1H, m), 3.61 (2H, m), 3.39 (1H, m)

EXAMPLE 14

The compound represented by the formula

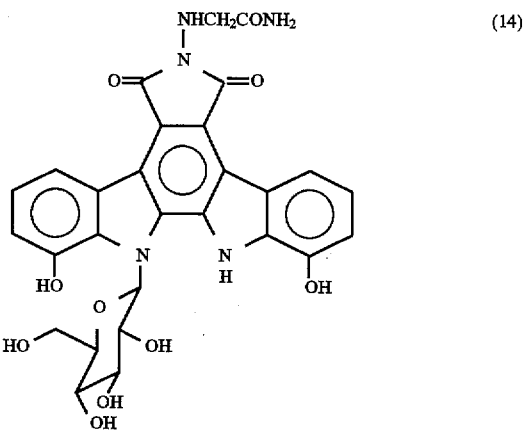

(14)

4 ml of methanol and 4 ml of benzene were added to 31.6 mg of the compound obtained in Example 8 to make a solution, 0.15 ml of trimethylsilyldiazomethane (10% hexane solution, Tokyo Kasei Co.) was added, and the mixture was allowed to stand at room for 10 minutes and concentrated to dryness to give 29.3 mg of the methyl ester of the compound obtained in Example 8. This was dissolved in 5 ml of methanol, 0.6 ml of concentrated ammonia water was added, and the mixture was stirred at room temperature for 16 hours. The reaction solution was concentrated to dryness, 3 ml of methanol was added to the residue to make a solution, and the solution was subjected to a chromatograph tower of Sephadex LH-20 (1.8×36 cm) and eluted with methanol. The fractions containing the desired product were concentrated to dryness to give 16.9 mg of the captioned compound represented by the formula (14).

Rf value: 0.22 (produced by Merck Co., Kiesel gel 60F$_{254}$, developing solvent; chloroform:methanol:tetrahydrofuran=2:1:1)

FAB-MS (m/z): 592 (M+H)$^+$
$^1$H-NMR (400 MHz, DMSO-d$_6$), δ (ppm): 10.9 (1H, s), 10.4 (1H, brs), 10.0 (1H, brs). 8.69 (1H, d, J=7.3 Hz), 8.52 (1H, d, J=8.3 Hz), 7.77 (1H, brs), 7.39 (1H, brs), 7.19 (2H, t, J=7.8 Hz), 6.98~7.05 (3H, m), 6.25 (1H, t, J=3.9 Hz), 5.41 (1H, d, J=5.4 Hz), 5.35 (1H, brs), 5.20 (1H, d, J=5.4 Hz), 4.87 (1H, d, J=5.4 Hz), 4.02 (2H, m), 3.74 (1H, m), 3.68~3.70 (4H, m), 3.39 (1H, m)

EXAMPLE 15

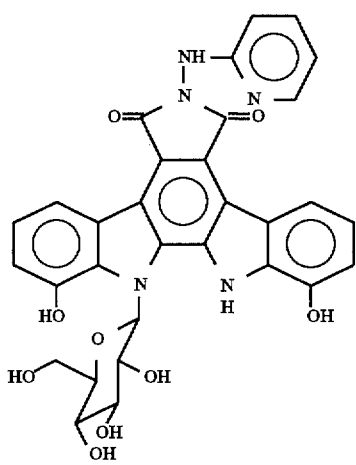

(15)

2 ml of methanol was added to 11 mg of the compound obtained in Example A and 10 mg of 2-hydrazinopyridine (Aldrich Chemical Co.) to make a solution, and the solution was refluxed with heating for 1.5 hours. The reaction solution was concentrated to dryness, 30 ml of water and 50 ml of ethyl acetate were added, the water layer was adjusted to pH 5 with 1N hydrochloric acid, extraction operation was carried out, and the resultant ethyl acetate layer was concentrated to dryness. The resultant crude substance was dissolved in 2 ml of methanol, subjected to a chromatograph tower of Sephadex LH-20 (1.8×36 cm) and eluted with methanol. The fractions containing the desired product were concentrated to dryness to give 10 mg of the captioned compound represented by the formula (15).

Rf value: 0.46 (produced by Merck Co., Kiesel gel 60F$_{254}$, developing solvent; chloroform:methanol:tetrahydrofuran=2:1:1)

FAB-MS (m/z): 612 (M+H)$^+$ $^1$H-NMR (400 MHz, DMSO-d$_6$), δ (ppm): 11.0 (1H, s), 10.4 (1H, s), 10.0 (1H, s), 9.34 (1H, s), 8.65 (1H, d. J=8.3 Hz), 8.48 (1H, d, J=7.8 Hz), 7.95 (1H, d, J=4.9 Hz), 7.62 (1H, t, J=7.8 Hz), 7.18 (2H, t, J=7.8 Hz), 7.00~7.08 (3H, m), 6.86 (1H, d, J=7.8 Hz), 6.78 (1H, dd, J=4.9, 7.8 Hz), 5.44 (1H, d, J=5.8 Hz), 5.37 (1H, brs), 5.23 (1H, d, J=5.8 Hz), 4.92 (1H, brs), 4.02 (2H, m), 3.76 (1H, m), 3.64 (2H, m), 3.41 (1H, m)

EXAMPLE 16

The compound represented by the formula

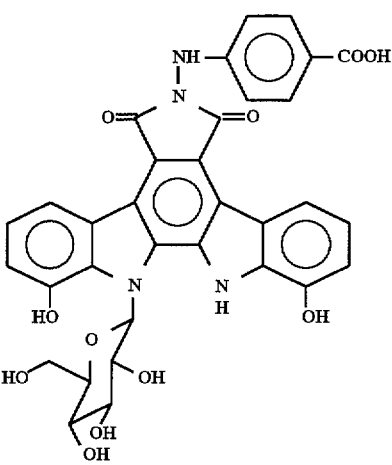

(16)

4 ml of methanol was added to 24 mg of the compound obtained in Example A and 4-hydrazinobenzoic acid (Aldrich Chemical Co.), and the mixture was refluxed with heating for 2 hours. The reaction solution was subjected to a chromatograph tower of Sephadex LH-20 (1.8×44 cm) and eluted with methanol. The fractions containing the desired product were concentrated to dryness to give 20.9 mg of the captioned compound represented by the formula (16) as red crystal-like powder.

Rf value: 0.31 (produced by Merck Co., Kiesel gel 60F$_{254}$, developing solvent; chloroform:methanol:tetrahydrofuran=2:1:1)

FAB-MS (m/z): 655 (M+H)$^+$ $^1$H-NMR (500 MHz, DMSO-d$_6$), δ (ppm): 11.0 (1H, s), 10.5 (1H, brs), 10.1 (1H, brs), 9.11 (1H, s), 8.65 (1H, d, J=7.9 Hz), 8.48 (1H, d, J=7.9 Hz), 7.80 (2H, d, J=8.3 Hz), 7.18 (2H, t, J=7.6 Hz), 7.01~7.08 (3H, m), 6.84 (2H, d, J=8.3 Hz), 5.20~5.60 (3H, brs), 4.96 (1H, brs), 4.03 (2H, m), 3.76 (1H, m), 3.65 (2H, m), 3.41 (1H, m)

EXAMPLE 17

The compound represented by the formula

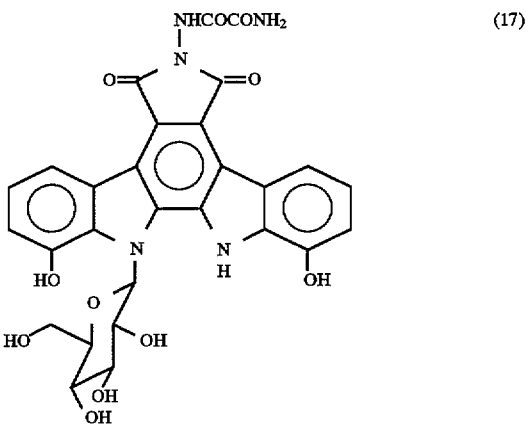

(17)

6 ml of 50% methanol was added to 26 mg of the compound obtained in Example A and 38 mg of oxamic hydrazine (Aldrich Chemical Co.), and the mixture was stirred with heating at 80° C. for 20 hours. The reaction solution was concentrated to dryness, 15 ml of water and 50 ml of ethyl acetate were added, the mixture was adjusted to pH 2 with 1N hydrochloric acid, and extraction operation was carried out. The ethyl acetate layer was concentrated, and the precipitated crystals were collected by filtration to give 10 mg of the captioned compound represented by the formula (17).

Rf value: 0.38 (produced by Merck Co., Kiesel gel 60$F_{254}$, developing solvent; chloroform:methanol:tetrahydrofuran=2:1:1)
FAB-MS (m/z): 606 (M+H)$^+$
$^1$H-NMR (500 MHz, DMSO-$d_6$), δ (ppm): 11.4 (1H, s), 11.0 (1H, s), 10.4 (1H, s), 10.0 (1H, s), 8.63 (1H, d, J=7.9 Hz), 8.46 (1H, d, J=7.9 Hz), 8.38 (1H, s), 8.11 (1H, s), 7.21 (2H, t, J=7.9 Hz), 7.02~7.07 (3H, m), 5.41 (1H, d, J=5.8 Hz), 5.35 (1H, t, J=5.8 Hz), 5.19 (1H, d, J=5.2 Hz), 4.89 (1H, d, J=5.5 Hz), 4.03 (2H, m), 3.76 (1H, m), 3.63 (2H, m), 3.40 (1H, m)

EXAMPLE 18

The compound represented by the formula

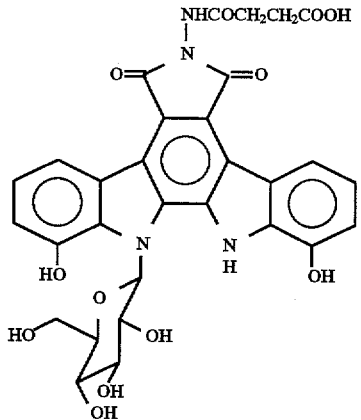

(18)

26.7 mg of the compound obtained in Example 1 and 5.5 mg of succinic anhydride were dissolved in 0.5 ml of pyridine, and the solution was stirred at room temperature for 18 hours. This was concentrated to dryness under reduced pressure and the residue was dissolved in a small quantity of N,N-dimethylformamide and subjected to high performance liquid chromatography (HPLC) [Chromatolex ODS, 20×250 mm, moving phase: 20% acetonitrile]. The fractions containing the desired product were concentrated to remove acetonitrile, adjusted to pH 2 and extracted with 100 ml of ethyl acetate. The ethyl acetate layer was dehydrated with anhydrous sodium sulfate and concentrated to dryness. The residue was dissolved in methanol and subjected to column chromatography on Sephadex LH-20 (inner diameter 1.5 cm, length 90 cm, eluted with methanol), and the fractions containing the desired product were concentrated to dryness to give 9.7 mg of the captioned compound represented by the formula (18) as orange powder.

HPLC; Rt, 5.3 minutes (column: Chromatolex ODS, inner diameter 4.6 mm, length 250 mm, detection; UV 305 nm, flow rate; 1 ml/minute, moving phase; 27.5% acetonitrile:t-rifluoroacetic acid=1000:1)
FAB-MS (m/z): 657 (M+Na)$^+$
$^1$H-NMR (400 MHz, DMSO-$d_6$), δ (ppm): 11.0 (1H, s), 10.7 (1H, brs), 10.4 (1H, brs), 10.1 (1H, brs), 8.64 (1H, d, J=7.9 Hz), 8.47 (1H, d, J=7.9 Hz), 7.19 (2H, t, J=7.8 Hz), 7.01~7.07 (3H, m), 5.42 (2H, brs), 5.22 (1H, brs), 4.92 (1H, brs), 4.02 (2H, m), 3.75 (1H, m), 3.63 (2H, m), 3.40 (1H, m), 2.65 (2H, t, J=7.3 Hz), 2.52 (2H, t, J=7.3 Hz)

EXAMPLE 19

The compound represented by the formula

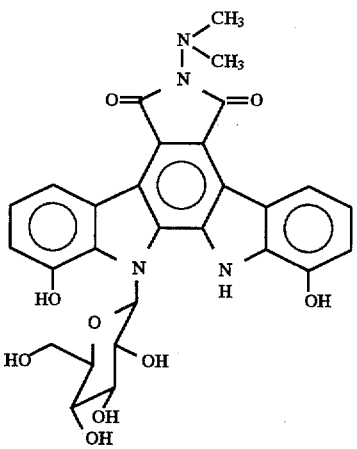

(19)

30 mg of the compound obtained in Example 1 was dissolved in 0.5 ml of N,N-dimethylformamide, 0.1 ml of methyl iodide was added, and the mixture was stirred at room temperature for 18 hours. This was mixed with 50 ml of ethyl acetate, the mixture was washed successively with 1% sodium bicarbonate aqueous solution and then water, and the ethyl acetate layer was dehydrated with anhydrous sodium sulfate and concentrated to dryness. The residue was dissolved in methanol and subjected to column chromatography on Sephadex LH-20 (1.5×90 cm, eluted with methanol), and the fractions containing the desired product were concentrated to dryness to give 18.0 mg of the captioned compound represented by the formula (19) as orange powder.

Rf value: 0.51 (produced by Merck Co., Kiesel gel 60$F_{254}$, developing solvent; chloroform:methanol:tetrahydrofuran:acetic acid=20:10:10:1)
FAB-MS (m/z): 563 (M+H)$^+$
$^1$H-NMR (400 MHz, DMSO-$d_6$), δ (ppm): 10.9 (1H, s), 10.3 (1H, s), 9.95 (1H, s), 8.70 (1H, d, J=8.3 Hz), 8.53 (1H, d, J=8.3 Hz), 7.18 (2H, t, J=7.8 Hz), 7.00~7.06 (3H, m), 5.41 (1H, d, J=5.4 Hz), 5.34 (1H, t, J=5.4 Hz), 5.19 (1H, d, J=5.4 Hz), 4.86 (1H, d, J=5.4 Hz), 4.02 (2H, m), 3.75 (1H, m), 3.62 (2H, m), 3.39 (1H, m), 3.02 (6H, s)

EXAMPLE 20

The compound represented by the formula

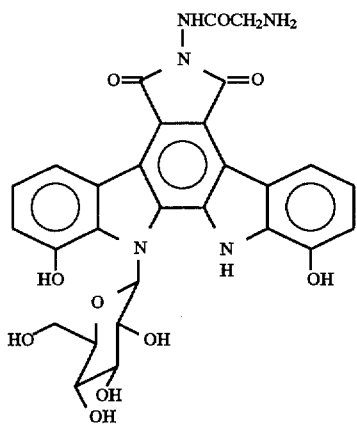

82.1 mg of t-butyloxycarbonyl (Boc)-glycine was dissolved in 1 ml of methylene chloride, the solution was stirred under ice cooling for 15 minutes, 96.7 mg of dicyclohexylcarbodiimide dissolved in 1 ml of methylene chloride was added, and the mixture was stirred under ice cooling for 15 minutes. To this was added 227.6 mg of the compound obtained in Example 1 dissolved in 6 ml of pyridine, and the mixture was stirred at room temperature for 17 hours. The reaction solution was concentrated to dryness, the residue was dissolved in ethyl acetate, the solution was washed successively with saturated saline, acidic water (pH 2) and then water, and the ethyl acetate layer was dehydrated with anhydrous sodium sulfate and concentrated to dryness. The residue was subjected to silica gel column chromatography (1.5×55 cm, eluted with toluene:methanol=6:1), and the fractions containing the desired product were concentrated to dryness to give 105.2 mg of the Boc derivative of the captioned compound represented by the formula (20) as orange powder. This was dissolved in 1.2 ml of trifluoroacetic acid, and the solution was stirred at room temperature for 30 minutes to remove the Boc group. The reaction solution was concentrated to dryness, the residue was dissolved in 15 ml of water, and the solution was adjusted to pH 7.5–8 and extracted with n-butanol. 40 ml of water was added to the n-butanol layer (50 ml), and the mixture was adjusted to pH 2 with dilute hydrochloric acid and concentrated to dryness. The resultant orange powder was dissolved in methanol and subjected to column chromatography on Sephadex LH-20 (1.5×38 cm, eluted with methanol), and the fractions containing the desired product were concentrated to dryness to give 63.7 mg of the hydrochloride of the captioned compound represented by the formula (20) as orange powder.

HPLC; Rt, 8.7 minutes (column: Chromatolex ODS, inner diameter 4.6 mm, length 250 mm, detection; UV 305 nm, flow rate; 1 ml/minute, moving phase; 20% acetonitrile:trifluoroacetic acid=1000:1→70% acetonitrile:trifluoroacetic acid=1000:1, 30 minutes linear gradient)

FAB-MS(m/z): 592 (M+H)$^+$ $^1$H-NMR (hydrochloride, 400 MHz, DMSO-d$_6$), δ (ppm): 11.3 (1H, brs), 11.0 (1H, brs), 10.5 (1H, s), 10.1 (1H, s), 8.62 (1H, d, J=8.3 Hz), 8.46 (1H, d, J=8.3 Hz), 8.31 (2H, s), 7.19 (2H, t, J=7.8 Hz), 7.03–7.08 (3H, m), 5.46 (1H, brs), 5.34 (1H, brs), 5.27 (1H, brs), 4.91 (1H, brd, J=4.9 Hz), 4.03 (2H, m), 3.98 (2H, s), 3.76 (1H, m), 3.64 (2H, m), 3.40 (1H, m)

EXAMPLE 21

The compound represented by the formula

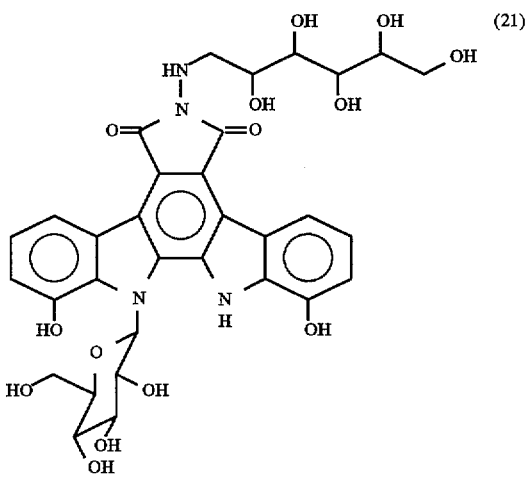

40.0 mg of the compound obtained in Example A was dissolved in 3 ml of N,N-dimethylformamide, 42.2 mg of 1-deoxy-1-hydrazino-D-sorbitol and 0.1 ml of triethylamine was added, and the mixture was refluxed with heating for 16 hours. This was brought back to room temperature, subjected to a chromatograph tower of Sephadex LH-20 (1.8× 20 cm) and eluted with methanol. The fractions containing the desired product were concentrated to dryness to give 20.0 mg of the captioned compound represented by the formula (21).

FAB-MS (m/z): 699 (M+H)$^+$ $^1$H-NMR (400 MHz, DMSO-d$_6$), δ (ppm): 10.91 (1H, s), 10.35 (1H, brs), 9.96 (1H, brs), 8.73 (1H, d, J=8.9 Hz), 8.54 (1H, d, J=8.9 Hz), 7.20 (2H, t, J=8.4 Hz), 7.00–7.10 (3H, m), 5.76 (1H, t, J=3.8 Hz), 5.42 (1H, d, J=5.5 Hz), 5.37 (1H, brs), 5.22 (1H, d, J=5.5 Hz), 4.89 (1H, brs), 4.67 (1H, d, J=3.4 Hz), 4.45 (1H, d, J=5.1 Hz), 4.37 (1H, d, J=7.0 Hz), 4.25–4.43 (2H, m), 4.00 (2H, m), 3.55–3.80 (7H, m), 3.44–3.52 (2H, m), 3.35–3.44 (2H, m), 3.05–3.20 (2H, m)

EXAMPLE 22

The compound represented by the formula

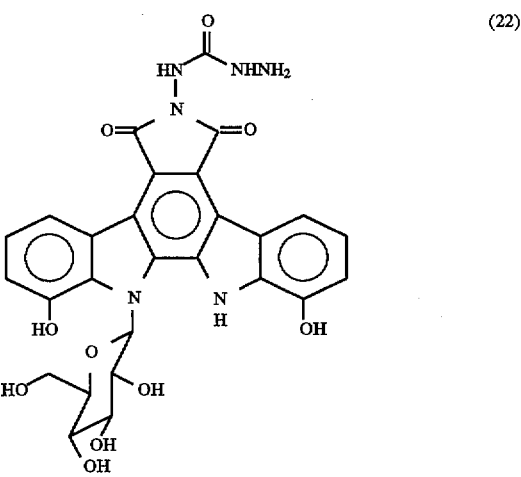

100 mg of the compound obtained in Example A was dissolved in 5 ml of N,N-dimethylformamide, 100 mg of carbohydrazide was added, and the mixture was stirred at 80° C. for 3 hours and concentrated to dryness. The residue was dissolved in methanol and the insoluble matters were removed by Celite filtration. The resultant filtrate was concentrated, and the residue was dissolved in a small quantity of methanol, subjected to a chromatograph tower of Sephadex LH-20 (1.5×20 cm) and eluted with methanol. The fractions containing the desired product were concentrated to dryness to give 91.2 mg of the captioned compound represented by the formula (22).

Rf value: 0.1 (produced by Merck Co., Kiesel gel 60F$_{254}$, developing solvent; chloroform-methanol-tetrahydrofuran=2:1:1:)

FAB-MS (m/z): 593 (M+H)$^+$ $^1$H-NMR (400 MHz, DMSO-d$_6$), δ (ppm): 10.96 (1H, s), 10.40 (1H, s), 10.01 (1H, s), 8.95 (1H, s), 8.65 (1H, d, J=8.2 Hz), 8.50 (1H, d, J=8.2 Hz), 7.90 (1H, s), 7.17 (2H, t, J=6.9 Hz), 7.00–7.10 (3H, m), 5.43 (1H, d, J=4.1 Hz), 5.38 (1H, brs), 5.20 (1H, s), 4.90 (1H, s), 4.39 (2H, brs), 4.04 (2H, m), 3.75 (1H, m), 3.55–3.70 (2H, m), 3.38 (1H, m)

EXAMPLE 23

The compound represented by the formula

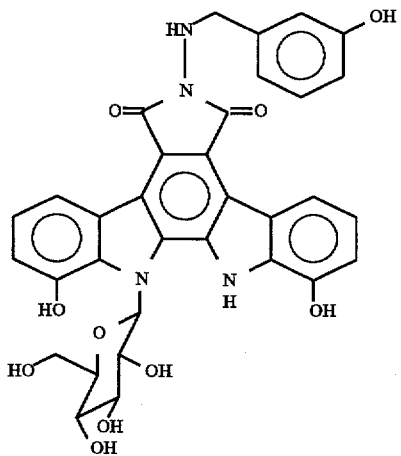

(23)

15.0 mg of the compound obtained in Example A was dissolved in 1 ml of N,N-dimethylformamide, 32 mg of 3-hydoxybenzylhydrazine dihydrochloride and 0.1 ml of 10% sodium bicarbonate aqueous solution were added, and the mixture was stirred at 80° C. for 4 hours. This was mixed with 50 ml of ethyl acetate, the mixture was washed successively with 0.2N hydrochloric acid and then saturated saline, and the ethyl acetate layer was dehydrated with anhydrous sodium sulfate and concentrated to dryness. The residue was dissolved in a small quantity of methanol, subjected to a chromatograph tower of Sephadex LH-20 (1.8×15 cm) and eluted with methanol. The fractions containing the desired product were concentrated to dryness to give 15.3 mg of the captioned compound represented by the formula (23).

Rf value: 0.22 (produced by Merck Co., Kiesel gel 60F$_{254}$, developing solvent;chloroform-methanol-tetrahydrofuran=5:1:1)

FAB-MS (m/z): 641 (M+H)$^+$ $^1$H-NMR (200 MHz, DMSO-d$_6$), δ (ppm): 10.90 (1H, s), 10.38 (1H, s), 9.99 (1H, s), 9.30 (1H, s), 8.70 (1H, d, J=8.1 Hz), 8.53 (1H, d, J=8.5 Hz), 6.86–7.22 (8H, m), 6.61 (1H, dd, J=2.2, 8.4 Hz), 6.03 (1H, t, J=5.1 Hz), 5.43 (1H, d, J=5.4 Hz), 5.35 (1H, t, J=5.0 Hz), 5.22 (1H, d, J=5.4 Hz), 4.89 (1H, d, J=5.4 Hz), 4.19 (2H, d, J=5.1 Hz), 4.00 (2H, m), 3.72 (1H, m), 3.53–3.70 (2H, m), 3.38 (1H, m)

EXAMPLE 24

The compound represented by the formula

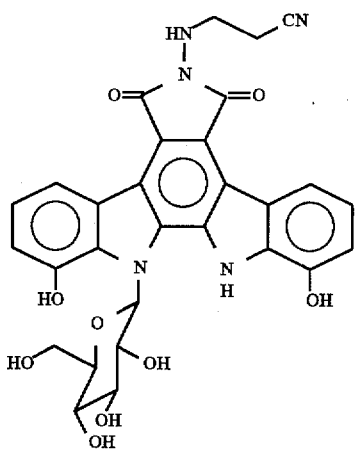

(24)

64.6 mg of the compound obtained in Example A was dissolved in 2 ml of N,N-dimethylformamide, 30 mg of 2-cyanoethylhydrazine, and the mixture was stirred at 90° C. for 1.5 hours. 50 ml of 0.2N hydrochloric acid was added to the reaction solution, and the mixture was extracted with ethyl acetate (50 ml×2). The ethyl acetate layer was concentrated to dryness, and the residue was dissolved in a small quantity of methanol, subjected to a chromatograph tower of Sephadex LH-20 (1.8×30 cm) and eluted with methanol. The fractions containing the desired product were concentrated to dryness to give 45.0 mg of the captioned compound represented by the formula (24).

Rf value: 0.39 (produced by Merck Co., Kiesel gel 60F$_{254}$, developing solvent; chloroform:methanol=3:1)

FAB-MS (m/z): 588 (M+H)$^+$ $^1$H-NMR (200 MHz, DMSO-d$_6$), δ (ppm): 10.91 (1H, s), 10.36 (1H, s), 9.98 (1H, s), 8.70 (1H, d, J=8.4 Hz), 8.53 (1H, d, J=8.4 Hz), 7.18 (2H, t, J=8.4 Hz), 6.95–7.10 (3H, m), 6.15 (1H, t, J=4.2 Hz), 5.42 (1H, d, J=5.7 Hz), 5.34 (1H, brs), 5.23 (1H, d, J=4.4 Hz), 4.91 (1H, d, J=5.3 Hz), 4.00 (2H, m), 3.72 (1H, m), 3.55–3.70 (2H, m), 3.39 (1H, m), 3.30 (2H, t d, J=4.2, 6.2 Hz), 2.69 (2H, t, J=6.2 Hz)

EXAMPLE 25

The compound represented by the formula

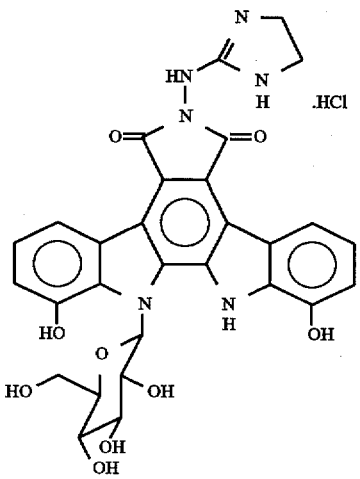

(25)

1.09 g of the compound obtained in Example A was dissolved in 35 ml of N,N-dimethylformamide—2 ml of water, 455 mg of 2-hydrazino-2-imidazoline hydrobromide and 211 mg of sodium bicarbonate were added, and the mixture was stirred at 80° C. for 2 hours and concentrated to dryness. The residue was dissolved in 300 ml of 0.2N hydrochloric acid and extracted with n-butanol (1 L×2). The butanol layer was concentrated to dryness, and the residue was dissolved in a small quantity of methanol, subjected to a chromatograph tower of Sephadex LH-20 (3.0×80 cm) and eluted with methanol. The fractions containing the desired product were concentrated to dryness to give 650 mg of the captioned compound represented by the formula (25).

Rf value: 0.55 (produced by Merck Co., Kiesel gel 60$F_{254}$, developing solvent; n-butanol:acetic acid:water= 4:1:1)

FAB-MS (m/z): 603 (M+H)$^+$ $^1$H-NMR (400 MHz, DMSO-$d_6$), δ (ppm): 11.2 (1H, s), 10.90 (1H, brs), 10.50 (1H, s), 10.14 (1H, s), 9.42 (1H, brs), 8.92 (1H, brs), 8.62 (1H, d, J=10.6 Hz), 8.45 (1H, d, J=9.5 Hz), 7.22 (2H, t, J=6.5 Hz), 7.02–7.10 (3H, m), 5.48 (1H, d, J=4.7 Hz), 5.32 (2H, brm), 4.94 (1H, d, J=3.5 Hz), 4.04 (2H, m), 3.70–3.90 (5H, m), 3.54–3.70 (2H, m), 3.41 (1H, m)

EXAMPLE 26

The compound represented by the formula

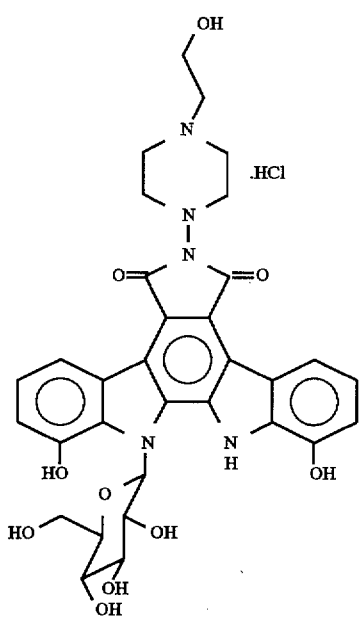

48.3 mg of the compound obtained in Example A was dissolved in 1 ml of N,N-dimethylformamide, 14.3 mg of 1-amino-4-(2-hydroxyethyl) piperazine and 0.1 ml of saturated sodium bicarbonate aqueous solution were added, and the mixture was stirred at 80° C. for 2 hours. This was distributed between 50 ml of ethyl acetate and 50 ml of water, 5 ml of 0.2N hydrochloric acid was added to the water layer, and the mixture was extracted with n-butanol (100 ml×2). The butanol layer was concentrated to dryness, and the residue was dissolved in a small quantity of methanol, subjected to a chromatograph tower of Sephadex LH-20 (1.8×30 cm) and eluted with methanol. The fractions containing the desired product were concentrated to dryness to give 22 mg of the captioned compound represented by the formula (26).

Rf value: 0.53 (produced by Merck Co., Kiesel gel 60$F_{254}$, developing solvent; n-butanol:acetic acid:water= 4:1:1)

FAB-MS (m/z): 648 (M+H)$^+$ $^1$H-NMR (400 MHz, DMSO-$d_6$), δ (ppm): 10.92 (1H, s), 10.50 (2H, brs), 10.10 (1H, s), 8.66 (1H, d, J=7.2 Hz), 8.50 (1H, d, J=8.9 Hz), 7.18 (2H, t, J=8.9 Hz), 7.02–7.12 (3H, m), 5.46 (1H, d, J=5.6 Hz), 5.25–5.40 (3H, brm), 4.86 (1H, d, J=5.6 Hz), 3.95–4.20 (4H, m), 3.70–3.90 (4H, m), 3.55–3.70 (4H, m), 3.20–3.50 (6H, m)

EXAMPLE 27

The compound represented by the formula

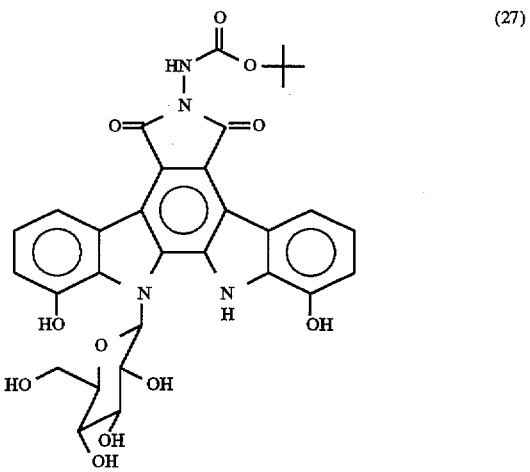

24 mg of the compound obtained in Example A was dissolved in 0.6 ml of N,N-dimethylformamide, 10 mg of t-butyl carbazinate acid was added, and the mixture was stirred at 80° C. for 6 hours. This was mixed with 50 ml of ethyl acetate, the mixture was washed successively with water (30 ml×2) and saturated saline, and the ethyl acetate layer was dehydrated with anhydrous sodium sulfate and concentrated to dryness. The residue was dissolved in 1 ml of methanol, subjected to a chromatograph tower of Sephadex LH-20 (1.6×20 cm) and eluted with methanol. The fractions containing the desired product were concentrated to dryness to give 27.2 mg of the captioned compound represented by the formula (27).

Rf value: 0.42 (produced by Merck Co., Kiesel gel 60$F_{254}$, developing solvent; chloroform:methanol=4:1)

FAB-MS (m/z): 684 (M+H)$^+$ $^1$H-NMR (400 MHz, DMSO-$d_6$), δ (ppm): 10.99 (1H, s), 10.42 (1H, s), 10.02 (1H, s), 9.82 (1H, brs), 8.65 (1H, d, J=7.7 Hz), 8.49 (1H, d, J=7.7 Hz), 7.18 (2H, t, J=7.7 Hz), 7.00–7.10 (3H, m), 5.42 (1H, brs), 5.35 (1H, brs), 5.21 (1H, brs), 4.90 (1H, brs), 4.02 (2H, m), 3.72 (1H, m), 3.56–3.70 (2H, m), 3.40 (1H, m), 1.50 (9H, s)

EXAMPLE 28

The compound represented by the formula

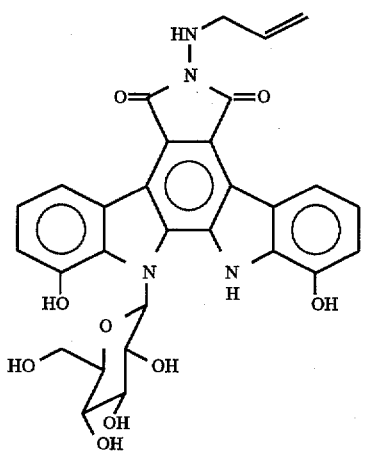

(28)

and the compound represented by the formula

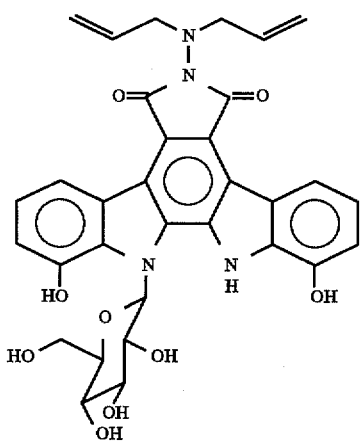

(29)

177 mg of the compound obtained in Example 1 was dissolved in 6 ml of N,N-dimethylformamide, 0.68 ml of allyl bromide was added, and the mixture was stirred at room temperature for 1 day. 200 ml of water was added to the mixture, the mixture was extracted with ethyl acetate (200 ml×3), and the ethyl acetate layer was dehydrated with saturated saline and concentrated to dryness. The residue was dissolved in 3 ml of methanol, subjected to a chromatograph tower of Sephadex LH-20 (2.5×40 cm) and eluted with methanol. The fractions containing the desired products respectively were concentrated to dryness to give 42.1 mg of the captioned compound represented by the formula (28) and 67.5 mg of the compound represented by the formula (29).

The compound represented by the formula (28)

Rf value: 0.68 (produced by Merck Co., Kiesel gel 60F$_{254}$, developing solvent; chloroform:methanol=2:1)

FAB-MS (m/z): 575 (M+H)$^+$ $^1$H-NMR (400 MHz, DMSO-d$_6$), δ (ppm): 10.90 (1H, s), 10.38 (1H, s), 9.98 (1H, s), 8.70 (1H, d, J=9.0 Hz), 8.52 (1H, d, J=10.2 Hz), 7.20 (2H, t, J=7.7 Hz), 6.95–7.08 (3H, m), 5.92 (2H, m), 5.40 (1H, d, J=6.4 Hz), 5.32 (1H, m), 5.20 (2H, m), 5.05 (1H, d, J=11.5 Hz), 4.88 (1H, d, J=5.8 Hz), 4.00 (2H, m), 3.67–3.78 (3H, m), 3.58–3.65 (2H, m), 3.35 (1H, m)

The compound represented by the formula (29)

Rf value: 0.75 (produced by Merck Co., Kiesel gel 60F$_{254}$, developing solvent; chloroform:methanol=2:1)

$^1$H-NMR (400 MHz, DMSO-d$_6$), δ (ppm): 10.91 (1H, s), 10.40 (1H, brs), 10.00 (1H, brs), 8.66 (1H, d, J=9.4 Hz), 8.50 (1H, d, J=9.4 Hz), 7.18 (2H, t, J=8.0 Hz), 7.00–7.10 (3H, m), 5.90 (2H, ddt, J=6.3, 10.2, 17.0 Hz), 5.42 (1H, d, J=5.3 Hz), 5.33 (1H, brs), 5.23 (2H, d, J=17.0 Hz), 5.22 (1H, brs), 5.04 (2H, d, J=10.2 Hz), 4.91 (1H, brs), 4.02 (2H, m), 3.97 (4H, d, J=6.3 Hz), 3.70 (1H, m), 3.51–3.66 (2H, m), 3.35 (1H, m)

EXAMPLE 29

The compound represented by the formula

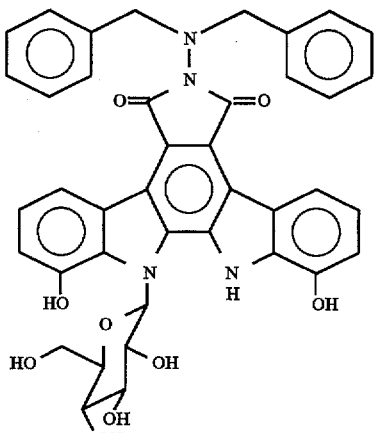

(30)

and the compound represented by the formula

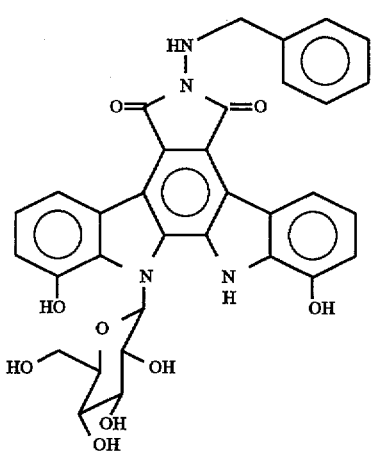

(31)

20 mg of the compound obtained in Example 1 was dissolved in 1 ml of N,N-dimethylformamide, 0.3 ml of benzyl bromide was added, and the mixture was stirred overnight. This was mixed with 40 ml of ethyl acetate, the mixture was washed successively with water (30 ml×2) and and then saturated saline, and the ethyl acetate layer was dehydrated with anhydrous sodium sulfate and concentrated to dryness. The residue was dissolved in 1 ml of methanol, subjected to a chromatograph tower of Sephadex LH-20 (1.6×30 cm) and eluted with methanol. The fractions containing the desired products respectively were concentrated to dryness to give 13.2 mg of the captioned compound represented by the formula (30) and 7.2 mg of the compound represented by the formula (31).

The compound represented by the formula (30)

Rf value: 0.44 (produced by Merck Co., Kiesel gel 60F$_{254}$, developing solvent; chloroform:methanol=3:1)

FAB-MS (m/z): 715 (M+H)$^+$ $^1$H-NMR (200 MHz, DMSO-d$_6$), δ (ppm): 10.85 (1H, s), 10.35 (1H, s), 9.96 (1H, s), 8.65 (1H, d, J=8.5 Hz), 8.45 (1H, d, J=9.0 Hz), 7.50–7.65 (4H, m), 7.10–7.40 (8H, m), 6.95–7.10 (3H, m), 5.40 (1H, d, J=5.4 Hz), 5.30 (1H, brs), 5.18 (1H, d, J=4.9 Hz), 4.83 (1H, d, J=4.9 Hz), 4.58 (2H, s), 4.55 (2H, s), 4.00 (2H, m), 3.46–3.80 (3H, m), 3.36 (1H, m) The compound represented by the formula (31)

Rf value: 0.38 (produced by Merck Co., Kiesel gel 60F$_{254}$, developing solvent; chloroform:methanol=3:1)
FAB-MS (m/z): 625 (M+H)$^+$
$^1$H-NMR (300 MHz, DMSO-d$_6$), δ (ppm): 10.88 (1H, s), 10.40 (1H, brs), 10.00 (1H, brs), 8.67 (1H, d, J=7.9 Hz), 8.51 (1H, d, J=7.3 Hz), 7.50 (2H, d, J=6.9 Hz), 7.30 (2H, t, J=6.9 Hz), 7.21 (1H, t, J=6.9 Hz), 7.16 (2H, t, J=7.3 Hz), 6.96–7.07 (3H, m), 6.13 (1H, t, J=5.3 Hz), 5.42 (1H, d, J=5.9 Hz), 5.21 (1H, d, J=5.3 Hz), 4.91 (1H, brs), 4.55 (1H, brs), 4.28 (2H, d, J=5.3 Hz), 4.02 (2H, m), 3.72 (1H, m), 3.55–3.70 (2H, m), 3.40 (1H, m)

EXAMPLE 30

The compound represented by the formula

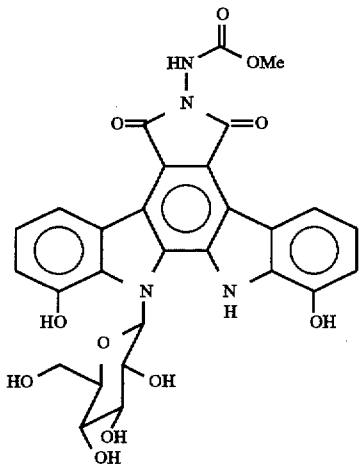

(32)

1.4 g of the compound obtained in Example A was dissolved in 30 ml of N,N-dimethylformamide, 1 g of methyl carbazinate was added, and the mixture was stirred at 80° C. for 2 hours. 400 ml of water was added to the mixture, and the mixture was extracted with ethyl acetate (500 ml×3). The resultant ethyl acetate layer was concentrated to dryness. The residue was dissolved in 5 ml of methanol, subjected to a chromatograph tower of Sephadex LH-20 (3.0×80 cm) and eluted with methanol. The fractions containing the desired product were concentrated to dryness to give 1.3 g of the captioned compound represented by the formula (32).

Rf value: 0.18 (produced by Merck Co., Kiesel gel 60F$_{254}$, developing solvent; chloroform:methanol=4:1)
FAB-MS (m/z): 592 (M+H)$^+$
$^1$H-NMR (300 MHz, DMSO-d$_6$), δ (ppm): 11.00 (1H, s), 10.42 (1H, brs), 10.18 (1H, s), 10.04 (1H, brs), 8.64 (1H, d, J=7.6 Hz), 8.47 (1H, d, J=8.3 Hz), 7.20 (2H, t, J=8.3 Hz), 7.00–7.10 (3H, m), 5.42 (1H, brs), 5.35 (1H, brs), 5.21 (1H, brs), 4.91 (1H, brs), 4.02 (2H, m), 3.75 (3H, s), 3.50–3.70 (3H, m), 3.40 (1H, m)

EXAMPLE 31

The compound represented by the formula

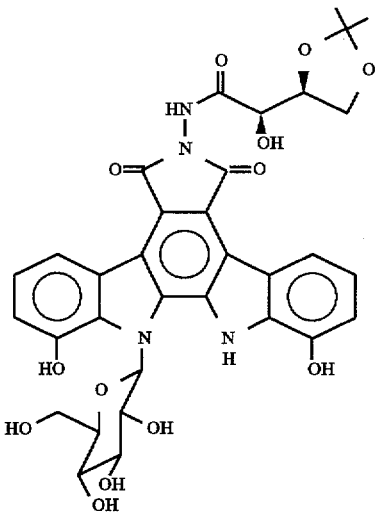

(33)

90 mg of the compound obtained in Example A was dissolved in 1 ml of N,N-dimethylformamide, 67 mg of (2R,3S)-3,4-0-isopropylidene-2,3,4-trihydroxybutane carbohydrazide, and the mixture was stirred at 80° C. for 7 hours and then at room temperature for 3 days. 50 ml of water was added to the mixture, and the mixture was extracted with ethyl acetate (50 ml×2). The resultant ethyl acetate layer was concentrated to dryness. The residue was dissolved in 3 ml of methanol, subjected to a chromatograph tower of Sephadex LH-20 (1.8×25 cm) and eluted with methanol. The fractions containing the desired product were concentrated to dryness to give 112 mg of the captioned compound represented by the formula (33).

Rf value: 0.14 (produced by Merck Co., Kiesel gel 60F$_{254}$, developing solvent; chloroform:methanol=4:1)
FAB-MS (m/z): 692 (M+H)$^+$
$^1$H-NMR (300 MHz, DMSO-d$_6$), δ (ppm): 11.01 (1H, s), 10.70 (1H, s), 10.45 (1H, s), 10.05 (1H, s), 8.75 (1H, d, J=7.4 Hz), 8.47 (1H, d, J=7.4 Hz), 7.21 (2H, t, J=7.4 Hz), 7.00–7.10 (3H, m), 6.26 (1H, d, J=6.7 Hz), 5.44 (1H, d, J=5.9 Hz), 5.39 (1H, brs), 5.24 (1H, d, J=5.9 Hz), 4.93 (1H, d, J=5.9 Hz), 4.31 (1H, dd, J=6.7, 11.9 Hz), 4.22 (1H, t, J=6.7 Hz), 4.10 (1H, ddd, J=6.7, 6.7, 11.9 Hz), 4.05 (2H, m), 3.91 (1H, t, J=6.7 Hz), 3.76 (1H, m), 3.57–3.71 (2H, m), 3.40 (1H, m), 1.45 (3H, s), 1.36 (3H, s)

EXAMPLE 32

The compound represented by the formula

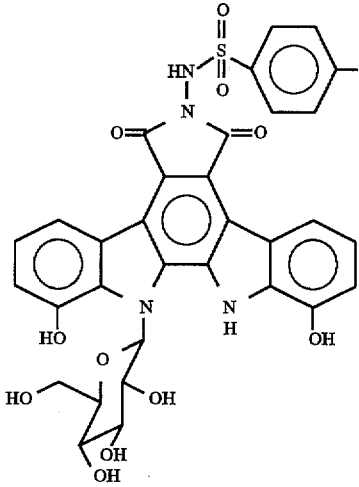

(34)

25 mg of the compound obtained in Example 1 was dissolved in 5 ml of anhydrous tetrahydrofuran, 10 mg of p-toluenesulfonic anhydride was added, and the mixture was stirred at room temperature for 1 day. The reaction solution was concentrated to dryness, and the residue was dissolved in 1 ml of methanol, subjected to a chromatograph tower of Sephadex LH-20 (1.8×20 cm) and eluted with methanol. The fractions containing the desired product were concentrated to dryness to give 12.3 mg of the captioned compound represented by the formula (34).

Rf value: 0.49 (produced by Merck Co., Kiesel gel $60F_{254}$, developing solvent; chloroform:methanol:tetrahydrofuran=3:1:1)

FAB-MS (m/z): 688 (M+H)$^+$ $^1$H-NMR (300 MHz, DMSO-d$_6$), δ (ppm): 10.98 (1H, s), 10.87 (1H, s), 10.42 (1H, s), 10.05 (1H, s), 8.54 (1H, d, J=7.9 Hz), 8.38 (1H, d, J=7.9 Hz), 7.84 (2H, d, J=8.7 Hz), 7.44 (1H, d, J=8.7 Hz), 7.19 (2H, t, J=7.9 Hz), 7.00–7.08 (3H, m), 5.43 (1H, d, J=4.7 Hz), 5.35 (1H, brs), 5.23 (1H, d, J=4.9 Hz), 4.90 (1H, d, J=4.4 Hz), 4.04 (2H, m), 3.75 (1H, m), 3.55–3.70 (2H, m), 3.40 (1H, m), 2.42 (3H, s)

EXAMPLE 33

The compound represented by the formula

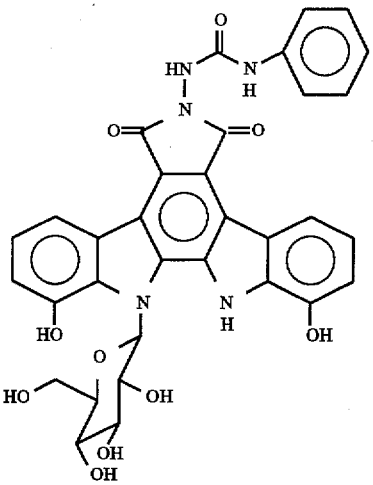

(35)

20 mg of the compound obtained in Example 1 was dissolved in 2 ml of tetrahydrofuran, 0.1 ml of phenyl isocyanate was added, and the mixture was stirred at room temperature for 2 hours. The reaction solution was concentrated to dryness, and the residue was dissolved in 1 ml of methanol, subjected to a chromatograph tower of Sephadex LH-20 (1.6×30 cm) and eluted with methanol. The fractions containing the desired product were concentrated to dryness to give 12 mg of the captioned compound represented by the formula (35).

Rf value: 0.38 (produced by Merck Co., Kiesel gel $60F_{254}$, developing solvent; chloroform:methanol:tetrahydrofuran=2:1:1)

FAB-MS (m/z): 653 (M+H)$^+$ $^1$H-NMR (400 MHz, DMSO-d$_6$), δ (ppm): 11.00 (1H, s), 10.40 (1H, brs), 10.10 (1H, brs), 9.48 (1H, s), 9.50 (1H, s), 8.67 (1H, d, J=8.3 Hz), 8.50 (1H, d, J=8.3 Hz), 7.48 (2H, d, J=7.8 Hz), 7.27 (2H, t, J=7.8 Hz), 7.20 (2H, t, J=7.8 Hz), 6.95–7.10 (4H, m), 5.43 (1H, d, J=4.2 Hz), 5.30 (1H, brs), 5.23 (1H, brs), 4.95 (1H, brs), 4.03 (2H, m), 3.75 (1H, m), 3.58–3.70 (2H, m), 3.38 (1H, m)

EXAMPLE 34

The compound represented by the formula

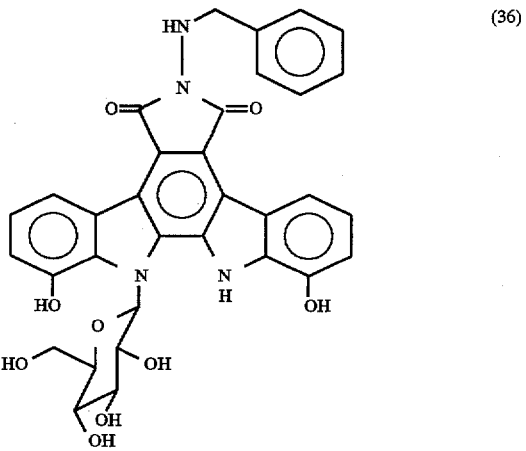

(36)

15 mg of the compound obtained in Example 1 was dissolved in 2 ml of tetrahydrofuran, 16 µl of benzoyl chloride was added, and the mixture was stirred at room temperature for 2 hours. The solvent was distilled away, and the residue was dissolved in 1 ml of methanol, subjected to a chromatograph tower of Sephadex LH-20 (1.6×20 cm) and eluted with methanol. The fractions containing the desired product were concentrated to dryness to give 12 mg of the captioned compound represented by the formula (36).

Rf value: 0.57 (produced by Merck Co., Kiesel gel 60F$_{254}$, developing solvent; chloroform:methanol:tetrahydrofuran=2:1:1)

FAB-MS (m/z): 639 (M+H)$^+$ $^1$H-NMR (200 MHz, DMSO-d$_6$), δ (ppm): 11.35 (1H, brs), 11.04 (1H, s), 10.45 (1H, brs), 10.08 (1H, brs), 8.66 (1H, d, J=8 Hz), 8.49 (1H, d, J=8.5 Hz), 8.04 (2H, d, J=7.1 Hz), 7.55–7.78 (3H, m), 7.20 (2H, t, J=8.5 Hz), 7.00–7.15 (3H, m), 5.45 (2H, brs), 5.25 (1H, brs), 4.97 (1H, brs), 4.02 (2H, m), 3.55–3.82 (3H, m), 3.41 (1H, m)

EXAMPLE 35

The compound represented by the formula

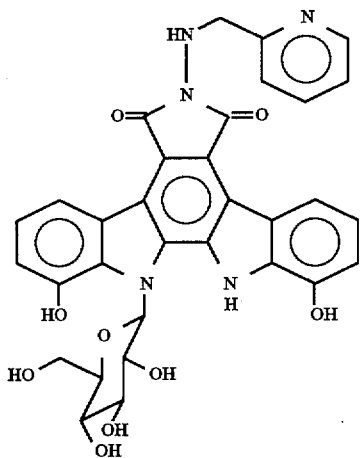

(37)

25 mg of the compound obtained in Example A was dissolved in 1.5 ml of N,N-dimethylformamide, 30 mg of α-picolinohydrazide was added, and the mixture was stirred at 80° C. for 2 hours. This was mixed with 50 ml of ethyl acetate, and the mixture was washed successively with water and then saturated saline, dehydrated with anhydrous sodium sulfate, and concentrated to dryness. The residue was dissolved in 1 ml of methanol, subjected to a chromatograph tower of Sephadex LH-20 (1.8×15 cm) and eluted with methanol. The fractions containing the desired product were concentrated to dryness to give 30 mg of the captioned compound represented by the formula (37).

Rf value: 0.58 (produced by Merck Co., Kiesel gel 60F$_{254}$, developing solvent; chloroform:methanol:tetrahydrofuran=2:1:1)

FAB-MS (m/z): 640 (M+H)$^+$ $^1$H-NMR (300 MHz, DMSO-d$_6$), δ (ppm): 11.43 (1H, s), 11.02 (1H, s), 10.45 (1H, s), 10.07 (1H, s), 8.82 (1H, d, J=4.2 Hz), 8.75 (1H, d, J=7.3 Hz), 8.48 (1H, d, J=7.8 Hz), 8.12 (2H, m), 7.75 (1H, m), 7.20 (2H, t, J=7.0 Hz), 7.00–7.15 (3H, m), 5.45 (1H, d, J=6.3 Hz), 5.40 (1H, brs), 5.25 (1H, d, J=6.3 Hz), 4.96 (1H, brs), 4.04 (2H, m), 3.76 (1H, m), 3.55–3.72 (2H, m), 3.42 (1H, m)

EXAMPLE 36

The compound represented by the formula

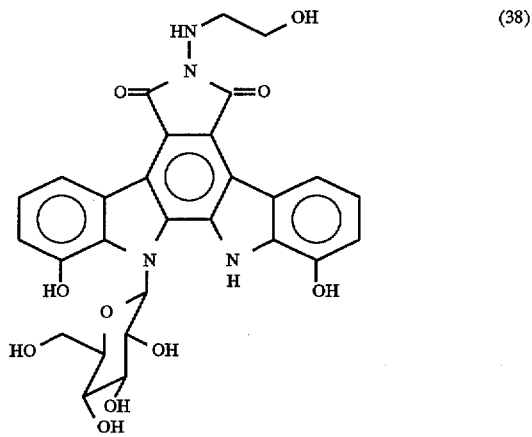

(38)

30 mg of the compound obtained in Example A was dissolved in 1 ml of N,N-dimethylformamide, 30 mg of 2-hydrazinoethanol was added, and the mixture was stirred at 80° C. for 2 hours. This was concentrated to dryness. The residue was dissolved in 1 ml of methanol, subjected to a chromatograph tower of Sephadex LH-20 (1.8×20 cm) and eluted with methanol. The fractions containing the desired product were concentrated to dryness to give 32 mg of the captioned compound represented by the formula (38).

Rf value: 0.32 (produced by Merck Co., Kiesel gel 60F$_{254}$, developing solvent; chloroform:methanol=2:1)

$^1$H-NMR (300 MHz, DMSO-d$_6$), δ (ppm): 10.91 (1H, s), 10.35 (1H, brs), 9.98 (1H, brs), 8.70 (1H, d, J=6.7 Hz), 8.53 (1H, d, J=6.9 Hz), 7.18 (2H, t, J=7.6 Hz), 6.99–7.06 (3H, m), 5.76 (1H, t, J=5.2 Hz), 5.41 (1H, d, J=5.6 Hz), 5.32 (1H, brs), 5.20 (1H, d, J=5.2 Hz), 4.90 (1H, brs), 4.51 (1H, t, J=4.9 Hz), 3.96–4.06 (2H, m), 3.73 (1H, m), 3.55–3.70 (4H, m), 3.39 (1H, m), 3.12 (2H, m)

EXAMPLE 37

The compound represented by the formula

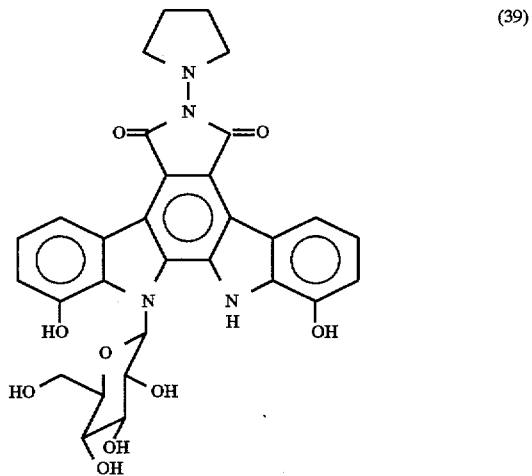

(39)

40 mg of the compound obtained in Example A was dissolved in 2 ml of N,N-dimethylformamide, 10 mg of 1-aminopyrrolidine hydrochloride and 0.1 ml of sodium bicarbonate aqueous solution were added, and the mixture was stirred at 80° C. for 2 hours. 40 ml of water was added thereto and the mixture was extracted with ethyl acetate (40 ml×2). The resultant ethyl acetate layer was dehydrated with anhydrous sodium sulfate, and concentrated to dryness. The residue was dissolved in 1 ml of methanol, subjected to a chromatograph tower of Sephadex LH-20 (1.8×20 cm) and eluted with methanol. The fractions containing the desired product were concentrated to dryness to give 10.0 mg of the captioned compound represented by the formula (39).

Rf value: 0.33 (produced by Merck Co., Kiesel gel 60F$_{254}$, developing solvent; chloroform:methanol=4:1)
FAB-MS (m/z): 589 (M+H)$^+$
$^1$H-NMR (300 MHz, DMSO-d$_6$), δ (ppm): 10.91 (1H, s), 10.35 (1H, s), 9.95 (1H, s), 8.78 (1H, d, J=8.3 Hz), 8.52 (1H, d, J=8.3 Hz), 7.16 (2H, t, J=7.6 Hz), 6.98–7.06 (3H, m), 5.40 (1H, d, J=5.5 Hz), 5.33 (1H, t, J=5.7 Hz), 5.18 (1H, d, J=5.5 Hz), 4.85 (1H, d, J=4.8 Hz), 4.02 (2H, m), 3.74 (1H, m), 3.53–3.68 (2H, m), 3.30–3.42 (5H, m), 1.97 (4H, m)

EXAMPLE 38

The compound represented by the formula

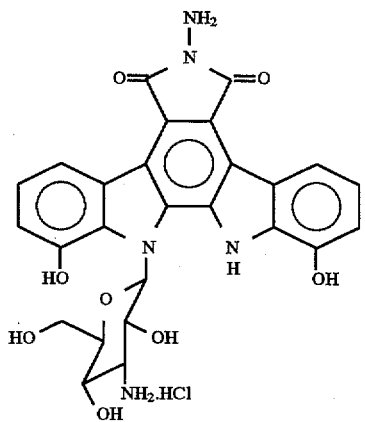

(40)

90 mg of 6-benzyloxymethyl-1,11-dibenzyloxy-12,13-dehydro-5H-indolo[2,3-a]pyrrolo[3,4-c]carbazole-4,7(6H)-dione, a compound disclosed in PCT/WO91/18003, 1.3 g of silver oxide and 550 mg of 4 Å molecular sieve were suspended in 30 ml of anhydrous benzene. After reflux with heating for 20 minutes, a solution of 416.4 mg of α-bromo-3-deoxy-3-azido-2,4,6-trtacetyl-D-glucose in 5 ml of anhydrous benzene was added dropwise over a period of 10 minutes. After further reflux with heating for 2 days, the insoluble matters were filtered using Celite. The filtrate was concentrated to dryness, and the residue was dissolved in 150 ml of ethyl acetate, washed successively with 0.2N hydrochloric acid, water and then saturated saline, dehydrated with anhydrous sodium sulfate, and concentrated to dryness. The residue was dissolved in 5 ml of chloroform, subjected to a chromatograph tower of Sephadex LH-20 (3.0×80 cm) and eluted with chloroform. The fractions containing the desired product were concentrated to dryness, and the residue was purified by preparative thin layer chromatography [n-hexane:acetone:tetrahydrofuran=3:1:0.1 (Rf: 0.5), then toluene:acetone=10:1 (Rf: 0.5)] to give 9.2 mg of 6-benzyloxymethyl-1,11-dibenzyloxy-12,13-dehydro-13-(β-D-glucopyranosyl)-5H-indolo[2,3-a]pyrrolo-[3,4-c]carbazole-5,7(6H)-dione.

9.2 mg of the resultant compound was dissolved in 1 ml of hydrazine monohydrate, and the solution was stirred at room temperature for 4 hours. This was mixed with 30 ml of ethyl acetate, and the mixture was washed successively with 0.2N hydrochloric acid, water and then saturated saline, dehydrated with anhydrous sodium sulfate, and concentrated to dryness. The residue was dissolved in 0.5 ml of tetrahydrofuran—1 ml of methanol, palladium black was added, and the mixture was stirred, under a hydrogen stream, at room temperature for 3 hours. The insoluble matters were filtered using Celite, 1.5 ml of 10% hydrogen chloride-methanol was added to the filtrate, and the mixture was concentrated to dryness. The residue was dissolved in 0.5 ml of methanol, subjected to a chromatograph tower of Sephadex LH-20 (1.0×15 cm) and eluted with methanol. The fractions containing the desired product were concentrated to dryness to give 2.0 mg of the captioned compound represented by the formula (40).

Rf value: 0.5 (produced by Merck Co., Kiesel gel 60F$_{254}$, developing solvent; n-butanol:acetic acid:water=4:1:1)
FAB-MS (m/z): 534 (M+H)$^+$
$^1$H-NMR (400 MHz, DMSO-d$_6$), δ (ppm): 10.80 (1H, s), 10.48 (1H, s), 10.20 (1H, s), 8.79 (1H, d, J=7.9 Hz), 8.52 (3H, br), 8.50 (1H, d, J=9.2 Hz), 7.61 (1H, d, J=6.6 Hz), 7.16 (1H, dd, J=9.2, 9.2 Hz), 7.10 (1H, dd, J=9.2, 9.2 Hz), 7.05 (1H, dd, J=9.2, 9.2 Hz), 7.00 (1H, dd, J=9.2, 9.2 Hz), 6.42 (1H, d, J=5.2 Hz), 6.16 (1H, d, J=3.9 Hz), 5.18 (1H, br), 4.93 (1H, br), 4.40 (1H, m), 4.16 (1H, m), 4.03 (1H, m), 3.78 (1H, m), 8.68 (1H, m), 3.42 (1H, m)

EXAMPLE 39

The compound represented by the formula

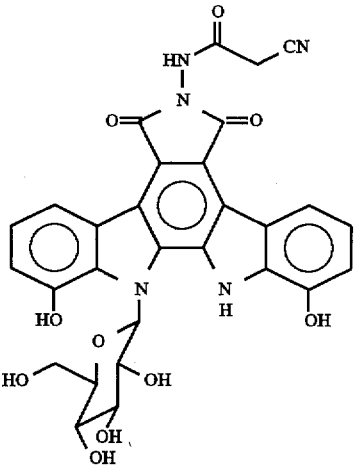

(41)

30 mg of the compound obtained in Example A was dissolved in 1.5 ml of N,N-dimethylformamide, 60 mg of cyanoacetohydrazide was added, and the mixture was stirred at 80° C. for 9 hours. This was mixed with 30 ml of ethyl acetate, the mixture was washed successively with water and then saturated saline, and the ethyl acetate layer was dehydrated with anhydrous sodium sulfate and concentrated to dryness. The residue was dissolved in a small quantity of methanol, subjected to a chromatograph tower of Sephadex LH-20 (1.5×15 cm) and eluted with methanol. The fractions containing the desired product were concentrated to dryness to give 27.8 mg of the captioned compound represented by the formula (41).

Rf value: 0.53 (produced by Merck Co., Kiesel gel 60F$_{254}$, developing solvent; chloroform:methanol:tetrahydrofuran=3:1:0.1)
FAB-MS (m/z): 601 (M+H)$^+$
$^1$H-NMR (300 MHz, DMSO-d$_6$), δ (ppm): 11.14 (1H, s), 11.01 (1H, s), 10.42 (1H, s), 10.04 (1H, s), 8.65 (1H, d, J=7.6 Hz), 8.47 (1H, d, J=7.6 Hz), 7.21 (2H, t, J=7.6 Hz), 7.05 (3H, t, J=7.6 Hz), 5.41 (2H, d, J=4.5 Hz), 5.19 (1H, d, J=6.8 Hz), 4.90 (1H, d, J=6.8 Hz), 4.13 (2H, s), 4.04 (2H, br), 3.75 (1H, m), 3.64 (2H, m), 3.43 (1H, m)

EXAMPLE 40

The compound represented by the formula

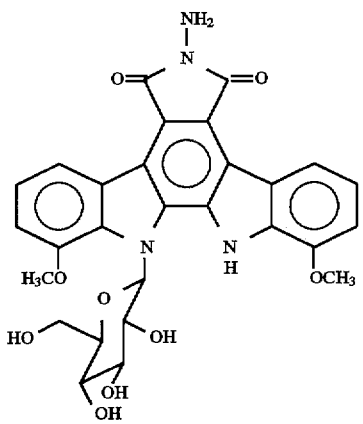
(42)

1 g of 12,13-dihydro-1,11-dihydroxy-13-(β-D-glucopyranosyl)-5H-indolo[2,3-a]pyrrolo[3,4-c]carbazole-5,7(6H)-dione was dissolved in 25 ml of tetrahydrofuran, an ether solution of an excessive quantity of diazomethane was added, the mixture was stirred at 4° C. overnight, and the formed yellow precipitate was collected by filtration. This was dissolved in 3 ml of hydrazine monohydrate, and the solution was subjected to reaction at room temperature for 1.5 hours. After the reaction, 200 ml of purified water was added, and the resultant precipitate was collected by filtration, washed successively with purified water and then methanol, and dried under reduced pressure to give 683.4 mg of the captioned compound represented by the formula (42).

HPLC; Rt, 10.5 minutes (column: Chromatolex ODS, inner diameter 4.6 mm, length 250 mm, detection; UV 305 nm, flow rate; 1 ml/minute, moving phase; methanol:water=6:4)

FAB-MS (m/z): 563 (M+H)$^+$ $^1$H-NMR (300 MHz, DMSO-d$_6$), δ (ppm): 10.9 (1H, s), 8.87 (1H, d, J=7.8 Hz), 8.65 (1H, d, J=7.8 Hz), 7.35 (1H, t, J=7.8 Hz), 7.23 (1H, t, J=7.8 Hz), 7.25 (1H, d, J=7.8 Hz), 7.18 (1H, d, J=7.8 Hz), 6.90 (1H, d, J=9.3 Hz), 5.40 (1H, brs), 5.18 (1H, brs), 5.00 (2H, brs), 4.90 (2H, brs), 4.06 (6H, s), 4.00 (2H, m), 3.78 (1H, m), 3.63 (2H, m), 3.42 (1H, m)

EXAMPLE 41

The compound represented by the formula

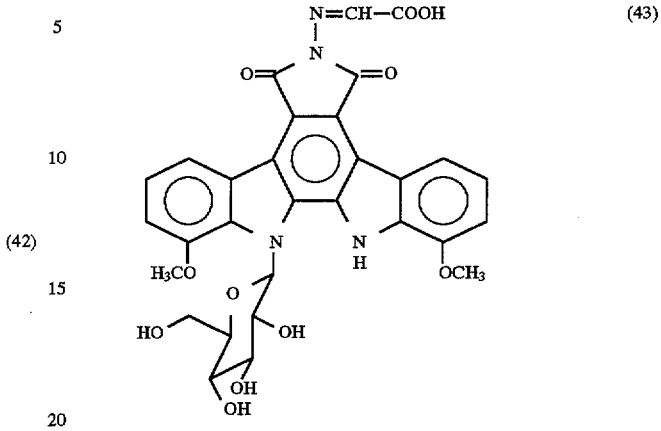
(43)

708.8 mg of the captioned compound represented by the formula (43) was obtained from 679 mg of the compound obtained in Example 40, according to the process of Example 2.

HPLC; Rt, 10.9 minutes (column: Chromatolex ODS, inner diameter 4.6 mm, length 250 mm, detection; UV 310 nm, flow rate; 1 ml/minute, moving phase; acetonitrile:water=2.8→acetonitrile:water=6:4, 30 minutes linear gradient)

FAB-MS (m/z): 618 [M]$^+$ $^1$H-NMR (400 MHz, DMSO-d$_6$), δ (ppm): 13.5 (1H, brs), 11.1 (1H, s), 9.01 (1H, s), 8.83 (1H, d, J=7.8 Hz), 8.63 (1H, d, J=7.8 Hz), 7.39 (1H, t, J=7.8 Hz), 7.37 (1H, t, J=7.8 Hz), 7.29 (1H, d, J=7.8 Hz), 7.22 (1.H, d, J=7.8 Hz), 6.94 (1H, d, J=9.3 Hz), 5.43 (1H, d, J=5.4 Hz), 5.22 (1H, d, J=5.4 Hz), 5.01 (1H, brs), 4.93 (1H, d, J=5.4 Hz), 4.07 (6H, s), 4.05 (1H, m), 3.96 (1H, m), 3.79 (1H, m), 3.60 (2H, m), 3.44 (1H, m)

EXAMPLE 42

The compound represented by the formula

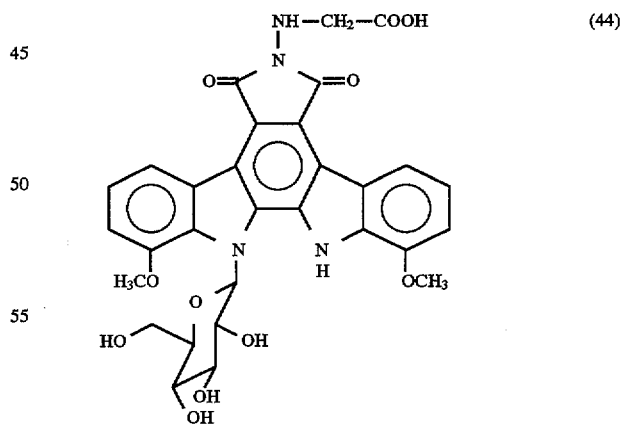
(44)

704 mg of the compound obtained in Example 41 was dissolved in 10 ml of N,N-dimethylformamide, 60 mg of 10 % palladium-carbon (Pd-C) was added, and the mixture was subjected to hydrogenation at room temperature for 6 hours under stirring. The reaction mixture was filtered using a sheet of filter paper on which Celite was spread to remove Pd-C, 200 ml of ethyl acetate was added to the filtrate, and the mixture was extracted with 50 ml of sodium bicarbonate aqueous solution (pH 8). The water layer was adjusted to pH 2 and extracted with ethyl acetate (500 ml). The ethyl acetate layer was extracted with 2% sodium bicarbonate aqueous solution (70 ml). The 2% sodium bicarbonate aqueous solution layer was concentrated under reduced pressure, adsorbed on a column of Dialon HP 20 (inner diameter 3 cm, length 30 cm), washed with water, and then eluted with 300 ml of methanol. The methanol eluate was concentrated to dryness, the residue was dissolved in a small quantity of N,N-dimethylformamide, and the solution was subjected to preparative HPLC (column: Chromatolex ODS, inner diameter 20 mm, length 250 mm, detection; UV 310 nm, flow rate; 9 ml/minute, moving phase; acetonitrile:water=25:75). The fractions containing the desired product were concentrated to dryness, and the residue was dissolved in a small quantity of water, subjected to column chromatography of Sephadex G-15 (inner diameter 3 cm, length 63 cm) and eluted with water:methanol=9:1. The fractions containing the desired product were concentrated and then freeze dried to give 84.2 mg of the sodium salt of the captioned compound represented by the formula (44).

HPLC; Rt, 8.9 minutes (column: Chromatolex ODS, inner diameter 4.6 mm, length 250 mm, detection; UV 310 nm, flow rate; 1 ml/minute, moving phase; acetonitrile:water:trifluoroacetic acid=300:700:1)

FAB-MS (m/z): 643 (M+Na)$^+$ $^1$H-NMR (400 MHz, DMSO-d$_6$), δ (ppm): 10.9 (1H, brs), 8.85 (1H, d, J=7.8 Hz), 8.63 (1H, d, J=7.8 Hz), 7.33 (1H, t, J=7.8 Hz), 7.31 (1H, t, J=7.8 Hz), 7.24 (1H, d, J=7.8 Hz), 7.16 (1H, d, J=7.8 Hz), 6.89 (1H, d, J=9.3 Hz), 5.63 (1H, brs), 5.42 (1H, brs), 5.10 (1H, brs), 4.99 (1H, brs), 4.06 (6H, s), 4.02 (2H, m), 3.80 (1H, m), 3.67 (1H, J=8.8 Hz), 3.58 (1H, m), 3.42 (1H, t, J=8.3 Hz), 3.34 (2H, s)

EXAMPLE 43

The compound represented by the formula

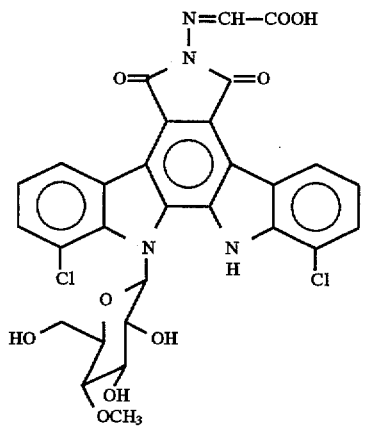

(45)

23.8 mg of the captioned compound represented by the formula (45) was obtained from 70 mg of the compound obtained in Example 4, according to the same process as in Example 2.

FAB-MS (m/z): 641 (M+H)$^+$ $^1$H-NMR (400 MHz, DMSO-d$_6$), δ (ppm): 10.8 (1H, s), 9.26 (1H, d, J=7.8 Hz), 9.09 (1H, d, J=7.8 Hz), 8.94 (1H, s), 7.78 (1H, d, J=7.8 Hz), 7.74 (1H, d, J=7.8 Hz), 7.50 (2H, t, J=7.8 Hz), 6.98 (1H, d, J=9.3 Hz), 5.44 (1H, d, J=5.9 Hz), 5.33 (1H, brs), 5.09 (1H, d, J=5.4 Hz), 3.96 (2H, m), 3.85 (1H, m), 3.67 (2H, m), 3.59 (3H, s), 3.56 (1H, m)

EXAMPLE 44

The compound represented by the formula

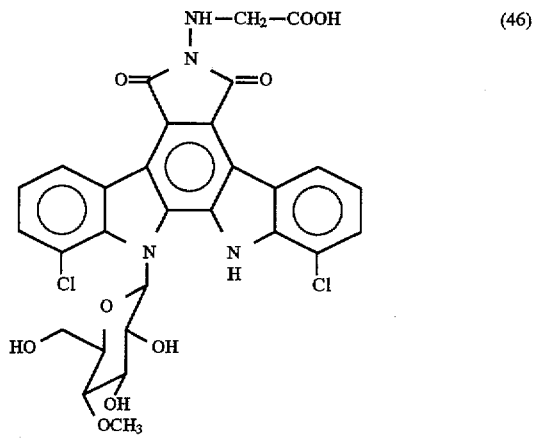

(46)

210 mg of the captioned compound represented by the formula (46) was obtained from 1 g of the compound obtained in Example 43, according to the same process as in Example 42.

FAB-MS (m/z): 643 (M+H)$^+$ $^1$H-NMR (500 MHz, DMSO-d$_6$), δ (ppm): 10.7 (1H, s), 9.26 (1H, d, J=7.8 Hz), 9.09 (1H, d, J=7.8 Hz), 7.74 (1H, d, J=7.8 Hz), 7.71 (1H, d, J=7.8 Hz), 7.46 (2H, t, J=7.8 Hz), 6.93 (1H, d, J=9.2 Hz), 6.00 (1H, brs), 5.42 (1H, brs), 5.31 (1H, brs), 5.03 (1H, brs), 3.96 (2H, brs), 3.85 (2H, s), 3.83 (1H, m), 3.59 (3H, s), 3.50–3.70 (3H, m)

EXAMPLE 45

The compound represented by the formula

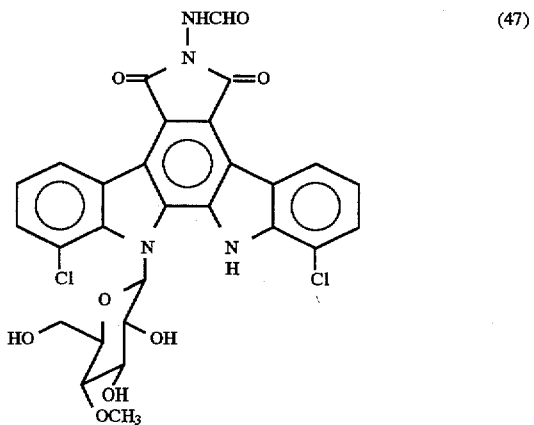

(47)

48.2 mg of the captioned compound represented by the formula (47) was obtained from 51.4 mg of the compound obtained in Example 4, according to the same process as in Example 5.

FAB-MS (m/z): 613 (M+H)$^+$ $^1$H-NMR (400 MHz, DMSO-d$_6$), δ (ppm): 10.9 (1H, brs), 10.8 (1H, brs), 9.20 (1H, m), 9.03 (1H, m), 8.48 (1H, s), 7.75 (1H, d, J=7.8 Hz), 7.70 (1H, d, J=7.8 Hz), 7.45 (2H, t, J=7.8 Hz), 6.93 (1H, brt, J=9.3 Hz), 5.41 (2H, m), 5.04 (1H, d, J=5.9 Hz), 3.99 (2H, brs), 3.86 (1H, m), 3.60 (3H, s), 3.52–3.67 (3H, m)

EXAMPLE 46

The compound represented by the formula

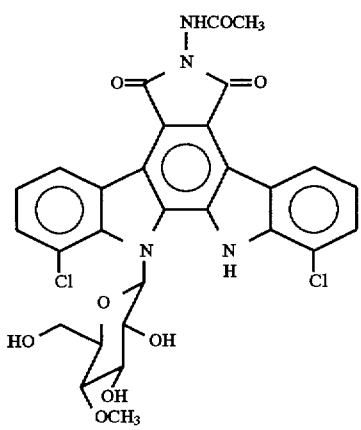

(48)

13 mg of the captioned compound represented by the formula (48) was obtained from 14.1 mg of the compound obtained in Example 4, according to the same process as in Example 6.

FAB-MS (m/z): 627 (M+H)$^+$ $^1$H-NMR (500 MHz, DMSO-d$_6$), δ (ppm): 10.8 (2H, s), 9.20 (1H, m), 9.04 (1H, m), 7.74 (2H, m), 7.47 (2H, m), 6.93 (1H, m), 5.41 (1H, m), 5.32 (1H, brs), 5.04 (1H, m), 3.96 (2H, brs), 3.85 (1H, m), 3.58 (3H, s), 3.50–3.70 (3H, m), 2.12 (3H, s)

EXAMPLE 47

The compound represented by the formula

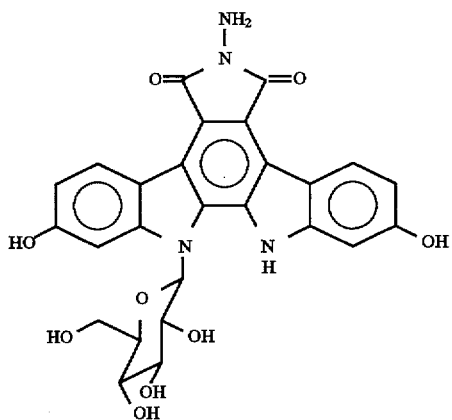

(49)

1 ml of hydrazine monohydrate was added to 3.2 mg of 12,13-dihydro-2,10-dihydroxy-13-(β-D-glucopyranosyl)-5H-indolo[2,3-a]pyrrolo[3,4-c]carbazole-5,7(6H)-dione, and the mixture was stirred at room temperature for 2 hours. This was distributed with ethyl acetate-0.2N hydrochloric acid, and the ethyl acetate layer was washed successively with water then saturated saline, and concentrated to dryness. The residue was dissolved in a small quantity of methanol, subjected to a chromatograph tower of Sephadex LH-20 (1.0×5 cm) and eluted with methanol. The fractions containing the desired product were concentrated to dryness to give 3.0 mg of the captioned compound represented by the formula (49).

Rf value: 0.22 (produced by Merck Co., Kiesel gel 60F$_{254}$, developing solvent; chloroform:methanol:tetrahydrofuran=3:1:1)

FAB-MS (m/z): 534 [M]$^+$ $^1$H-NMR (300 MHz, DMSO-d$_6$), δ (ppm): 11.16 (1H, s), 9.76 (1H, s), 9.73 (1H, s), 8.90 (1H, d, J=7.3 Hz), 8.82 (1H, d, J=7.3 Hz), 7.18 (1H, d, J=2.0 Hz), 6.98 (1H, d, J=2.0 Hz), 6.83 (2H, dt, J=2.0, 7.3 Hz), 5.97 (1H, d, J=7.2 Hz), 5.84 (1H, t, J=3.3 Hz), 5.32 (1H, d, J=5.3 Hz), 5.10 (1H, d, J=5.3 Hz), 4.93 (1H, d, J=5.2 Hz), 4.90 (2H, s), 4.04–3.86 (2H, m), 3.78 (1H, m), 3.60–3.35 (3H, m)

EXAMPLE 48

The compound represented by the formula

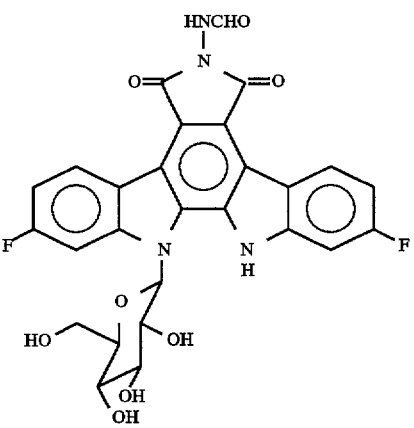

(50)

0.4 ml of hydrazine hydrate was added to 7.1 mg of 2,10-difluoro-12,13-dihydro-13-(β-D-glucopyranosyl)-5H-indolo[2,3-a]pyrrolo[3,4-c]carbazole-5,7(6H)-dione, and the mixture was stirred at room temperature for 40 minutes. 1.34 ml of concentrated hydrochloric acid was added thereto, and the mixture was extracted with ethyl acetate. The ethyl acetate layer was washed with water and concentrated. The residue was dissolved in 3.7 ml of N,N-dimethylformamide and 0.37 ml of concentrated hydrochloric acid, and the solution was stirred at room temperature overnight. This was distributed between ethyl acetate and water, and the ethyl acetate layer was concentrated to dryness. The residue was dissolved in a small quantity of ethanol, subjected to a chromatograph tower of Sephadex LH-20 and eluted with ethanol. The fractions containing the desired product were concentrated to dryness to give 4.6 mg of the captioned compound represented by the formula (50).

FAB-MS (m/z): 566 [M]$^+$ $^1$H-NMR (400 MHz, DMSO-d$_6$), δ (ppm): 11.9 (1H, s), 10.8 (1H, brs), 9.07 (1H, dd, J=5.8, 8.8 Hz), 9.01 (1H, dd, J=5.9, 8.8 Hz), 8.45 (1H, s), 7.93 (1H, brd, J=8.8 Hz), 7.44 (1H, brd, J=8.8 Hz), 7.27 (2H, m), 6. 28 (1H, d, J=8.8 Hz), 6.20 (1H, brs), 5.42 (1H, brs), 5.13 (1H, brd, J=5.4 Hz), 4.96 (1H, d, J=5.4 Hz), 4.09 (1H, brd, J=7.3 Hz), 3.94 (2H, m), 3.83 (1H, brd, J=7.3 Hz), 3.58 (1H, m), 3.45 (1H, m)

EXAMPLE 49

The compound represented by the formula

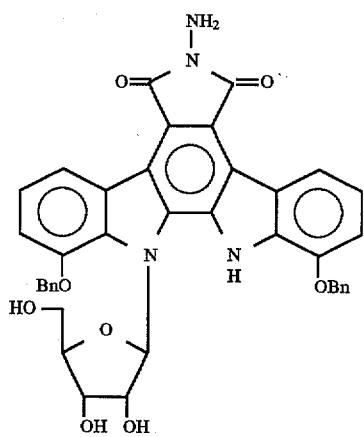
(51)

wherein Bn represents a benzyl group.

100 mg of 6-benzyloxymethyl-11,11-dibenzyloxy-12,13-dihydro-5H-indolo[2,3-a]pyrrolo[3,4-c]carbazole-5,7(6H)-dione, 1.4 g of silver oxide and 0.7 g of 4 Å molecular sieve were suspended in 40 ml of anhydrous benzene, the suspension was refluxed with heating for 20 minutes, and then a solution of 1-bromo-2,3,5-tri-O-acetyl-D-ribose in 10 ml of anhydrous benzene was added dropwise over a period of 10 minutes. The mixture was further refluxed with heating for 3 hours, and the insoluble matters were filtered using Celite.

The filtrate was concentrated to dryness, and the residue was dissolved in 100 ml of ethyl acetate and the solution was washed successively with 0.2N hydrochloric acid, water and then saturated saline, dried over anhydrous sodium sulfate, and concentrated to dryness. The residue was dissolved in chloroform, subjected to a chromatograph tower of Sephadex LH-20 (2.5×20 cm) and eluted with chloroform. The fractions containing the desired product were concentrated to dryness, the residue was subjected to a chromatograph tower of silica gel (2.5×25 cm) and eluted with toluene-ethyl acetate (3:1), and the fractions containing the desired product were concentrated to dryness. The residue was further purified by preparative thin layer chromatography (toluene-ethyl acetate=5:1 (Rf=0.6)) to give 20.8 mg of 6-benzyloxymethyl-1,11-dibenzyloxy-12,13-dihydro-13-(β-D-ribofuranosyl)-5H-indolo[2,3-a]pyrrolo[3,4-c]carbazole-5,7(6H)-dione.

20.8 mg of this compound was dissolved in 2 ml of hydrazine monohydrate, and the solution was stirred at room temperature for 2 hours. This was mixed with 30 ml of ethyl acetate, the mixture was washed successively with 0.2N hydrochloric acid, water and then saturated saline, and concentrated to dryness. The residue was dissolved in methanol, subjected to a chromatograph tower of Sephadex LH-20 (1.0×15 cm) and eluted with methanol. The fractions containing the desired product were concentrated to dryness, and the residue was purified by preparative thin layer chromatography (chloroform-methanol=10:1 (Rf=0.5)) to give 2.9 mg of the captioned compound represented by the formula (51).

Rf value: 0.5 (produced by Merck Co., Kiesel gel 60F$_{254}$, developing solvent; chloroform:methanol=10:1)

FAB-MS (m/z): 684 [M]$^+$ $^1$H-NMR (300 MHz, DMSO-d$_6$), δ (ppm): 10.45 (1H, s), 8.90 (1H, d, J=0.75 Hz), 8.68 (1H, d, J=0.75 Hz), 7.18 (2H, d, J=0.75 Hz), 7.11 (2H, d, J=0.75 Hz), 7.20–7.50 (11H, m), 5.35–5.45 (5H, m), 5.17 (1H, d, J=0.38 Hz), 5.10 (1H, d, J=0.45 Hz), 4.98 (2H, s), 3.90–4.00 (2H, m), 3.60–3.70 (2H, m)

EXAMPLE 50

The compound represented by the formula

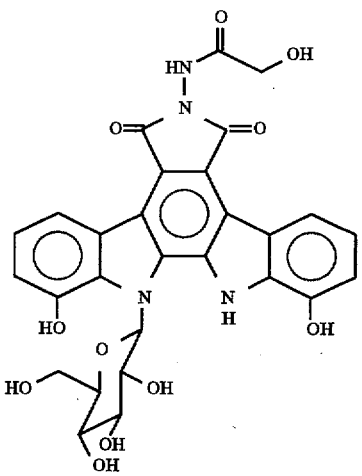
(52)

33.0 mg of the compound obtained in Example A was dissolved in 3 ml of N,N-dimethylformamide, 8.4 mg of hydroxyacetohydrazide was added, and the mixture was stirred at 80° C. for 2 days. This was concentrated to dryness, and the residue was dissolved in a small quantity of methanol, subjected to a chromatograph tower of Sephadex LH-20 (1.5×25 cm), and eluted with methanol. The fractions containing the desired product were concentrated to dryness, and the residue was dissolved in 30 ml of ethyl acetate. The solution was washed with water, and the ethyl acetate layer was dried over anhydrous sodium sulfate and concentrated to dryness. The residue was dissolved in a small quantity of methanol, subjected to a chromatograph tower of Sephadex LH-20 (1.5×15 cm) and eluted with methanol. The fractions containing the desired product were concentrated to dryness to give 29.0 mg of the captioned compound represented by the formula (52).

FAB-MS (m/z): 593 [M+H]$^+$ $^1$H-NMR (300 MHz, DMSO-d$_6$), δ (ppm): 11.00 (1H, s), 10.55 (1H, s), 10.41 (1H, s), 10.02 (1H, s), 8.68 (1H, d, J=7.8 Hz), 8.47 (1H, d, J=7.8 Hz), 7.20 (2H, t, J=7.8 Hz), 7.04 (3H, m), 5.88 (1H, t, J=7.0 Hz), 5.41 (1H, d, J=6.2 Hz), 5.35 (1H, br), 5.20 (1H, d, J=6.2 Hz), 4.90 (1H, d, J=6.2 Hz), 4.16 (2H, d, J=5.7 Hz), 4.03 (2H, m), 3.74 (1H, m), 3.59–3.68 (2H, m), 3.39 (1H, m)

EXAMPLE 51

The compound represented by the formula

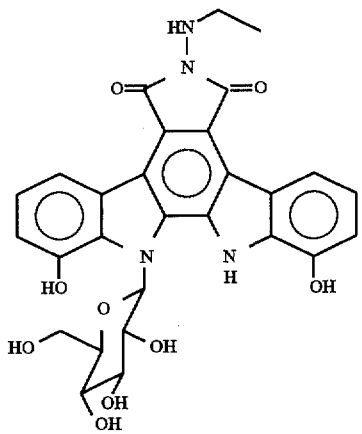

(53)

35.0 mg of the compound obtained in Example A was dissolved in 1.0 ml of N,N-dimethylformamide, 35.0 mg of ethylhydrazine oxalate and 0.5 ml of saturated sodium bicarbonate aqueous solution were added, and the mixture was stirred at 80° C. for 1 day. This was concentrated to dryness, and the residue was dissolved in a small quantity of methanol, subjected to a chromatograph tower of Sephadex LH-20 (1.5×15 cm) and eluted with methanol. The fractions containing the desired product were concentrated to dryness to give 20.8 mg of the captioned compound represented by the formula (53).

Rf value: 0.5 (produced by Merck Co., Kiesel gel $60F_{254}$, developing solvent; chloroform:methanol:tetrahydrofuran= 2:1:1)

FAB-MS (m/z): 563 $[M+H]^+$ $^1$H-NMR (300 MHz, DMSO-$d_6$), δ (ppm): 10.90 (1H, s), 10.35 (1H, s), 9.96 (1H, s), 8.72 (1H, d, J=7.9 Hz), 8.54 (1H, d, J=7.9 Hz), 7.17 (2H, t, J=7.9 Hz), 7.03 (3H, m), 5.72 (1H, t, J=4.8 Hz), 5.41 (1H, d, J=6.3 Hz), 5.35 (1H, t, J=4.0 Hz), 5.21 (1H, d, J=4.0 Hz), 4.87 (1H, d, J=6.3 Hz), 3.96–4.09 (2H, m), 3.73–3.77 (1H, m), 3.58–3.67 (2H, m), 3.37–3.45 (1H, m), 3.07 (2H, m), 1.09 (3H, t, J=7.1 Hz)

EXAMPLE 52

The compound represented by the formula

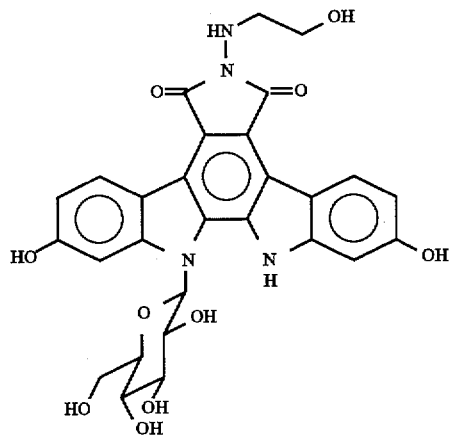

(54)

421.9 mg of the compound obtained in Example C was dissolved in 6.7 ml of N,N-dimethylformamide, 360 mg of 2-hydroxyethylhydrazine was added, and the mixture was stirred at 80° C. for 1.5 hours. The reaction mixture was concentrated to dryness, the residue was dissolved in a small quantity of methanol, and the solution was placed on a Sephadex LH-20 (6.5×50 cm) column for chromatography and eluted with methanol. Fractions containing the desired product were concentrated to dryness to give 189.3 mg of the captioned compound represented by the formula (54).

Rf value: 0.50 (produced by Merck Co., Kiesel gel 60 $F_{254}$, developing solvent; chloroform:methanol:tetrahydrofuran=3:1:1) FAB-MS (m/z) : 579 $(M+H)^+$ $^1$H-NMR (300 MHz, DMSO-$d_6$), δ (ppm): 11.20 (1H, s), 9.88 (1H, s), 9.85 (1H, s), 8.85 (1H, d, J=9.0 Hz), 8.79 (1H, d, J=9.0 Hz), 7.19 (1H, d, J=1.4 Hz), 6.98 (1H, d, J=1.4Hz), 6.82 (1H, dd, J=1.4 Hz, 9.0 Hz), 6.79 (1H, dd, J=1.4 Hz, 9.0 Hz), 5.98 (1H, d, J=9.0 Hz), 5.85 (1H, t, J=4.0 Hz), 5.73 (1H, t, J=3.4 Hz), 5.31 (1H, d, J=3.6 Hz), 5.10 (1H, d, J=6.3 Hz), 4.90 (1H, t, J=4.5 Hz), 3.87–4.10 (3H, m), 3.77–3.80 (1H, m), 3.49–3.60 (4H, m), 3.05–3.15 (2H, m)

EXAMPLE 53

The compound represented by the formula

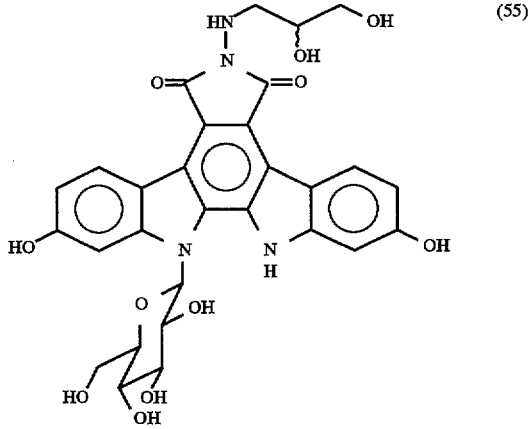

(55)

1) 6.73 g of DL-glyceraldehyde dimer and 9.87 g of carbazi acid tert-butyl ester were dissolved in 50 ml of 95% ethanol, and the solution was stirred at room temperature for 15 hours and then at 60° C. for 30 minutes. The reaction solution was concentrated under reduced pressure, and the residue was recrystallized from ethyl acetate to give 13.7 g of (2SR)-3-(tert-butyloxycarbonyl)hydrazono-1,2-propanediol as a colorless solid.

Rf value: 0.49 (produced by Merck Co., Kiesel gel 60 $F_{254}$, developing solvent; dichloromethane:methanol=10:2) $^1$H-NMR (300 MHz, DMSO-$d_6$), δ (ppm): 1.41 (9H, s), 3.39 (2H, m), 3.93 (1H, m), 4.65 (1H, t, J=5.8 Hz), 5.11 (1H, d, J=5.0 Hz), 7.16 (1H, d, J=6.0 Hz), 10.52 (1H, brs)

2) 52 ml of borane-tetrahydrofuran complex was added to 12.6 g of (2SR)-3-(tert-butyloxycarbonyl)hydrazono-1,2-propanediol at room temperature, and the mixture was stirred at room temperature for 10 minutes. 26 ml of 6N hydrochloric acid was added to the reaction solution at room temperature, and the mixture was stirred at 100° C. for 15 minutes. The reaction solution was concentrated under reduced pressure, and the residue was adsorbed on an $H^+$ type of Dowex 50 WX4, washed with water and eluted with 0.5N ammonia water. Fractions containing the desired product were combined and concentrated under reduced pressure, and the resultant oily matter was adsorbed on an $NH_4^+$ type of IRC-50 and eluted with water. Fractions containing the desired product were combined and concentrated under reduced pressure to give 2.2 g of (2SR)-3-hydrazino-1,2-propanediol as a colorless solid.

Rf value: 0.33 (producing by Merck Co., Kiesel gel 60 F$_{254}$, developing solvent; n-butanol:acetic acid:water=5:2:1)
FAB-MS (m/z): 107 (M+H)$^+$
$^1$H-NMR (300 MHz, DMSO-d$_6$), δ (ppm): 2.51 (1H, dd, J=7.3, 12.1 Hz), 2.66 (1H, dd, J=4.3, 12.1 Hz), 3.28 (2H, m), 3.56 (1H, m)

3) 500 mg of the compound obtained in Example C and 313 mg of (2SR)-3-hydrazino-1,2-propanediol obtained in 2) were dissolved in 10 ml of N,N-dimethylformamide, and the solution was shirred at 80° C. for 2.5 hours. The reaction solution was concentrated under reduced pressure, and the residue was purified by Sephadex LH20 (chloroform:methanol:ethanol:water=5:2:2:1) to give 462 mg of the captioned compound represented by the formula (55).

Rf value: 0.31 (produced by Merck Co., Kiesel gel 60 F$_{254}$, developing solvent; tetrahydrofuran:methanol:n-hexane:formic acid=10:2:4:0.1)
FAB-MS (m/z): 609 (M+H)$^+$
[α]$_D$+172° (c=1.02, DMSO)
$^1$H-NMR (300 MHz, DMSO-d$_6$), δ (ppm): 2.99 (1H, m), 3.07 (1H, m), 3.42 (2H, t, J=5.6 Hz), 3.50 (2H, m), 3.62 (1H, m), 3.78 (1H, m), 3.91 (2H), 4.01 (1H, m), 4.52 (1H, t, J=5.6 Hz), 4.60 (1H, d, J=4.4 Hz), 4.92 (1H, d, J=5.2 Hz), 5.12 (1H, d, J=5.2 Hz), 5.33 (1H, d, J=4.4 Hz), 5.71 (1H, dd, J=4.4 Hz, 5.6 Hz), 5.87 (1H, m), 5.97 (1H, d, J=8.5 Hz), 6.80 (1H, dd, J=2.0 Hz, 8.6 Hz), 6.83 (1H, dd, J=1.9 Hz, 8.6 Hz), 6.98 (1H, d, J=2.0 Hz), 7.18 (1H, d, J=1.9 Hz), 8.79 (1H, d, J=8.6 Hz), 8.87 (1H, d, J=8.6 Hz), 9.76 (1H, s), 9.78 (1H, s), 11.20 (1H, s)

EXAMPLE 54

The compound represented by the formula

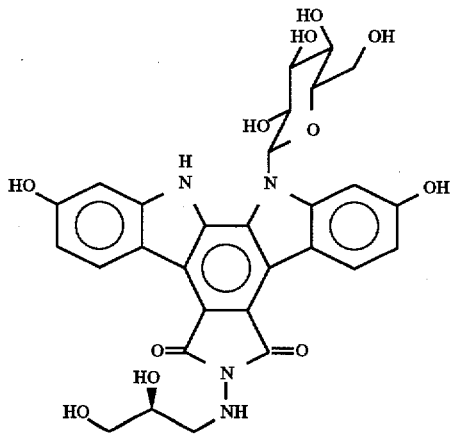

(56)

1) 3.45 g of D-(R)-glyceraldehyde acetonide and 3.50 g of carbazinic acid tert-butyl ester were dissolved in 20 ml of ethanol, and the solution was stirred at room temperature for 15 hours. The reaction solution was concentrated under reduced pressure, and the residue was recrystallized from ethyl acetate to give 5.65 g of (4S) -2,2-dimethyl-4-(tert-butyloxycarbonylhydrazono)methyl-1,3-dioxolane as a colorless solid.

Rf value: 0.56 (produced by Merck Co., Kiesel gel 60 F$_{254}$, developing solvent; n-hexane:ethyl acetate=1:1)
[α]$_D$+46.4° (c=1.00, CHCl$_3$)
$^1$H-NMR (300 MHz, CDCl$_3$), δ (ppm): 1.38 (3H, s), 1.43 (3H, s), 1.50 (9H, s), 3.87 (1H, dd, J=6.3 Hz, 8.6 Hz), 4.18 (1H, dd, J=6.6 Hz, 8.6 Hz), 4.65 (1H, ddd, J=6.4 Hz, 6.4 Hz, 6.4 Hz), 7.12 (1H, brd, J=5.9 Hz), 7.78 (1H, brs)

2) 18.4 ml of borane-tetrahydrofuran complex was added to 3.00 g of (4S)-2,2-dimethyl-4-(tert-butyloxycarbonylhydrazono)methyl-1,3-dioxolane at room temperature, and the mixture was stirred at room temperature for 10 minutes. 6.2 ml of 6N hydrochloric acid was added to the reaction solution at room temperature, and mixture was stirred at 100° C. for 15 minutes. The reaction solution was concentrated under reduced pressure, and the resultant residue was adsorbed on an H$^+$ type of Dowex 50 WX4, washed with water and eluted with 0.5N ammonia water. Fractions containing the desired product were combined and concentrated under reduced pressure, and the resultant oily matter was adsorbed on an NH$_4^+$ type of IRC-50 and eluted with water. Fractions containing the desired product were combined, and concentrated under reduced pressure to give 772 mg of (2S)-3-hydrazino-1,2-propanediol as a colorless solid.

Rf value: 0.33 (produced by Merck Co., Kiesel gel 60 F$_{254}$, developing solvent; n-butanol:acetic acid:water=5:2:1)

[α]$_D$−23.0° (c=1.00, MeOH)

$^1$H-NMR (300 MHz, CD$_3$OD), δ (ppm): 2.72 (1H, dd, J=8.2 Hz, 12.3 Hz), 2.87 (1H, dd, J=3.7 Hz, 12.3 Hz), 3.49 (2H, d, J=5.4 Hz), 3.77 (1H, m)

3) 500 mg of the compound obtained in Example C and 306 mg or (2S)-3-hydrazino-1,2-propanediol obtained in 2) were dissolved in 20 ml of N,N-dimethylformamide, and the solution was stirred at 80° C. for 3 hours. The reaction solution was concentrated under reduced pressure, and residue was purified by Sephadex LH20 (chloroform:methanol:ethanol:water=5:2:2:1) to give 340 mg or the captioned compound represented by the formula (56).

Rf value: 0.59 (produced by Merck Co., Kiesel gel 60 F$_{254}$, developing solvent; tetrahydrofuran:methanol:n-hexane:formic acid=10:2:2:0.1)

[α]$_D$+147° (c=1.00, DMSO)

FAB-MS; (M+H)$^+$; Found: 609, 1848, Calcd: 609, 1833

$^1$H-NMR (300 MHz, DMSO-d$_6$), δ (ppm): 2.98 (1H, m), 3.07 (1 H, m), 3.41 (2H, brt, J=5.7 Hz), 3.50 (2H, m), 3.63 (1H, m), 3.78 (1H, m), 3.85–3.96 (2H), 4.02 (1H, m), 4.52 (1H, t, J=5.7 Hz), 4.61 (1H, d, J=4.4 Hz), 4.93 (1H, d, J=5.1 Hz), 5.12 (1H, d, J=5.0 Hz), 5.34 (1H, d, J=4.8 Hz), 5.71 (1H, m), 5.87 (1H, t, J=4.5 Hz), 5.98 (1H, d, J=8.5 Hz), 6.80 (1H, dd, J=2.2 Hz, 8.7 Hz), 6.83 (1H, dd, J=2.0 Hz, 8.5 Hz), 6.98 (1H, d, J=2.0 Hz), 7.18 (1H, d, J=1.9 Hz), 8.78 (1H, d, J=8.7 Hz), 8.87 (1H, d, J=8.6 Hz), 9.76 (1H, s), 9.79 (1H, s), 11.20 (1H, s)

EXAMPLE 55

The compound represented by the formula

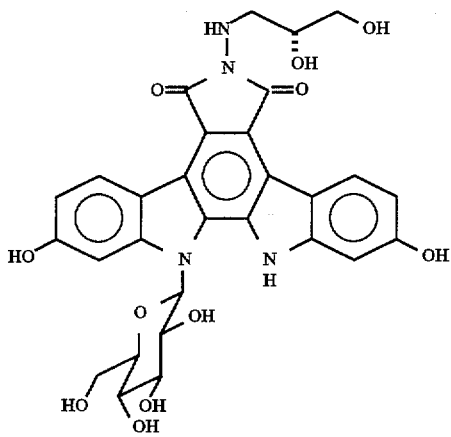

(57)

1) 8.5 g of (S)-(–)-glycidol was dissolved in 80 ml of ethanol, 45.5 g of carbazinic acid tert-butyl ester was added, and the mixture was stirred at room temperature for 3 days. The reaction solution was concentrated under reduced pressure, and the residue was purified by silica gel column chromatography (dichloromethane:methanol=10:1) to give 5.53 g of (2R)-3-(N'-tert-butyloxycarbonyl)hydrazino-1,2-propanediol as light yellow oily matter.

Rf value: 0.24 (produced by Merck Co., Kiesel gel 60 $F_{254}$, developing solvent; dichloromethane:methanol=10:1) $[\alpha]_D$+10.8° (c=1.00, MeOH)

$^1$H-NMR (300 MHz, $CD_3OD$), δ (ppm): 1.44 (9H, s), 2.75 (1H, dd, J=7.9 Hz, 12.3 Hz), 2.87 (1H, dd, J=4.2 Hz, 12.3 Hz), 3.51 (2H, m), 3.69 (1H, m)

2) 2.99 g of (2R)-3-(N'-tert-butyloxycarbonyl)hydrazino-1,2-propanediol was dissolved in 15 ml of tetrahydrofuran, 7.5 ml of 6N hydrochloric acid was added, and the mixture was stirred at 100° C. for 20 minutes. The reaction solution was concentrated under reduced pressure, and the resultant residue was adsorbed on an $H^+$ type of Dowex 50 WX4, washed with water and then eluted with 0.5N ammonia water. Fractions containing the desired product were combined and concentrated under reduced pressure, and the resultant oily matter was adsorbed on an $NH_4^+$ type of IRC-50 and eluted with water. Fractions containing the desired product were combined and concentrated under reduced pressure to give 993 mg of (2R)-3-hydrazino-1,2-propanediol as a colorless solid.

Rf value: 0.33 (produced by Merck Co., Kiesel gel 60 $F_{254}$, developing solvent; n-butanol:acetic acid:water=5:2:1) $[\alpha]_D$+20.6° (c=0.992, MeOH)

$^1$H-NMR (300 MHz, $CD_3OD$), δ (ppm): 2.72 (1H, dd, J=8.2, 12.4 Hz), 2.87 (1H, dd, J=3.7, 12.4 Hz), 3.49 (2H, d, J =5.5 Hz), 3.77 (1H, m)

3) 250 mg of the compound obtained in Example C and 129 mg of (2R)-3-hydrazino-1,2-propanediol obtained in 2) were dissolved in 7.5 ml of N,N-dimethylformamide, and the solution was stirred at 80° C. for 3 hours. The reaction solution was concentrated under reduced pressure, and the residue was purified by Sephadex LH20 (chloroform:methanol:ethanol:water=5:2:2:1) to give 172 mg of the captioned compound represented by the formula (57).

Rf value: 0.57 (produced by Merck Co., Kiesel gel 60 $F_{254}$, developing solvent; tetrahydrofuran:methanol:n-hexane:formic acid=10:2:2:0.1) $[\alpha]_D$+170° (c=0.50, DMSO)

FAB-MS; (M+H)$^+$; Found: 609, 1836, Calcd: 609, 1833

$^1$H-NMR (300 MHz, DMSO-$d_6$), δ (ppm): 2.98 (1H, m), 3.07 (1H, m), 3.42 (2H, br), 3.51 (2H, br), 3.62 (1H, br), 3.78 (1H, brd, J=10 Hz), 3.85–3.96 (2H), 4.02 (1H, m), 4.52 (1H, br), 4.60 (1H, br), 4.93 (1H, br), 5.13 (1H, br), 5.38 (1H, br), 5.72 (1H, t, J=4.8 Hz), 5.90 (1H, br), 5.97 (1H, d, J=8.2 Hz), 6.80 (1H, dd, J=2.1, 8.6 Hz), 6.83 (1H, dd, J=1.9 Hz, 8.6 Hz), 6.99 (1H, d, J=2.0 Hz), 7.18 (1H, d, J=1.8 Hz), 8.79 (1H, d, J=8.6 Hz), 8.87 (1H, d, J=8.6 Hz), 9.8 (2H, br), 11.20 (1H, s)

EXAMPLE 56

The compound represented by the formula

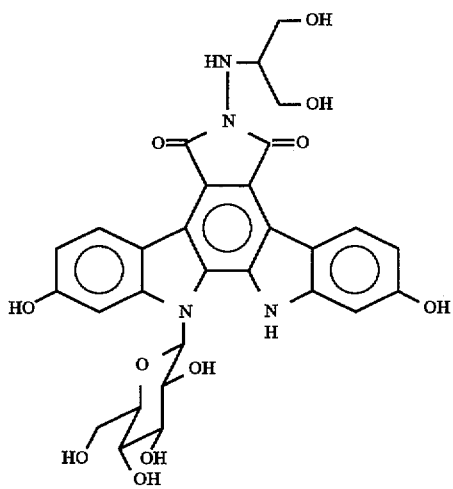

(58)

1) 10.0 of dihydroxyacetone dimer and 14.7 g of carbazi acid tert-butyl ester were dissolved in 500 ml of ethanol, and the solution was stirred at room temperature for 15 hours. The reaction solution was concentrated under reduced pressure, and the residue was recrystallized from ethyl acetate to give 18.67 g of 2-(tert-butyloxycarbonyl)hydrazono-1,3-propanediol as a colorless solid.

Rf value: 0.49 (produced by Merck Co., Kiesel gel 60 $F_{254}$, developing solvent; dichloromethane:methanol= 10:1.5)

$^1$H-NMR (300 MHz, DMSO-$d_6$), δ (ppm): 1.49 (9H, s), 3.92 (2H, d, J=5.2 Hz), 4.24 (2H, d, J=5.0 Hz), 4.88 (1H, t, J=5.8 Hz), 5.61 (1H, t, J=5.1 Hz), 9.98 (1H, brs)

2) 50 ml of borane-tetrahydrofuran complex was added to 5.00 g of 2-(tert-butyloxycarbonyl)hydrazono-1,3-propanediol at 0° C. and the mixture was stirred at room temperature for 0.5 hour. 25 ml of 6N hydrochloric acid was added to the reaction solution at room temperature, and the mixture was refluxed with heating for 1.5 hours. The reaction solution was concentrated under reduced pressure, and the resultant residue was adsorbed on an $H^+$ type of Dowex 50 WX4, washed and eluted with 0.5N ammonia water. Fractions containing the desired product were combined and concentrated under reduced pressure, and the resultant oily matter was adsorbed on an $NH_4^+$ type of IRC-50 and eluted with water. Fractions containing the desired product were combined and concentrated under reduced pressure to give 2.26 g of 2-hydrazino-1,3-propanediol as a colorless solid.

FAB-MS (m/z): 107 (M+H)$^+$ $^1$H-NMR (200 MHz, $CD_3OD$), δ (ppm): 2.78 (1H, m), 3.50–3.75 (4H, m)

3) 500 mg of the compound obtained in Example C and 152 mg of 2-hydrazino-1,3-propanediol obtained in 2) were dissolved in 50 ml of N,N-dimethylformamide, and the solution was stirred at 80° C. for 1 hour. The reaction solution was concentrated under reduced pressure, and the residue was purified by Sephadex LH20 (chloroform:methanol:ethanol:water=5:2:2:1) to give 418 mg of the captioned compound represented by the formula (58).

Rf value: 0.20 (produced by Merck Co,. Kiesel gel 60 $F_{254}$, developing solvent; dichloromethane:methanol:tetrahydrofuran=3:1:1)

FAB-MS (m/z): 609 (M+H)$^+$ $^1$H-NMR (300 MHz, DMSO-d$_6$), δ (ppm): 3.2–3.3 (1H, m), 3.4–3.6 (6H, m), 3.78 (1H, m), 3.85–3.95 (2H), 4.02 (1H, m), 4.53 (2H, t, J=5.4 Hz), 4.91 (1H, d, J=5.1 Hz), 5.11 (1H, d, J=5.3 Hz), 5.32 (1H, d, J=4.6 Hz), 5.55 (1H, d, J=2.6 Hz), 5.86 (1H, t, J=3.8 Hz), 5.97 (1H, d, J=8.3 Hz), 6.80 (1H, dd, J=2.0 Hz, 8.6 Hz), 6.82 (1H, dd, J=2.0 Hz, 8.6 Hz), 6.98 (1H, d, J=2.0 Hz), 7.18 (1H, d, J=1.7 Hz), 8.79 (1H, d, J=8.6 Hz), 8.87 (1H, d, J=8.6 Hz), 9.75 (1H, s), 9.78 (1H, s), 11.20 (1H, s).

EXAMPLE 57

Excellent antitumor activities of the compounds (54) to (58) obtained in Examples 52 to 56 are exhibited by the following pharmacological tests.

(1) Proliferation inhibition activity (CTX) against various cancer cells in culture Measurement method:

100 μportions of a cell culturing medium (10% fetal bovine serum-containing-RPMI-1640 medium) containing 3×10$^3$ mouse leukemia cell (P388), human gastric cancer cell (MKN-45), human lung cancer cell (PC-13) or human colon cancer cell (DLD-1) were put in a 96-well microplate, the cells were cultured under 5% $CO_2$ at 37° C. for 24 hours, 10 μl each of test solutions containing test compounds respectively were added respectively, and the cells were further cultured under 5% $CO_2$ at 37° C. for 72 hours. 10 μl portions of 0.5% Thiazoyl Blue were added to the culture medium, and incubation was carried out under 5% $CO_2$ at 37° C. for 2 hours to carry out enzymatic reaction. 20% sodium dodecyl sulfate (SDS) was added to discontinue the reaction, incubation was further carried out at 37° C. for 4 hours to dissolve the formed dye, and absorbance at 550 nm was measured and compared with time control group. The results are shown in the following Table 4.

TABLE 4

| Test compound | Proliferation inhibition activities (CTX) against various cancer cells | | | |
|---|---|---|---|---|
| | CTX (μM) | | | |
| | P388 | MKN-45 | PC-13 | DLD-1 |
| Example 52 | 0.00048 | 0.0017 | 0.0058 | 0.058 |
| Example 53 | 0.0022 | 0.0069 | 0.014 | 0.025 |
| Example 54 | 0.0014 | 0.0066 | 0.037 | 0.039 |
| Example 55 | 0.0012 | 0.0050 | 0.019 | 0.057 |
| Example 56 | 0.0015 | 0.0048 | 0.056 | 0.12 |

(2) Growth inhibitory effects against human gastric cancer MKN-45 in mice

MKN-45 solid tumor previously subcutaneously implanted into a nude mouse and grown was cut into pieces, and the pieces each 3 mm cubic were subcutaneously implanted into test mice, respectively. From the time when each tumor grew to 0.3 cm$^3$ after the implantation, predetermined quantities of test chemicals were injected into the tail veins of the mice once a day for continuous five days, and after recuperation for 2 days, further injected for 5 days (treatment schedule: 5/w×2) or four times every 3 to 4 days (treatment schedule: 2/w×2) for treatment, respectively. 20 days or 32 days after the start of treatment, each tumor was taken out, and weighed whereby tumor growth inhibition ratios were calculated and total doses (GID$_{75}$, mg/kg) to inhibit tumor growth to an extent of 75% were calculated. The results are shown in the following Table 5.

TABLE 5

| Growth inhibitory effects of compounds of this invention on human gastric cancer MKH-45 in mice | | |
|---|---|---|
| Test compound | Treatment schedule | GID$_{75}$ (mg/kg total) |
| Example 52 | 5/w × 2 | 12 |
| Example 52 | 2/w × 2 | 7.2 |
| Example 56 | 2/w × 2 | 3.0 |

EXAMPLE 58

50 g of the compound of Example 5 was dissolved in a solution wherein 600 g of macrogol 400 of the Japanese Pharmacopoeia was dissolved in 400 g of distilled water for injection, and the solution was filtered for removal of bacteria using a filter of 0.2 μm. 5 ml portions of the filtrate were filled into washed and sterilized vials according to a conventional method, and the vials were stopped and capped to give an injection containing 250 mg of the compound of Example 5 per vial. Administration is made using an agent for intravenous drip wherein 5 to 10 ml of this injection (250 to 500 mg of the compound of Example 5) was added to and diluted with 500 ml of an infusion such as 5% glucose.

The compounds of formula (I) according to this invention not only have excellent anti-tumor activity as evidenced by the foregoing data, but also are highly advantageous over rebeccamycin and other known rebeccamycin derivatives, such as BE-13793C, in view of their greatly enhanced water solubility. This water solubility allows the invention compounds to be dissolved in distilled water and other aqueous solvents useful in formulating, for instance, intravenous injection compositions. The enhanced water solubility may be appreciated from the following water solubility test.

EXAMPLE 59

I. Water solubility test:

Water solubility was compared between the compounds in Examples 2, 3, 5, 6, 8–11, 13, 18, 20, 25, 30, 38 and 41–44 of the present specification, and the rebeccamycin disclosed in Richard P. Joyce et al., J. Org. Chem., Vol.52, No.7, 1987, pp. 1177–1185, page 1178, as Compound 3 which is represented by the following formula:

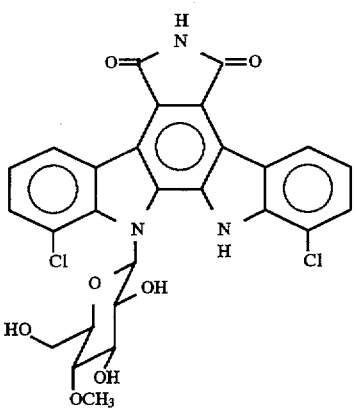

I-1. Test method:

Test samples (200 μg) were suspended in 1.0 ml of water and shaked for 10 min. and then centrifuged at 3,000 rpm for 10 min. When precipitates were observed, supernatant fraction was quantitated by HPLC method.

Column; Chromatorex ODS (4.6×250 mm)

Mobile Phase; 80% MeOH

Flow rate; 1.0 ml/min

Detection; UV 320 nm

I-2. Results:

The results are shown in Table A.

TABLE A

| Water solubility of rebeccamycin and Example compounds. | |
|---|---|
| Compound | Water solubility (mg/ml) |
| rebeccamycin | 0.001 |
| Compound of Example 2 | >0.2 |
| Compound of Example 3 | >0.2 |
| Compound of Example 5 | 0.2 |
| Compound of Example 6 | >0.2 |
| Compound of Example 8 | >0.2 |
| Compound of Example 9 | >0.2 |
| Compound of Example 10 | >0.2 |
| Compound of Example 11 | >0.2 |
| Compound of Example 13 | >0.2 |
| Compound of Example 18 | >0.2 |
| Compound of Example 20 | >0.2 |
| Compound of Example 25 | >0.2 |
| Compound of Example 30 | >0.2 |
| Compound of Example 38 | >0.2 |
| Compound of Example 41 | >0.2 |
| Compound of Example 42 | >0.2 |
| Compound of Example 43 | >0.2 |
| Compound of Example 44 | >0.2 |

The compounds of this invention also have improved antitumor activity as compared to other known water soluble derivatives of rebeccamycin as shown in the following example.

EXAMPLE 60

Antitumor activity was compared between the compounds shown in Examples 1, 2, 5, 6, 9, 11, 24, 25, 30, 36, 39 and 50 and 6-(2-diethylaminoethyl) rebeccamycin (hereinafter called "DEAE-rebeccamycin") mentioned in The Journal of Antibiotics, Vol.43, No.1, pp 125–127, which is represented by the following formula:

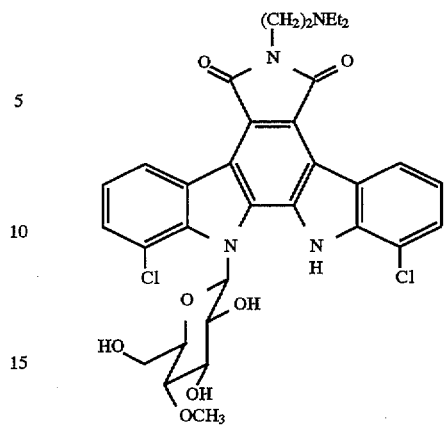

Test method:

Therapeutic effect of a test compound against mouse tumor (p 388) was determined in the same manner as in the present specification, page 20, line 22 to page 21, line 13.

The tests were conducted four times, and a group to which no medicine was administered was employed as a control.

The results of the tests are shown in the following Tables B–E:

TABLE B

| Dose mg/kg/day | DEAE-rebeccamycin MST[1] (T/C %)[2] | Compound of Example 5 MST (T/C %) |
|---|---|---|
| 0 | 10.6 (100) | 12.3 (100) |
| 0.3 | — | 16.8 (137) |
| 0.63 | 11.6 (109) | — |
| 1.0 | — | 16.8 (137) |
| 2.5 | 13.2 (125) | — |
| 3.0 | — | 17.8 (145) |
| 10 | 14.8 (140) | 26.6 (216) |
| 30 | — | >27.4 (>223) |
| 40 | 13.4 (126) | — |
| 100 | toxic | >52.4 (>426) |

TABLE C

| Compound | Dose mg/kg | MST day | T/C % |
|---|---|---|---|
| Control | — | 12.8 | 100 |
| Compound of Example 1 | 10 | 18.2 | 142 |
| | 30 | >31.0 | >242 |
| | 100 | >52.8 | >413 |
| Compound of Example 2 | 1 | 15.8 | 128 |
| | 3 | 17.8 | 145 |
| | 10 | >26.4 | >245 |
| | 30 | >42.2 | >343 |
| | 100 | >47.2 | >384 |

TABLE D

| Compound | Dose mg/kg | MST day | T/C % |
|---|---|---|---|
| Control | — | 13.0 | 100 |
| Compound of Example 5 | 1 | 21.2 | 163 |
| | 3 | 30.4 | 234 |
| | 10 | 26.5 | 204 |
| Compound of Example 6 | 3 | 24.8 | 191 |
| | 10 | >28.8 | >222 |

TABLE D-continued

| Compound | Dose mg/kg | MST day | T/C % |
|---|---|---|---|
| | 30 | >44.0 | >338 |
| | 100 | >43.0 | >331 |
| Compound of Example 9 | 1 | 25.4 | 195 |
| | 3 | >32.6 | >251 |
| | 10 | >60.0 | >462 |
| Compound of Example 11 | 3 | 21.4 | 165 |
| | 10 | 24.0 | 185 |
| | 30 | >32.8 | >252 |
| Compound of Example 25 | 1 | >29.8 | >229 |
| | 3 | >34.8 | >268 |
| | 10 | >54.2 | >417 |
| | 30 | >56.6 | >435 |
| Compound of Example 30 | 3 | 22.0 | 169 |
| | 10 | >27.3 | >210 |
| | 30 | >43.2 | >332 |
| | 100 | >52.6 | >405 |

TABLE E

| Compound | Dose mg/kg | MST day | T/C % |
|---|---|---|---|
| Control | — | 11.0 | 100 |
| Compound of Example 5 | 12.5 | 19.0 | 172 |
| | 50 | 25.0 | 227 |
| Compound of Example 24 | 3.13 | 15.0 | 136 |
| | 12.5 | 17.0 | 154 |
| | 50 | 26.0 | 236 |
| Compound of Example 36 | 3.13 | 15.0 | 136 |
| | 12.5 | 20.0 | 181 |
| | 50 | 28.0 | 254 |
| Compound of Example 39 | 12.5 | 17.0 | 154 |
| | 50 | 26.0 | 236 |
| Compound of Example 50 | 12.5 | 18.0 | 163 |
| | 50 | 27.0 | 245 |

1) MST=Mean Survival Time in Days
2) T/C=(MST Treated/MST Control)×100%

CDF1 mice were inoculated intraperitoneally (i.p.) with $10^8$ P388 cells on day 0 and treated with each sample consecutively from day 1 for 10 days (Q1D for day 1–10). Ten mice were used for control group and 5 mice were used for each dose.

We claim:

1. A process for the preparation of a compound of the formula (I)

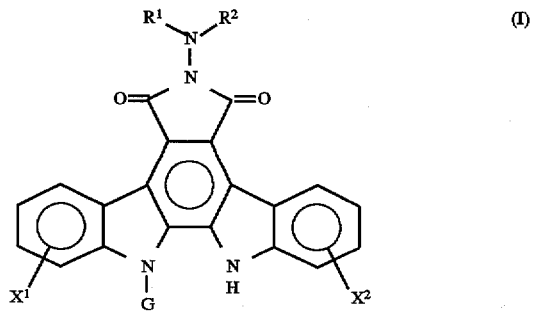

wherein $R^1$ and $R^2$ each, independently, represent a hydrogen atom, $C_1$–$C_8$ alkyl group, $C_3$–$C_6$ alkenyl group, $C_6$–$C_{12}$ aromatic hydrocarbon group, $C_1$–$C_6$ alkyl group substituted by $C_6$–$C_{12}$ aromatic hydrocarbon group or 5- or 6-membered nonaromatic or aromatic heterocyclic group containing 1 to 4 hetero atoms selected from the group consisting of nitrogen atom, oxygen atom and sulfur atom, wherein the $C_1$–$C_6$ alkyl group, $C_3$–$C_6$ alkenyl group, $C_3$–$C_6$ alkynyl group, $C_6$–$C_{12}$ aromatic hydrocarbon group, $C_1$–$C_6$ alkyl group substituted by $C_6$–$C_{12}$ aromatic hydrocarbon group and heterocyclic group may be substituted by 1 to 5 substituents selected from the group consisting of carboxyl group, carbamoyl group, $SO_3H$, $NH_2$, cyano group, mono-($C_1$–$C_6$ alkyl) amino group, di($C_1$–$C_6$ alkyl)amino group, hydroxyl group, and halogen atom; or represent a group of the formula —Y—$R^3$, wherein Y represents a carbonyl group, thiocarbonyl group or sulfonyl group, and $R^3$ represents a hydrogen atom, $C_1$–$C_6$ alkyl group, $C_3$–$C_6$ cycloalkyl group, $C_4$–$C_{10}$ cycloalkylalkyl group, $C_6$–$C_{12}$ aromatic hydrocarbon group, $C_1$–$C_6$ alkyl group substituted by $C_6$–$C_{12}$ aromatic hydrocarbon group, $C_1$–$C_6$ alkoxy group, NHNH$_2$, NH$_2$, amino group substituted by $C_6$–$C_{12}$ aromatic hydrocarbon group, carbamoyl group or 5- or 6-membered nonaromatic or aromatic heterocyclic group containing 1 to 4 hetero atoms selected form the group consisting of nitrogen atom, oxygen atom and sulfur atom, wherein the $C_1$–$C_6$ alkyl group, $C_3$–$C_6$ cycloalkyl group, $C_4$–$C_{10}$ cycloalkylalkyl group, $C_6$–$C_{12}$ aromatic hydrocarbon group, $C_1$–$C_6$ alkyl group substituted by $C_6$–$C_{12}$ aromatic hydrocarbon group and 5- or 6-membered nonaromatic or aromatic heterocyclic group may be substituted by 1 to 4 substituents selected from the group consisting of halogen atom, unprotected hydroxyl group, hydroxyl group protected by a protective group selected from the group consisting of $C_2$–$C_6$ alkanoyl group, $C_2$–$C_7$ alkoxycarbonyl group, benzoyl group, acetal-forming group, benzyl group and benzyl group substituted by $C_1$–$C_6$ alkoxy group, nitro group, $NH_2$, carboxyl group, carbamoyl group, cyano group or $C_2$–$C_7$ alkoxycarbonyl group, and the $NH_2$ and carbamoyl group are unsubstituted or mono- or di-substituted by unsubstituted $C_1$–$C_6$ alkyl group(s) or by $C_1$–$C_6$ alkyl group(s) substituted by substituent(s) selected from the group consisting of halogen atom, hydroxyl group, $NH_2$, carboxyl group, carbamoyl group and $C_2$–$C_7$ alkoxycarbamoyl group; or $R^1$ and $R^2$ combine to form an unsubstituted $C_1$–$C_6$ alkylidene group or a $C_1$–$C_6$ alkylidene group substituted by 1 to 4 substituents selected form the group consisting of $NH_2$, mono-($C_1$–$C_6$ alkyl)amino group, di-($C_1$–$C_6$ alkyl)amino group, hydroxyl group, carboxyl group and $SO_3H$; or $R^1$ and $R^2$ combine together with the nitrogen atom to which they are bonded to form a 5- or 6-membered nonaromatic heterocyclic group containing 1 to 4 hetero atoms selected from the group consisting of nitrogen atom, oxygen atom and sulfur atom, and the heterocyclic group may be substituted on the ring by unsubstituted $C_1$–$C_6$ alkyl group(s) and by $C_1$–$C_6$ alkyl groups substituted by group(s) selected form the group consisting of $NH_2$, hydroxyl group, carboxyl group and $SO_3H$;

G represents pentose group or hexose group, and $X^1$ and $X^2$ each, independently, represent a hydrogen atom, halogen atom, $NH_2$, mono-($C_1$–$C_6$ alkyl)amino group, di-($C_1$–$C_6$ alkyl)amino group, hydroxyl group, $C_1$–$C_6$ alkoxy group, $C_1$–$C_6$ alkoxy group substituted by $C_6$–$C_{12}$ aromatic hydrocarbon group, carboxyl group, $C_2$–$C_7$ alkoxycarbonyl group or $C_1$–$C_6$ alkyl group, or a pharmaceutically acceptable salt thereof, which comprises reacting a compound represented by the following formula (II) or formula (III) wherein any functional group may be protected,

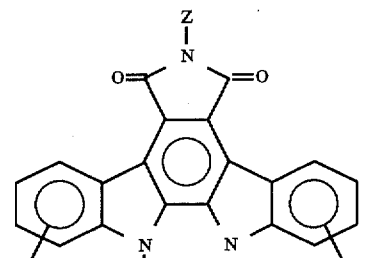

or

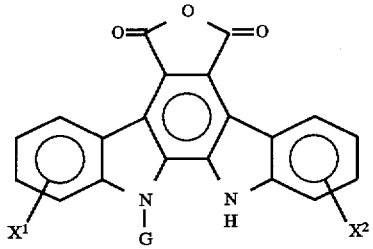

wherein

Z represents a hydrogen atom or substituted or unsubstituted lower alkyl group, and $X^1$, $X^2$ and G have the same meaning as defined above, with a compound represented by the following formula (IV) or a derivative thereof wherein functional groups are protected,

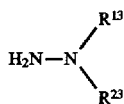

wherein $R^{13}$ and $R^{23}$ each independently represent a hydrogen atom, lower alkyl group, lower alkenyl group, lower alkynyl group, aryl group, aralkyl group or heterocyclic group, wherein the lower alkyl group, lower alkenyl group, lower alkynyl group, aryl group, alkyl group and heterocyclic group may have 1 to 5 substitutents selected from the group consisting of carboxyl groups, carbamoyl groups, sulfo groups, amino groups, cyano groups, mono-lower alkylamino group, di-lower alkylamino group, hydroxyl groups and halogen atoms, or a group of the formula —Y—$R^3$, wherein Y represents a carbonyl group, thiocarbonyl group or sulfonyl group, and $R^3$ represents a hydrogen atom, lower alkyl group, cycloalkyl group, cycloalkylalkyl group, aryl group, aralkyl group, lower alkoxy group, hydrazino group, amino group, arylamino group, carbamoyl group or heterocyclic group, wherein the lower alkyl group, cycloalkyl group, cycloalkylalkyl group, aryl group, aralkyl group and heterocyclic group may each have 1 to 4 substituents selected from the group consisting of halogen atoms, optionally protected hydroxyl groups, amino groups, carboxyl groups, carbamoyl groups, cyano groups and lower alkoxycarbonyl groups, and the amino group and carbamoyl group may each be mono- or di-substituted by lower alkyl group(s) optionally substituted by group(s) selected from the group consisting of halogen atoms, hydroxyl groups, amino groups, carboxyl groups, carbamoyl groups and lower alkoxycarbonyl groups; or $R^{13}$ and $R^{23}$ combine together with the nitrogen atom to which they bind to form a heterocyclic group, wherein the heterocyclic group may have on the ring lower alkyl group(s) which may be substituted by groups selected from the group consisting of amino groups, hydroxyl groups, carboxyl groups and sulfo groups, wherein when $R^{13}$ and/or $R^{23}$ contain a functional group, each functional group is protected, optionally, removing protective group(s) existing in the product, to prepare a compound represented by formula (Ic)

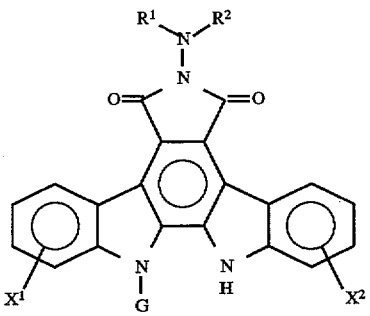

wherein $R^{13}$, $R^{23}$, $X^1$, $X^2$ and G have the same meanings as defined above;

or either formylating, alkylating, alkenylating, alkynylating, aralkylating, carbamoylating, thiocarbamoylating, alkanoylating or sulfonylating the amino group

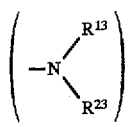

of the compound of the above formula (Ic) wherein any functional groups may be protected when $R^{13}$ and $R^{23}$ represent a hydrogen atom, or condensing the above compound with a compound represented by the following formula (V) or a derivative thereof wherein a functional group is protected $$\text{OHC—R}^6 \qquad (V)$$

wherein $R^6$ represents a hydrogen atom or carboxyl group, or a lower alkyl group which may have 1 to 4 substituents selected from the group consisting of amino groups, mono-lower alkylamino groups, di-lower alkylamino group, hydroxyl groups, carboxyl groups and sulfo groups, and, if necessary, removing the protective groups existing in the product; or reducing the double bonds of the compound of the above formula (Ic) when $R^{13}$ and/or $R^{23}$ contain a double bond, or the compound prepared by condensing the compound of the formula (Ic) with the compound of the formula (V) or the derivative thereof wherein the functional groups are protected, and if necessary removing the protective group(s) existing in the product; and if necessary, converting the resulting compound of the formula (I) into a pharmaceutically acceptable salt.

2. The process of claim 1 wherein the compound of formula (II) is used.

3. The process of claim 1 wherein the compound of formula (III) is used.

* * * * *

UNITED STATES PATENT AND TRADEMARK OFFICE
CERTIFICATE OF CORRECTION

PATENT NO.    : 5,668,271
DATED         : September 16, 1997
INVENTOR(S)   : Katsuhisa Kojiri et al.

It is certified that error appears in the above-identified patent and that said Letters Patent is hereby corrected as shown below:

Column 42,
Lines 48-65, formula (36) should appear as follows:

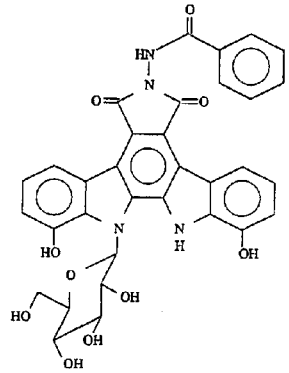

Column 43,
Lines 25-43, formula (37) should appear as follows:

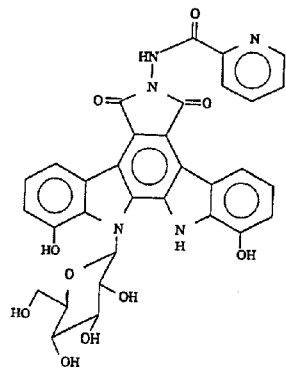

UNITED STATES PATENT AND TRADEMARK OFFICE
CERTIFICATE OF CORRECTION

PATENT NO.    : 5,668,271
DATED         : September 16, 1997
INVENTOR(S)   : Katsuhisa Kojiri et al.

It is certified that error appears in the above-identified patent and that said Letters Patent is hereby corrected as shown below:

Column 68,
Lines 13-25, formula (Ic) should appear as follows:

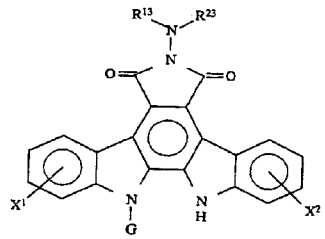

Signed and Sealed this

Twelfth Day of August, 2003

JAMES E. ROGAN
*Director of the United States Patent and Trademark Office*